(12) United States Patent
Singer et al.

(10) Patent No.: US 6,235,871 B1
(45) Date of Patent: May 22, 2001

(54) SYNTHESIS OF OLIGOARYLAMINES, AND USES AND REAGENTS RELATED THERETO

(75) Inventors: Robert A. Singer, Belmont, MA (US); Joseph P. Sadighi, Boston; Stephen L. Buchwald, Newton, both of MA (US); Thomas Mackewitz, Mannheim (DE)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/203,726

(22) Filed: Dec. 2, 1998

Related U.S. Application Data
(60) Provisional application No. 60/067,275, filed on Dec. 3, 1997.

(51) Int. Cl.[7] ............................. C08G 73/00; C08G 73/02
(52) U.S. Cl. ........................ 528/485; 528/422; 528/488; 528/492; 564/386; 564/376; 564/391; 564/395; 252/644; 430/270.1; 430/4
(58) Field of Search ...................... 528/485, 422, 528/488, 492; 564/386, 376, 391, 395; 252/644; 430/270.1, 4

(56) References Cited

U.S. PATENT DOCUMENTS

| | | | |
|---|---|---|---|
| 5,288,514 | 2/1994 | Ellman | 427/2 |
| 5,359,115 | 10/1994 | Campbell et al. | 558/110 |
| 5,362,899 | 11/1994 | Campbell | 558/108 |
| 5,576,460 | 11/1996 | Buchwald et al. | 564/386 |

FOREIGN PATENT DOCUMENTS

| | | |
|---|---|---|
| WO91/07087 | 5/1991 | (WO). |
| WO92/10092 | 6/1992 | (WO). |
| WO93-09668 | 5/1993 | (WO). |
| WO93/20242 | 10/1993 | (WO). |
| WO94/08051 | 4/1994 | (WO). |

OTHER PUBLICATIONS

Amit, B. et al., "Photosensitive Protecting Groups of Amino Sugars and Their Use in Glycside Synthesis. 2–Nitrobenzyloxycarbonylamino and 6–Nitrobenzyloxycarbonylamino Derivities", *J. Org. Chem.*, 39:192–196 (1974).

Chen S. et al., "Electrically Conductive Polyaniline–Poly(vinyl alcohol) Composite Films: Physical Properties and Morphological Structures", *Macromolecules*, 24:1242–1248 (1991).

D'Aprano G. et al., "Synthesis and Characterization of Polyaniline Derivatives: Poly(2–alkoxyanilines) and Poly(2, 5–dialkoxyanilines)", *Chem. Mater.*, 7:33–42 (1995).

DeBerry, D. "Modification of the Electrochemical and Corrosion Behavior of Stainless Steels with an Electroactive Coating", *J. Electrochem. Soc.*, 132:1022–1026 (1985).

(List continued on next page.)

*Primary Examiner*—Duc Truong
(74) *Attorney, Agent, or Firm*—Matthew P. Vincent; Dana M. Gordon; Foley Hoag & Eliot LLP

(57) ABSTRACT

The transition metal-catalyzed amination of aryl halides, in conjunction with an orthogonal protective group scheme, forms the basis of two routes to oligoaniline precursors. The oligoaniline precursors are soluble in a variety of common organic solvents, and are easily converted to the deprotected oligoanilines. The method allows the preparation of oligoanilines of even or odd chain lengths, and the incorporation of a variety of functional groups into the oligomers. Polyanilines of low polydispersity can also be prepared by this method.

37 Claims, 8 Drawing Sheets

OTHER PUBLICATIONS

Driver, M. S. et al., "A. Second Generation Catalyst for Aryl Halide Amination: Mixed Secondary Amines from Aryl Halides and Primary Amines Catalyzed by (DPPF)PdCl2", *J. Chem. Soc*, 118:7217–7218 (1996).

Graf, D. et al., "From Monomers to π–Stacks. A Comprehensive Study of the Structure and properties of Monomeric, π–Dimerized, and πStacked Forms of the Cation Radical of 3', 4'–Dibutyl–2,5"–diphenyl–2,2':5',2"–terthiophene", *J. Am. Chem. Soc.*, 119:5888–5599 (1997).

Guram, A. S. et al., "A Simple Catalytic Method For the Conversion of Ayrl Bromides to Arylamines", *Agnew. Chem. Int. Ed. Engl.*, 34:1348–1350 (1995).

Hádek, V. et al., "Electric Properties of Donor–Acceptor Comlexes of Olgoanilinic Compounds", *Collection Czechoslov. Chem. Commun.*, 34:3139–3144 (1969).

Huang, W. et al., "Polyaniline, a Novel Conducting Polymer", *J. Chem. Soc., Faraday Trans. 1*, 82:2385–2400 (1986).

Izatt, R. et al., "Thermodynamic and Kinetic Data For Cation–Macrocycle Interation", *Chem. Rev.*, 85:271–339 (1985).

Lu F.–L.et al., "Phenyl–Capped Octaaniline(COA): An Excellent Model for Polyaniline", *J. AM. Chem. Soc.*, 108:8311–8313 (1986).

Moll, T. and Heinze, J., "Electrochemical and spectroscopic properties of oligoanilines", *6001 Chemical Abstracts*, 119:18, p. 708 (1993).

Ochi, M. et al., "Preperation of Linear Oliganiline Dervatives Using Titanium Alkoxide as a Condensing Agent", *Bull. Chem. Soc. Japan*, 67:1749–1752 (1994).

Pillai, V. N. R. "Photoremovable Protecting Groups in Organic Synthesis", *Synthesis*, Jan.:1–26 (1980).

Sadighi, J. P. et al., "Palladium–Catalyzed Synthesis of Monodisperse, COntrolled–Length and Functionalized Oligoanilines", *J. Am. Chem. Soc.*, 120:20, pp. 4961–4976 (1998).

Singer, R. A. eta al., "A General Synthesis oif End–Functionalized Oligoanilines via Palladium–Catalyzed Amination", *J. Am. Chem. Soc.*, 120:1, pp. 213–214 (1998).

Swager, T. M. et al., "Molecular Recognition and Chemoresistive Materials", *Adv. Mater*, 6:595–597 (1994).

Walton, D.R.M. "The Protection OF Aminophenyl Groups in Organometallic Syntheses", *J. Chem. Soc.*, C;1706–1707 (1966).

Wolfe, J.P. et al., "An Ammonia Equivalent for the Palladium–Catalyzed Amination of Aryl Halides and Triflates", *Tetrahedron Letters*, 38:6367–6370 (1997).

Wolfe, J.P. et al., "An Improved Catalyst System for Aromatic Carbon–Nitrogen Bond Formation: The Possible Involvement of Bis(Phosphine) Palladium Complexes as Key Intermediates", *J. Am. Chem. Soc.*, 118:7215–7216 (1996).

Wolfe, J.P. et al., "Palladium–Catalyzed Amination of Aryl Triflates", *J. Org. Chem*, 62:1264–1267 (1997).

Wudl, F. et al., "Poly(ρ–phenyleneamineimine): Synthesis and Comparison to Polyaniline", *J. AM. Chem. Soc.*, 109:3677–3684 (1987).

Phenyl-Capped Heptaaniline:

Phenyl-Capped Octaanilines:

Phenyl-Capped Nonaaniline:

Phenyl-Capped Decaaniline:

SYNTHESIS OF OLIGOARYLAMINES, AND USES AND REAGENTS RELATED THERETO

RELATED APPLICATIONS

This application claims priority to provisional application Ser. No. 60/067,275, filed Dec. 3, 1997, which is incorporated herein by reference.

GOVERNMENT FUNDING

This invention was supported in part with funds provided by the Office of Naval Research. The government has certain rights in the invention.

BACKGROUND OF THE INVENTION

Polyaniline has attracted much attention in the field of organic conducting polymers due to its robust nature in the doped emeraldine state. See, for example, Huang et al. (1986) *J. Chem. Soc. Faraday Trans.* 82:2385–2400; Chen et al. (1991) *Macromolecules* 24:1242–1248; and Chiang et al. (1986) *Synth. Met.* 13:193–205. Among the many industrial applications it has found are its use as components in rechargeable batteries (MacDiarmid et al. (1986) *Mol. Cryst. Liq. Cryst.* 121:187–190), electromagnetic interference shielding (Taka et al. (1991) *Synth. Met.* 41:1177–1180; Colaneri et al. (1992) *IEEE Trans. Instrum. Meas.* 41:291; and Joo et al. (1994) *Appl. Phys. Lett.* 65:2278–2280), and anticorrosion coatings for steel (DeBerry et al. (1985) *J. Electrochem. Soc.* 132:1022–1026; Ahmad et al. (1996) *Synth. Met.* 78:103–110; and Lu et al. (1995) *Synth. Met.* 71:2163–2166).

In 1986, Wudl and coworkers demonstrated that synthetically prepared phenyl-capped octaaniline exhibited properties similar to bulk polyaniline (comparable UV/vis, IR, CV, and conductivity). See Lu et al. (1986) *J. Am. Chem. Soc.* 108:8311–8313; Wudl et al. (1987) *J. Am. Chem. Soc.* 109:3677–3684. Consequently, an octaaniline may be considered a good model or substitute for applications involving polyaniline. Aside from the modified Honzl condensation method employed by Wudl for synthesizing oligoanilines, other methods of preparation include titanium alkoxide-mediated couplings of aniline derivatives (Ochi et al. (1994) *J. Bull. Chem. Soc. Jpn.* 67:1749–1752), Ullmann couplings (Rebourt et al. (1997) *Synth. Met.* 84:65–66), and an adaptation of the Willstätter-Moore approach (Zhang et al. (1997) *J. Synth. Met.* 84:119–120). However, none of these methods have demonstrated generality in the choice of substrates for oligomerizations, and all lack the ability to functionalize end groups.

BRIEF SUMMARY OF THE INVENTION

New methods for the synthesis of electroactive polymers and the preparation of films thereof are disclosed. Oligomeric variants of these electroactive compounds are also prepared by similar methods here disclosed. Preparation of both types of compounds hinges upon the transition metal-mediated coupling of aryl amines with activated aryl compounds. The method disclosed herein provides for the synthesis of electroactive compounds which are stable to ambient atmosphere, are soluble in common organic solvents, and can be readily manipulated into useful forms.

In one aspect of the invention, a process is described for the synthesis of compounds comprising alternating aryl and heteroatomic groups by means of the transition metal-mediated process described above.

Another aspect of the invention provides for the synthesis of symmetrical compounds by means of the bidirectional chain extension of a core fragment comprising alternating aryl and heteroatomic functionalities.

In another aspect of the invention, a process is described for the synthesis of polymeric compounds comprising alternating aryl and heteroatomic groups.

A further aspect of the invention provides for the synthesis of protected oligoanilines by means of the transition metal-mediated coupling of an aryl amine with an activated aryl compound.

Yet another aspect of the invention describes the preparation of protected symmetrical oligoanilines through the bidirectional chain extension of a core oligoaniline subunit.

An additional aspect of the invention provides for the transition metal-mediated polymerization of oligoaniline subunits for the preparation of protected polyanilines.

In another aspect of the invention, a process is described for the metallation and substitution of activated protected aniline rings.

A further aspect of the invention provides compounds comprising chains of alternating heteroatomic and aryl moieties.

Yet another aspect of the invention provides protected oligoanilines which can be deprotected and rendered electroactive under specific conditions.

An additional aspect of the invention provides protected polyanilines of low polydispersity.

In another aspect of the invention, protected versions of electroactive polyanilines which can be deprotected and activated under specific conditions are provided.

DETAILED DESCRIPTION OF THE INVENTION

Figure 1:
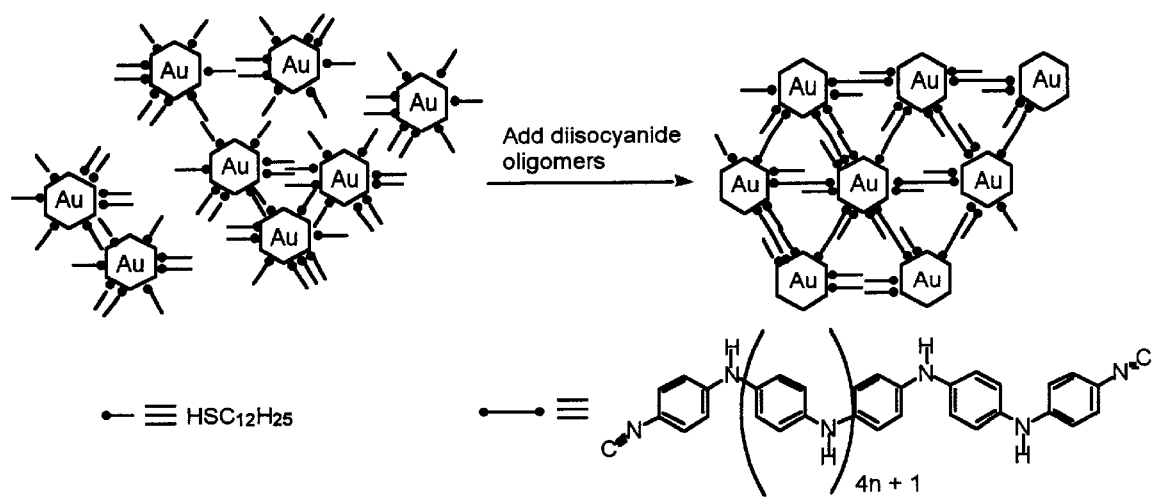
FIG. 1. Scheme 16. Formation of an ordered matrix of oligoanilines and gold clusters.

The recognition of certain organic polymers as conductors in the 1970's launched efforts to develop organic materials to aid and replace conventional metal conductors. Advantages organic materials typically have over metals include their light weight, corrosion resistance, potential for relatively inexpensive manufacture, potential for recycling, tendancy to be more malleable or flexible, and electronic properties or redox potentials which are tunable through derivatization or selective synthesis. While methods have become available to produce conducting polymers, their application has not become widespread due to their generally poor solubility in organic media and instability to air in the doped (conducting) state. In contrast, polyaniline has found many industrial applications because of its relatively robust nature in the conducting state. Some of its applications include use as components in rechargeable batteries, electrochromic displays, electromechanical actuators, anti-corrision coatings for steel, and electromagnetic interference shielding. Because of the limited means available for producing polyaniline and other conducting polymers, materials have yet to be developed with more favorable physical properties for processing in industrial applications.

As prepared by random chemical oxidation, polyaniline is rather intractable and highly polydisperse. Existing routes to discrete, monodisperse oligomers have afforded considerable insight into the behavior of the polymer, but are not general with respect to providing access to numerous, monodisperse chain lengths or the incorporation of functionality into the oligomers.

The present invention, on the other hand, is directed towards a general synthesis of aniline and other arylamine oligomers with controlled chain lengths and comprising hitherto inaccessible functionality. In a preferred embodiment, the subject method employs a transition metal-catalyzed carbon-nitrogen bond formation in conjunction with an orthogonal protecting group scheme to control the reactions. The protecting group(s) can be selected to confer suitable solubility properties upon the oligomers, which may be processed, for example, as solubulized derivatives before conversion to their electroactive forms.

In certain embodiments, the subject reaction comprises a cross-coupling of a nitrogen-substituted molecule comprising alternating aryl and heteroatom units, represented by the general formulas (Ia), (Ib), and (Ie):

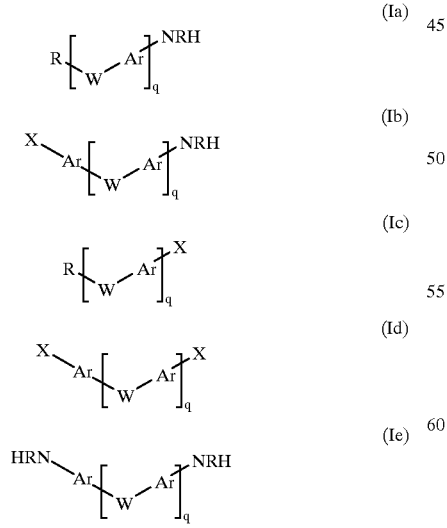

with related compounds bearing activated groups (such as Ib, Ic, or Id), as well as non-oligomeric halide- or sulfonate-substituted aryls, or arylamines, to yield an oligoarylamine, or mixed polymers including diarylamine, diarylether, diarylthioether and/or diarylselenoether subunits. In preferred embodiments:

X represents an activated group which can be replaced by a nucleophilic nitrogen in a transition metal-catalyzed arylation reaction;

W represents, independently for each occurrence, as valence and stability permit, NV, O, S, PR, or Se;

Ar represents, independently for each occurrence, as valence and stability permit, a substituted or unsubstituted aryl group;

V represents, independently for each occurrence, a nitrogen-protecting group;

R represents, independently for each occurrence, as valence and stability permit, H, a substituted or unsubstituted alkyl, aryl, or alkenyl moiety, a formyl, acyl, or sulfonyl moiety, or $-(CH_2)_m-R_8$;

$R_8$ represents, independently for each occurrence, a substituted or unsubstituted aryl, cycloalkyl, cycloalkenyl, heterocyclyl, or polycyclyl;

m is an integer in the range 0–8 inclusive; and q is an integer greater than or equal to 1 (preferably in the range of 1 to 100).

As will be apparent from the following discussion, subunits of a preferred embodiment comprise oligoarylamines, such as may be represented by the general formulas (Ia), (Ib), (Ic), (Id), or (Ie):

wherein Ar, R, V, and X are as defined above and W is NV throughout, though it will be understood that identities of Ar, R, V, and X for each occurrence in Ia, Ib, Ic, Id, and Ie are independent.

In another preferred embodiment, one of the subunits is symmetrical (e.g. (Id) or (Ie)). Reaction of such a subunit with a matching partner (e.g. (Ia) with (Id), or (Ic) with (Ie)) provides a product which is symmetrical.

In one embodiment, in which the subunits are homogeneously coupled by diarylheteroatom linkages, the subject method can be used to produce a polymeric compound represented by the general formula (II):

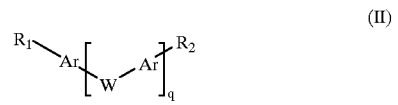

wherein Ar and W are as defined above;

$R_1$ and $R_2$ independently represent hydrogen or any other substitution to terminating Ar residues which stability and valence permit, e.g. $R_1$ and $R_2$ each can be a halogen, a lower alkyl, a lower alkenyl, a lower alkynyl, a carbonyl (e.g. an ester, a carboxyl, or a formyl), a thiocarbonyl (e.g. a thioester, a thiocarboxylate, or a thioformate), a ketone, an aldehyde, an amino, an acylamino, an amido, an amidino, a cyano, a nitro, an azido, a sulfonyl, a sulfoxido, a sulfate, a sulfonyl, a sulfamoyl, a sulfonamido, a sulfonate, a phosphoryl, a phosphonyl, a phosphinate, $-(CH_2)_m-R_8$, $-(CH_2)_m-OH$, $-(CH_2)_m-O$-lower alkyl, $-(CH_2)_m-O$-lower alkenyl, $-(CH_2)_m-O-(CH_2)_n-R_8$, $-(CH_2)_m-SH$, $-(CH_2)_m-S$-lower alkyl, $-(CH_2)_m-S$-lower alkenyl, $-(CH_2)_m-S-(CH_2)_n-R_8$, or protecting groups of the above or a solid or polymeric support, and are preferably selected independently from X and NHR, as defined above);

R₈ represents a substituted or unsubstituted aryl, aralkyl, cycloalkyl, cycloalkenyl, or heterocycle;

n and m are independently for each occurrence an integer in the range of 0 to 6 inclusive; and q is an integer greater than or equal to 2.

In certain embodiments, as discussed below, it will be desirable that the oligmer be symmetrical with respect to terminating groups, e.g. $R_1$ and $R_2$ are identical.

In the above formulas, the activated substituent, X, is characterized as being a good leaving group. In general, the leaving group is a group such as a halide or sulfonate. For the purposes of the present invention, an activated substituent is that moiety whose conjugate acid, HX, has a pKa of less than 5.0. Suitable activated substituents include, by way of example only, halides such as chloride, bromide and iodide, triflate, mesylate and tosylate. In preferred embodiments, the leaving group is a halide selected from iodine and bromine. Chlorine and fluorine can also be used as leaving groups, though other electronegative substitution on the aryl group may be required to activate those halogens as leaving groups in the subject metal-catalyzed cross-coupling reactions.

The aryl moieties of the oligoarylamines include compounds derived from simple aromatic rings (single or polycyclic) such as benzene, naphthalene, anthracene, and phenanthrene; or heteroaromatic rings (single or polycyclic), such as pyrrole, thiophene, thianthrene, furan, pyran, isobenzofuran, chromene, xanthene, phenoxathiin, pyrrole, imidazole, pyrazole, thiazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, and the like.

Suitable aryl groups compounds may have the formula $Z_pAr$, where Z represents one or more optional substituents on the aryl group, though each occurrence of Z (p>1) is independently selected. By way of example only, each incidence of substitution independently can be, as valence and stability permit, a halogen, a lower alkyl, a lower alkenyl, a lower alkynyl, a carbonyl (e.g. an ester, a carboxyl, or a formyl), a thiocarbonyl (e.g. a thioester, a thiocarboxylate, or a thioformate), a ketone, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphate, a phosphinate, —(CH₂)ₘ—R₈, —(CH₂)ₘ—OH, —(CH₂)ₘ—O-lower alkyl, —(CH₂)ₘ—O-lower alkenyl, —(CH₂)ₘ—O—(CH₂)ₙ—R₈, —(CH₂)ₘ—SH, —(CH₂)ₘ—S-lower alkyl, —(CH₂)ₘ—S-lower alkenyl, —(CH₂)ₘ—S—(CH₂)ₙ—R₈, or protecting groups of the above or a solid or polymeric support; R₈ represents a substituted or unsubstituted aryl, aralkyl, cycloalkyl, cycloalkenyl, or heterocyclyl; and n and m are independently for each occurrence zero or an integer in the range of 1 to 6. P is preferably in the range of 0 to 5. For fused rings, wherein the number of substitution sites on the aryl group increases, p may be adjusted accordingly.

In certain embodiments, one or more of the substituents on the aryl group(s) can be a polypeptide, a nucleic acid, a carbohydrate or a lipid, for example, which may be useful in the development of biosensors.

For R and Y, conventional hydroxy, amino, thiol or seleno protecting groups which can be selectively removed to construct functionalized molecules may be used in accordance with standard practice (see, for example, Green, T. W. in *Protective Groups in Organic Synthesis*, John Wiley and Sons, 1981).

Examples of such amino protecting groups include, but are not limited to, groups such as Boc, Cbz, Alloc, or N-diphenylmethylene, or alternatively, the amine may be protected as an alkyl derivative such as N,N-dibenzyl or trityl. A typical reaction is the introduction of a Boc protecting group by treatment with di-t-butyl-dicarbonate (Boc anhydride). Buchwald (Wolfe, et al. *Tetrahedon Lett.* 1996, 38, 6367–6370) provides a simple general route to a wide range of primary arylamines by combining an activated aryl group and an imine group with a transition metal catalyst under conditions wherein the transition metal catalyst catalyzes the coupling of the aryl and imine groups through the imine nitrogen. The imine can then serve as a protected substitute for an activatable amine.

Suitable protecting groups for the hydroxyl functionality are stable under the conditions of the subsequent reaction sequence. This requirement is met by the trimethylacetyl group which can be removed by a nucleophile. Other suitable hydroxyl-protecting groups include acyl groups, alkoxycarbonyl groups, aryloxycarbonyl groups, carbamoyls, imidoyl groups, oxazolyl groups, sulfonyl groups, and (R₂₁)₃Si—, wherein each R₂₁ is independently selected lower alkyl groups (e.g. methyl, ethyl, isopropyl or t-butyl), e.g. t-butyldimethylsilyl ethers.

Suitable labile thiol protecting groups may be trityl, benzoyl, tetrahydropyran, benzyl, acetamidomethyl, p-methoxybenzyl, or the corresponding disulfide dimer or others well known in the art.

Reaction schemes A and B below illustrate the bidirectional approach of the subject method:

Scheme A

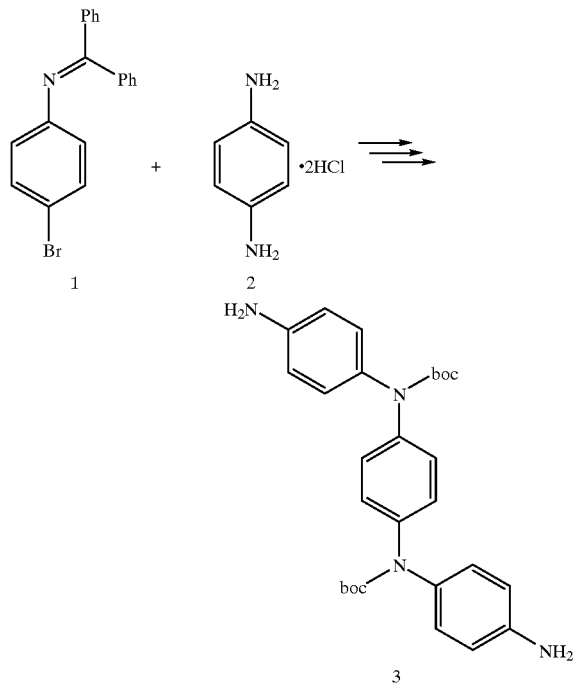

-continued

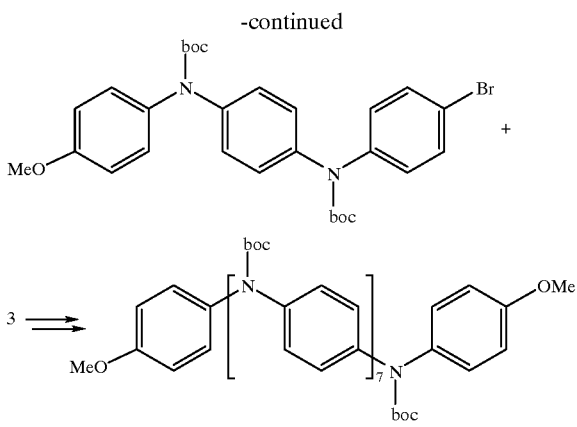

Scheme B

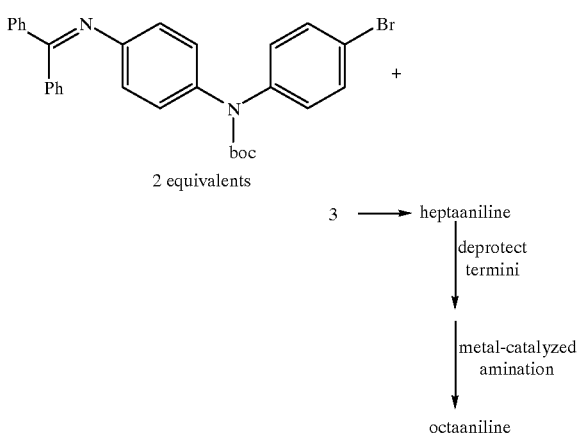

2 equivalents

3 ⟶ heptaaniline
↓ deprotect termini
↓ metal-catalyzed amination
octaaniline

The subject method provides a means for functionalizing (Br) termini of "growing" oligomers. The bidirectional synthesis permits the creation of products with high symmetry. The BOC groups, in the illustrated example, protect the oligoanilines from oxidation, and effect the solubility. Such protecting groups are readily removed by standard protocols.

However, in a preferred embodiment, a transition-metal (preferably Pd or Ni) catalyzed coupling is used. Exemplary forms of such reactions are described in U.S. Pat. No. 5,576,460, "Preparation of arylamines" and Guram et al. (1995) *Angew. Chem. Int.* 34:1348; and Wolfe et al. (1997) *J. Org. Chem.* 62:1264. Further examples of suitable metal-catalyzed reaction schemes are detailed below and in the examples. As suitable, the catalysts employed in the subject method involve the use of metals which can mediate cross-coupling of the aryl groups ArX and the amine or other functionality X, as defined above. In general, catalysts intended by the present invention can be characterized in terms of a number of features. For instance, the metal should be capable of activating the amine for attack on an electrophilic center of a substrate aryl.

In general, any transition metal (i.e. having d electrons) may be used to form the catalyst, e.g. a metal selected from one of Groups 3–12 of the periodic table or from the lanthanide series. However, in preferred embodiments, the metal will be selected from the group of late transition metals, e.g. preferably from Groups 5–12 and even more preferably Groups 7–11. For example, suitable metals include platinum, palladium, iron, nickel, ruthenium and rhodium. The particular form of the metal to be used in the reaction is selected to provide, under the reaction conditions, metal centers which are coordinatively unsaturated and not in their highest oxidation state. The metal core of the catalyst should be a zero-valent transition metal, such as Pd or Ni with ability to undergo oxidative addition to the Ar—X bond. The zero-valent state, $M^0$, may be generated in situ from $M^{+2}$.

Catalyst complexes may include chelating ligands, such as by way of example only, alkyl and aryl derivatives of phosphines and bisphosphines, imines, arsines, and hybrids thereof, including hybrids of phosphines with amines. Weakly nucleophilic or non-nucleophilic stabilizing ions are preferred to avoid complicating side reactions of the counterion, inter alia attack at or addition to the electrophilic center of the substrate aryl. Additionally, heterogeneous catalysts containing forms of these elements are also suitable catalysts for any of the transition metal catalyzed reactions of the present invention. Catalysts containing palladium and nickel are preferred. It is expected that these catalysts will perform comparably because they are known to undergo similar reactions, namely cross-coupling reactions, which may be involved in the formation of the arylamines of the present invention.

The coupling can be catalyzed by a palladium catalyst which may take the form of, to illustrate, $PdCl_2$, $Pd(OAc)_2$, $(CH_3CN)_2PdCl_2$, $Pd[P(C_6H_5)_3]_4$, and polymer-supported Pd(0) In other embodiments, the reaction can be catalyzed by a nickel catalyst, such as $Ni(acac)_2$, $NiCl_2[P(C_6H_5)_3]_2$, Raney nickel and the like, wherein "acac" represents acetylacetonate.

The active form of the transition metal catalyst is not well characterized. Therefore, it is contemplated that the "transition metal catalyst" of the present invention, as that term is used herein, shall include any transition metal catalyst and/or catalyst precursor as it is introduced into the reaction vessel and which is, if necessary, converted in situ into the active phase, as well as the active form of the catalyst which participates in the reaction. The transition metal catalyst is present in catalytic amounts relative to the substrate aryl, e.g. preferably in the range of 0.01 to 10 mole percent, and more preferably 1.0 to 2.5 mol %, with respect to the aromatic compound.

The catalyst will preferably be provided in the reaction mixture as metal-ligand complex comprising a bound supporting ligand, that is, a metal-supporting ligand complex. The ligand effects can be key to favoring, inter alia, the reductive elimination pathway or the like which produces the amino coupling. In particular, the use of bulky and less electron-donating ligands (but probably still chelating ligands) should favor the reductive elimination process. In preferred embodiments, the subject reaction employs bulky bidentate ligands such as bisphosphines.

The ligand, as described in greater detail below, may include chelating ligands, such as by way of example only, alkyl and aryl derivatives of phosphines and bisphosphines, imines, arsines, and hybrids thereof, including hybrids of phosphines with amines. Weakly nucleophilic or non-nucleophilic stabilizing ions are preferred to avoid complicating side reactions of the counter ion attacking or adding to the electrophilic center of the substrate aryl. This catalyst complex may include additional ligands as is necessary to obtain a stable complex. Moreover, the ligand can be added to the reaction mixture in the form of a metal complex, or added as a separate reagent relative to the addition of the metal.

In preferred embodiments of the subject method, the transition metal catalyst includes one or more phosphine ligands, e.g. as a Lewis basic co-catalyst that controls the stability and electron transfer properties of the transition metal catalyst, and/or stabilizes the metal intermediates. Phosphine ligands are commercially available or can be prepared by methods similar to known processes per se. The phosphines can be monodentate phosphine ligands, such as trimethylphosphine, triethylphosphine, tripropylphosphine, triisopropylphosphine, tributylphosphine, tricyclohexylphosphine, trimethyl phosphite, triethyl phosphite, tripropyl phosphite, triisopropyl phosphite, tributyl phosphite and tricyclohexyl phosphite, in particular triphenylphosphine, tri(o-tolyl)phosphine, triisopropylphosphine or tricyclohexylphosphine; or a bidentate phosphine ligand such as 2,2'-bis(diphenylphosphino)-1,1'-binaphthyl (BINAP), 1,2-bis(dimethylphosphino)ethane, 1,2-bis (diethylphosphino)ethane, 1,2-bis(dipropylphosphino) ethane, 1,2-bis(diisopropylphosphino)ethane, 1,2-bis (dibutylphosphino)ethane, 1,2-bis(dicyclohexylphosphino) ethane, 1,3-bis(dicyclohexylphosphino)propane, 1,3-bis (diiso-propylphosphino)propane, 1,4-bis (diisopropylphosphino)butane and 2,4-bis (dicyclohexylphosphino)pentane.

In preferred embodiments, the phosphine ligand is a triarylphosphine, e.g. P(o-tolyl)$_3$. Bis(phosphine) ligands are particularly preferred chelating supporting ligands. Suitable bis(phosphine) compounds include but are in no way limited to (±)-2,2'-bis(diphenylphosphino)-1,1'-binaphthyl (and separate enantiomers), (±)-2,2'-bis(di-p-tolylphosphino)-1,1'-binaphthyl (and separate enantiomers), 1-1'-bis (diphenylphosphino)ferrocene, 1,3-bis(diphenylphosphino) propane; 1,2-bis(diphenylphosphino)benzene, and 1,2-bis (diphenylphosphino)ethane. Hybrid chelating ligands such as (±)-N,N-dimethyl-1-[2-(diphenylphosphino)ferrocenyl] ethylamine (and separate enantiomers), and (±)-(R)-1-[(S)-2-(diphenylphosphino)ferrocenyl]ethyl methyl ether (and separate enantiomers) are also within the scope of the invention.

The ligand, if chiral, can be provided as a racemic mixture, a mixture enriched in one enantiomer, or a purified enantiomer.

The supporting ligand may be added to the reaction solution as a separate compound or it may be complexed to the metal center to form a metal-supporting ligand complex prior to its introduction into the reaction solution. Supporting ligands are compounds added to the reaction solution which are capable of binding to the catalyst metal center, although an actual metal-supporting ligand complex has not been identified in each and every synthesis. In some preferred embodiments, the supporting ligand is a chelating ligand. Although not bound by any theory of operation, it is hypothesized that the supporting ligands prevent unwanted side reactions as well as enhancing the rate and efficiency of the desired process. Additionally, they often aid in maintaining the solubility of the metal catalyst. Although the present invention does not require the formation of a metal-supporting ligand complex, such complexes have been shown to be consistent with the postulate that they are intermediates in these reactions and it has been observed that the selection of the supporting ligand has an effect on the course of the reaction.

The supporting ligand is present in the range of 0.0001 to 40 mol % relative to the limiting reagent, i.e. amine or aromatic compound. The ratio of the supporting ligand to catalyst complex is typically in the range of about 1 to 20, and preferably in the range of about 1 to 4 and most preferably about 2.4. These ratios are based upon a single metal complex and a single binding site ligand. In instances where the ligand contains additional binding sites (i.e. a chelating ligand) or the catalyst contains more than one metal atom, the ratio is adjusted accordingly. By way of example, the supporting ligand BINAP contains two coordinating phosphorus atoms and thus the ratio of BINAP to catalyst is adjusted downward to about 1 to 10, preferably to about 1 to 2, and most preferably to about 1.2. Conversely, Pd$_2$(dba)$_3$ contains two palladium metal centers and the ratio of ligand to Pd$_2$(dba)$_3$ is adjusted upward to 1 to 40, preferably to about 1 to 8, and most preferably to about 4.8.

In some instances, it may be necessary to include additional reagents in the reaction to promote reactivity of either the transition metal catalyst or activated aryl nucleus. In particular, it may be advantageous to include a suitable base such as, for example: an alkoxide such as sodium tert-butoxide, an alkali metal amide such as sodium amide, lithium diisopropylamide or an alkali metal bis(trialkylsilyl) amides, e.g. such as lithium bis(trimethylsilyl)amide or sodium bis(trimethylsilyl)amide, a tertiary amine (e.g. triethylamine, trimethylamine, N,N-dimethylaminopyridine, 1,5-diazabicycl[4.3.0]non-5-ene (DBN), 1,5-diazabicycl [5.4.0]undec-5-ene (DBU), alkali, alkaline earth carbonate, bicarbonate or hydroxide (e.g. sodium, magnesium, calcium, barium, potassium carbonate, hydroxide, and bicarbonate). Preferred bases include Cs$_2$CO$_3$ and DBU.

As further illustration, the appended examples describe that the palladium-catalyzed amination of aryl halides can be applied to the synthesis of octaanilines utilizing a bi-directional assembly strategy. The materials are prepared in four isolated steps which proceed in good yield. Oligoanilines of other chain lengths may be prepared by appending different side chains to a symmetrical core building block. The synthesis of oligoanilines with functionalized terminal aryl groups is accomplished in a facile manner.

The subject method greatly expands the repertoire of techniques available for constructing oligoanilines and their analogs. Some of its applications include use as components in rechargeable batteries (MacDiarmid, A. G.; Mu, S.-L.; Somasiri, M. L. D.; Wu., W. *Mol. Cryst. Liq. Cryst.* 1985, 121, 187), electrochromic displays (Baughman, R.; Schacklette, L. W. In *Science and Applications of Conducting Polymers*, Salaneck, W. R.; Clark, D. T.; Samuelsen, E. J. Ed.; IOP Publishing LTD.: Bristol, U. K., 1990; p 47), electromechanical actuators (Kaneto, K.; Kaneko, M.; Min. Y.; MacDiarmid, A. G. *Synth. Met.* 1995, 71, 2211), anti-corrosion coatings for steel ((a) DeBerry, D. W. *J. Electrochem. Soc.* 1985, 132, 1022. (b) Ahmad, N.; MacDiarmid, A. G. *Synth. Met.* 1996, 78, 103. (c) Wessling, B. *Adv. Mater.* 1994, 6, 226. (d) Elsenbaumer, R. L.; Wessling, B. *Synth. Met.* 1995, 71, 2163), and electromagnetic interference shielding ((a) Colaneri, N. F.; Shacklette, L. W. *IEEE Trans. Instrum. Meas.* 1992, IM-41, 291. (b) Taka, T. *Synth, Met.* 1991, 41–43, 1177. (c) Joo, J.; Epstein, A. *J. Appl. Phys. Lett.* 1994, 65, 2278).

Definitions

For convenience, before further description of the present invention, certain terms employed in the specification, examples, and appended claims are collected here.

The term "substrate aryl group" refers to an aryl group containing an electrophilic atom which is susceptible to the subject cross-coupling reaction, e.g. the electrophilic atom bears a activated group. In the present invention, the substrate aryl is represented by ArX, where X is the activated group. The aryl group, Ar, is said to be substituted if, in addition to X, it is substituted at yet other positions. The substrate aryl group can be a single ring molecule, or can be a substituent of a larger molecule.

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above. Electrophilic moieties useful in the method of the present invention include halides and sulfonates.

The terms "electrophilic atom", "electrophilic center" and "reactive center" as used herein refer to the atom of the substrate aryl moiety which is attacked by, and forms a new bond to, the heteroatomic nucleophile. In most (but not all) cases, this will also be the aryl ring atom from which the leaving group departs.

The term "electron-withdrawing group" is recognized in the art, and denotes the tendency of a substituent to attract valence electrons from neighboring atoms, i.e. the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, —CN, chloride, and the like. Exemplary electron-donating groups include amino, methoxy, and the like.

The term "reaction product" means a compound which results from the reaction of the amine and the substrate aryl group. In general, the term "reaction product" will be used herein to refer to a stable, isolable adduct, and not to unstable intermediates or transition states.

The term "catalytic amount" is recognized in the art and means a substoichiometric amount of a reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g. $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g. an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhlydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g. the other cyclic rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms, as valence and stability permit. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphate, phosphinate, carbonyl, carboxyl, silyl, ether, alkylthio, sulfonyl, sulfate, ketone, aldehyde, ester, a heterocyclyl, an aromatic or heteroaromatic moiety, —$CF_3$, —CN, or the like.

The terms "polycyclyl" or "polycyclic group" refer to two or more rings (e.g. cycloalkyls, cycloalkenyls, cycloalkynyls, aryls and/or heterocyclyls) in which two or more carbons are common to two adjoining rings, e.g. the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur, selenium, and phosphorous.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The phrases "protecting group" and "protective group" as used herein mean temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g. a moiety that can be represented by the general formula:

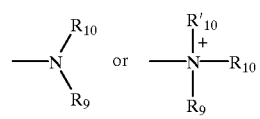

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g. $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e. at least one of $R_9$ and $R_{10}$ is an alkyl group.

The term "acylamino" is art-recognized and refers to a moiety that can be represented by the general formula:

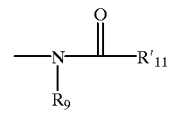

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art-recognized as an amino-substituted carbonyl and includes a moiety that can be represented by the general formula:

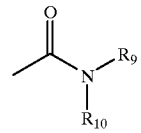

wherein $R_9$, $R_{10}$ are as defined above. Preferred embodiments of the amide will not include imides, which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are as defined above. Representative alkylthio groups include methylthio, ethylthio, and the like.

The term "carbonyl" is art-recognized and includes such moieties as can be represented by the general formula:

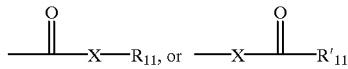

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" or "formyl" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy (or t-butoxy) and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art-recognized and includes a moiety that can be represented by the general formula:

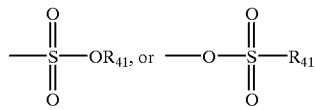

in which $R_{41}$ is an electron pair, hydrogen, or substituted or unsubstituted alkyl, cycloalkyl, or aryl.

The term "sulfate" is art-recognized and includes a moiety that can be represented by the general formula:

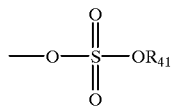

in which $R_{41}$ is as defined above.

The term "sulfonamido" is art recognized and includes a moiety that can be represented by the general formula:

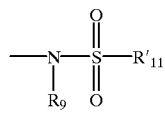

in which $R_9$ and $R'_{11}$ are as defined above.

The term "sulfamoyl" is art-recognized and includes a moiety that can be represented by the general formula:

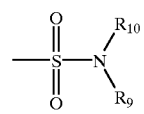

in which $R_9$ and $R_{10}$ are as defined above.

The terms "sulfoxido" or "sulfinyl", as used herein, refers to a moiety that can be represented by the general formula:

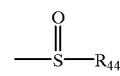

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

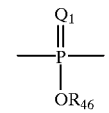

wherein $Q_1$ represented S or O, and $R_{46}$ represents hydrogen, a lower alkyl or an aryl. When used to substitute, for example, an alkyl, the phosphoryl group of the phosphorylalkyl can be represented by the general formula:

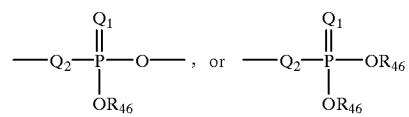

wherein $Q_1$ represented S or O, each $R_{46}$ independently represents hydrogen, a lower alkyl, or an aryl, and $Q_2$ represents O, S, N, or a bond. When $Q_1$ is an S, the phosphoryl moiety is a "phosphorothioate".

A "phosphoramidite" can be represented in the general formula:

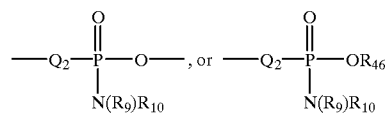

wherein $R_9$ and $R_{10}$ are as defined above, and $Q_2$ represents O, S, or N.

A "phosphonamidite" can be represented in the general formula:

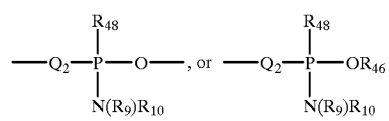

wherein $R_9$ and $R_{10}$ are as defined above, $Q_2$ represents O, S or N, $R_{48}$ represents a lower alkyl or an aryl, and $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_8$, m and $R_8$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

It will be understood that "substitution" or "substituted with" includes the implicit proviso that such substitution is in accordance with permitted valence of the substituted atom and the substituent, and that the substitution results in a stable compound, e.g. which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

A "polar solvent" means a solvent which has a dipole moment ($\epsilon$) of 2.9 or greater, such as DMF, THF, ethylene gylcol dimethyl ether, DMSO, acetone, acetonitrile, methanol, ethanol, isopropanol, n-propanol, t-butanol or 2-methoxyethyl ether. Preferred solvents are DMF, diglyme, and acetonitrile.

An "aprotic solvent" means a non-nucleophilic solvent, incapable of serving as a hydrogen-bond donor, having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, ITF or DMSO.

A "polar, aprotic solvent" means a polar solvent as defined above which has no available hydrogens to exchange with the compounds of this invention during reaction, for example DMF, acetonitrile, diglyme, DMSO, or THF.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Applications

Conducting polymers in general lend themselves to a wide range of applications, and the ease with which substituted oligo- and polyanilines, as well as related oligo- and polymers, may be synthesized according to the present invention opens the possibility of synthesizing conducting molecules tailored to specific applications.

For example, it is known that placing ortho-substituents on polyaniline leads to a decrease in conductivity, presumably by distorting the polymer chain from the planar arrangement most conducive to conductivity (D'Aprano, G.; LeClerc, M. *Chem. Mater.* 1995, 7, 33). In the case of oligoanilines, this hypothesis suggests that distortions placed near the end of the chain, which would leave most of the chain undistorted, will decrease conductivity less than distortions near the center, which would leave only much shorter fragments undistorted. In this manner, the conductivity of the sample could be tuned to specific applications. Materials with a conductivity less than $10^{-15}$/ohm are considered insulators. Materials with a conductivity in the range of $10^{-9}$ to $10^{-6}$/ohm find uses as anti-static agents. Materials with a conductivity between $10^{-6}$ and $10^{-2}$/ohm find applications as electromagnetic interference shields. Materials with a conductivity near that of silicon, 1/ohm, might find uses as semiconductors, while materials with higher conductivities can be used as conductors.

Incorporation of different aryl groups, including heterocyles such as carbazoles and pyrroles among others, can be expected to modify the redox potential and conductivity of the resultant material. Similar effects may be achieved merely by introducing substitutents onto the aryl rings. The introduction of acidic residues (e.g. carboxylic or sulfonic acids) directly onto the polymer may further obviate the need for external doping with protic acid, a common method for increasing the conductivity of polyaniline. The introduction of Lewis-basic moieties, such as amines, imines, and phosphines, may facilitate doping of the organic compound with metals to further alter its properties. Such doping might affect intermolecular interactions by favoring chelation between strands, resulting in a more ordered material. The inclusion of polyaromatic aryl moieties and/or an array of hydrogen-bonding functionalities might also affect the conductivity by changing the crystallinity of the material and other intermolecular interactions.

It might be possible to expand the conducting range of such polymers by including both electron-rich and electron-poor subunits, with the aim of lowering the first oxidation potential and raising the second oxidation potential, respectively. Such a compound is depicted below.

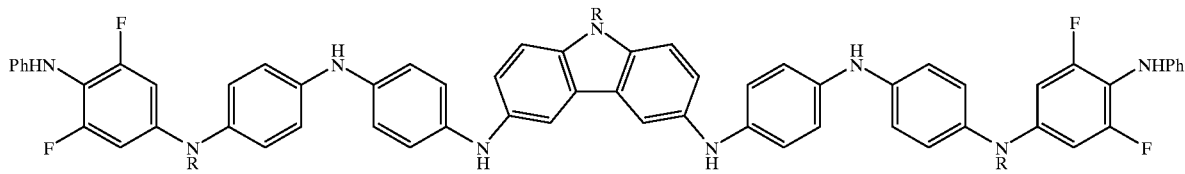

In one embodiment, the conducting oligomer candidates can be tested as molecular wires to link metal clusters in self-assembled monolayers. The construction of planar metal cluster arrays coupled by semiconductors or metallic conductors has been proposed as a model for designing nanoscale digital circuits (Tucker, J. R.; *J. Appl. Phys.* 1992, 71, 4399; Korotkov, A. N.; Chen, R. H.; Likharev, K. J. *Appl. Phys.* 1995, 78, 2520).

Ion sensors may be constructed by introducing a ligand for recognition of the metal into the polymer backbone. Alternatively, tethered attachment of similar ligands may also be used to affect conductivity. Examples of such ion-sensing polymers are shown in Scheme 21 (below). Such detection is expected to be quite sensitive, as conductivity is an easily measured bulk property and doping of polyanilines has a profound effect on conductivity.

Organic molecules may be detected with similar systems in which the organic substrate is expected to displace metal atoms from a doped polymer. As ethylenediamine has been shown to displace copper from polyrotaxanes, macrocyclic structures resembling crown ethers, (Zhu, S. S.; Carroll, P. J.; Swager, T. M. *J. Am. Chem. Soc.*, 1996, 118, 8713), cyanide ions might be expected to displace copper (Sharpe, A. G. In *The Chemistry of the Cyano Complexes of the Transition Metals*; Academic Press: London, 1976, pp. 265–272) from a suitably-constructed polyaniline as exemplified in Scheme 23 (below).

Figure 2:
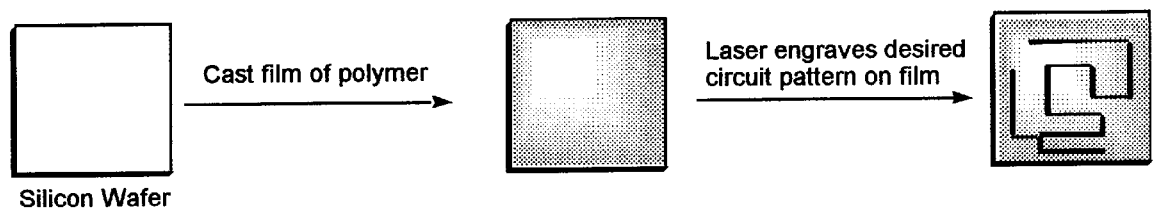
FIG. 2. Scheme 25. Process for producing digital circuits from a conducting organic polymer with photolabile protecting groups.

By preparing polyanilines with photolabile protecting groups (Pillai, V. N. R. *Synthesis*, 1980, 1; Amit, B.; Zehavi, U.; Patchornik, A. *J. Org. Chem.* 1974, 39, 192) in place of t-butyl carbamates, it should be possible to prepare a sample of protected polyaniline which can be rendered conducting only when and where it is exposed to light suitable to remove the protecting groups. With such a film deposited on a silicon wafer, a laser could be used to deprotect certain regions of the polyaniline which would then function as conducting wires. The deprotected regions could then be doped to function as digital circuits while the still-protected regions remain insulating. Levels of complexity may be introduced by casting layers of films, each layer comprising a polymer with protecting groups that can be removed independently of protecting groups in the other layers, by using protecting groups tuned to be deprotected at different wavelengths, for example. Other means of differentiation include using protecting groups labile to alternative methods of removal, such as thermolysis, acid, or base. Such systems could be used to replace conventional photoresists and conductors in silicon wafer technology. An exemplary system is depicted in FIG. 2.

It has been demonstrated that plastic joints may be welded together with selective heating at the contact points through the combined use of polyanilines and thermoplastics (such as high-density polyethylene) (Epstein, A. J.; Joo, J.; Wu, C.-Y.; Benatar, A.; Faisst, C. F.; Zegarski, J.; MacDiarmid, A. G. In *Intrinsically Conducting Polymers: An Emerging Technology*, Aldissi, M. Ed.; Kluwer Academic Publishers: Netherlands, 1993, p 165). The absorption of microwave radiation by the polyaniline results in heat evolution, melting the thermoplastic. Cooling of the blended polyaniline and thermoplastic causes fusing of the joined materials. The process may be reversed by reexposure to microwaves.

Materials with combined thermoplastic and conductive properties might be designed by the preparation of oligoaniline-polyurethane block copolymers as shown in Scheme 26 (below). The materials could be prepared by from a diisocyanate-capped oligomer, which could then be copolymerized with hydrocarbon chains terminated with diols and diisocyanates. The benefit of uniting both thermoplastic and conductive properties in a single polymer is that the even blending of the two components, by nature of the very material, should result in even more coherent heating and melting. The properties of the polyurethane can be modulated by choice of diol and diisocyanate (Calport, D.; Janes, W. H. In *Block Copolymers*; Applied Science Publishers, Ltd.: London, 1973; p 224). In addition, the microwave-absorbing properties of the aromatic region might be altered by incorporating polyaromatic units (e.g. acridone or carbazole).

DeBerry discovered in 1985 that polyaniline deposited on a steel surface provided protection against corrosion. The mechanism of protection was determined to be anodic in nature, such that the doped polyaniline stabilized a passive metal oxide coating from dissolution and reduction. Derivatives of oligo- and polyanilines synthesized by our invention could be prepared to maximize adherence to the metal surface and electrochemical properties beneficial to passivation of the metal surface.

Exemplary Catalyzed Reactions

In an illustrative embodiment, the subject method employs the palladium-catalyzed carbon-nitrogen bond formation reaction to construct a polyaniline framework, and an orthogonal protecting group scheme to control the reactions. The protecting groups confer excellent solubility properties upon the oligomers, which may be processed as solubilized derivatives before conversion to their electroactive forms.

Synthetic Equivalents of 4-Bromoaniline

The simplest palladium-catalyzed synthesis of polyaniline would involve the polymerization of 4-bromoaniline. However, the coupling products would be easily oxidized, even short oligomers would present solubility problems, and precise control over chain length would be difficult. We have devised synthetic equivalents of 4-bromoaniline in which either the arylamine or the aryl bromide is masked. Condensation of 4-bromoaniline with benzophenone is easily carried out on large scale, affording crystalline N-diphenylmethylene-4-bromoaniline in high yield. This aryl bromide is not only a highly active substrate for palladium-catalyzed aryl amination, but a convenient precursor to 4-trimethylsilylaniline, in which the trimethylsilyl group is easily replaced by bromine.

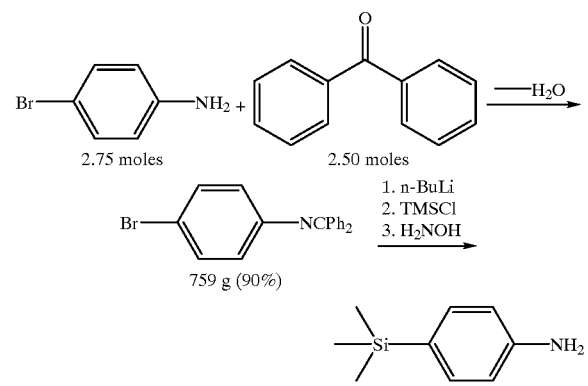

Scheme 1. Preparation of 4-bromoaniline equivalents: aryl bromide and aryl amine.

Divergent-Convergent Synthesis of Oligoanilines

Palladium-catalyzed coupling of 4-trimethylsilylaniline with N-diphenylmethylene-4-bromoaniline affords an aniline dimer with a masked bromide at one end and a protected amine at the other. Protection of the internal NH group as its tert-butoxycarbamate (BOC) derivative allows the selective replacement of the trimethylsilyl group with bromine, or the cleavage of the imine to give an air-stable, soluble arylamine. Thus, the protected dimer is divided into two portions: one is converted to an aryl bromide, and the other to an arylamine. Palladium-catalyzed coupling followed by BOC-protection affords the analogously protected tetraaniline, and the sequence may be repeated as desired. The divergent-convergent synthesis is shown in Scheme 2.

Scheme 2
Divergent-convergent synthesis of protected oligoanilines.

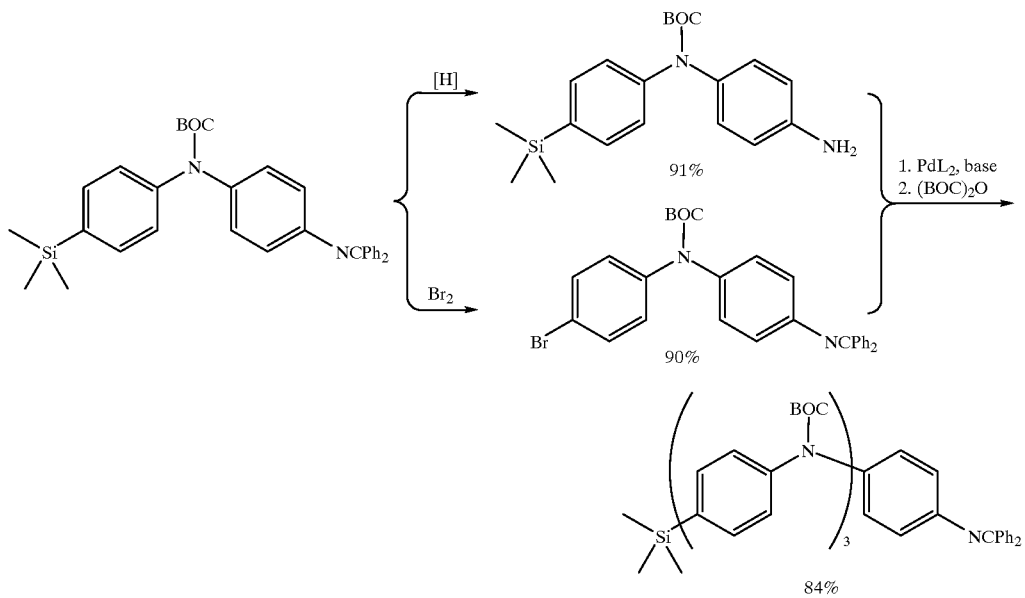

The process is easily carried out on multigram scale. The yield for each step is high, and the intermediates are crystalline, soluble, and easily purified by recrystallization. The divergent-convergent route has been used to prepare protected dimer through decamer, 16- mer and 24-mer.

Convergent Synthesis of Symmetric Oligomers

For electrochemical studies and applications of oligoanilines, symmetric products are desirable, to avoid the complications of parallel and antiparallel orientations between chains. Two aryl bromides prepared by the divergent-convergent route may be coupled with a symmetric diamine (or the converse) to form a symmetric oligomer, more than doubling the chain length. This convergent step forms the basis of a rapid synthesis of a variety of end-functionalized octamers, as shown in Scheme 3.

Scheme 3
Convergent preparation of symmetric, functionalized octamers.

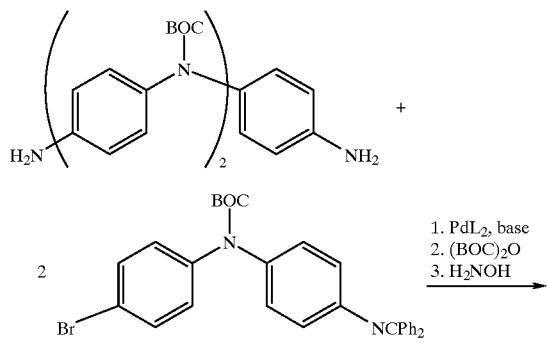

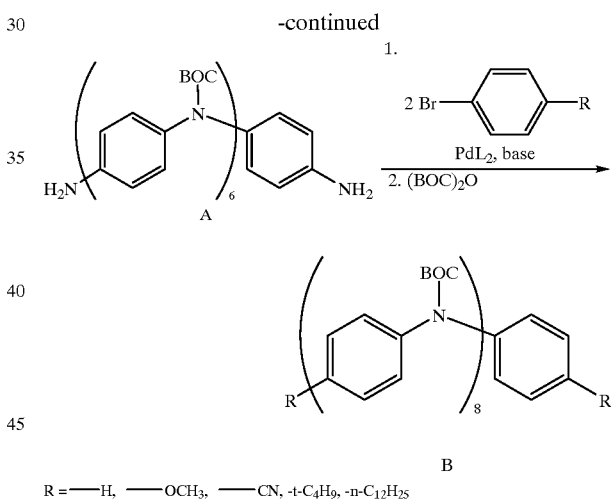

$R = $ —H, —$OCH_3$, —CN, -t-$C_4H_9$, -n-$C_{12}H_{25}$

As in the divergent-convergent synthesis, yields for each step are high. While the intermediates are crystalline and easily purified, isolation is not necessary at every stage. The symmetric $N_8$-diamine A has been prepared on 10-gram scale, and may be coupled in good yield with a wide variety of bromoarenes to give end-capped octamers B. The reaction of anilines with dibromides has been employed in the synthesis of symmetric, capped heptamer, nonamer, decamer, and 18-mer.

We have prepared the symmetric core pieces as dibromides and as diamines, with odd or even numbers of nitrogen atoms. The coupling of 1,4-phenylenediamine with two equivalents of N-diphenylmethylene-4-bromoaniline, followed by in situ BOC-protection and imine cleavage, affords a symmetric $N_4$-diamine as shown in Scheme 4.

Scheme 4
Synthesis of an even-numbered α,ω-diamine.

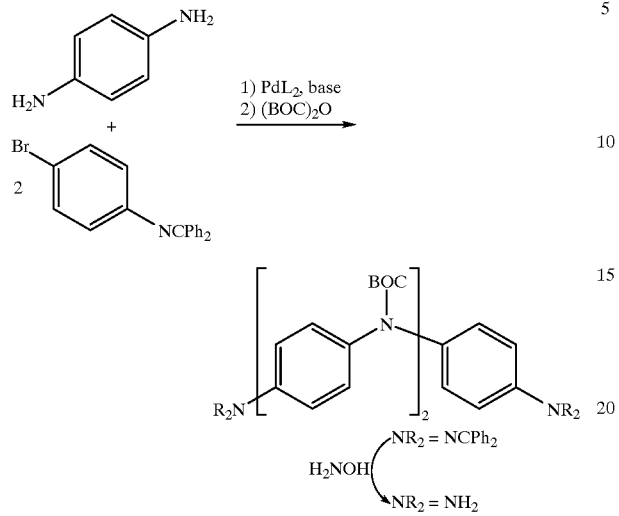

Alternatively, a dibromide with two nitrogen atoms may be prepared by the reaction of 1,4-phenylenediamine with two equivalents of 1,4-dibromobenzene. Polymerization does not occur because the product, a highly electron-rich aryl bromide, reacts with the palladium catalyst far less rapidly than does 1,4-dibromobenzene. Protection of the internal NH groups, carried out in situ, prevents air oxidation, and activates the carbon-bromine bonds toward oxidative addition to palladium. The sequence is shown in Scheme 5.

Scheme 5
Synthesis of an even-numbered α,ω-dibromide.

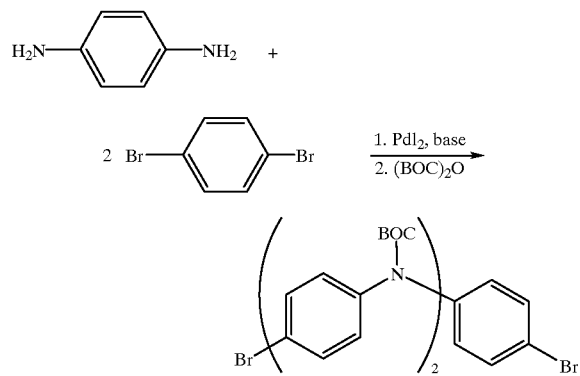

Odd-numbered core pieces are prepared readily as well. Regioselective para-bromination of diphenylamine affords 4,4'-dibromodiphenylamine, and BOC-protection converts this to an active substrate for aryl amination, as shown in Scheme 6.

Scheme 6
Synthesis of an odd-numbered α,ω-dibromide.

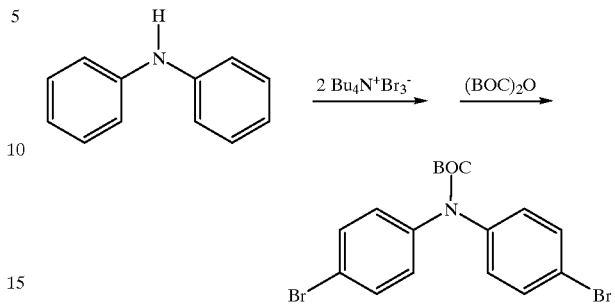

The corresponding diamine may be prepared by the coupling of the dibromide with two equivalents of commercially available benzophenone imine, followed by imine cleavage (Scheme 7). Benzophenone imine thus serves as a convenient synthetic equivalent of ammonia, in a reaction which was later expanded to a general method for the conversion of aryl chlorides, bromides, iodides, and triflates to primary anilines (Wolfe, J. P.; Åhman, J.; Sadighi, J. P.; Singer, R. A.; Buchwald, S. L. *Tetrahedron Lett.* 1997, 38, 6367–6370).

Scheme 7
Synthesis of an odd-numbered α,ω-diamine.

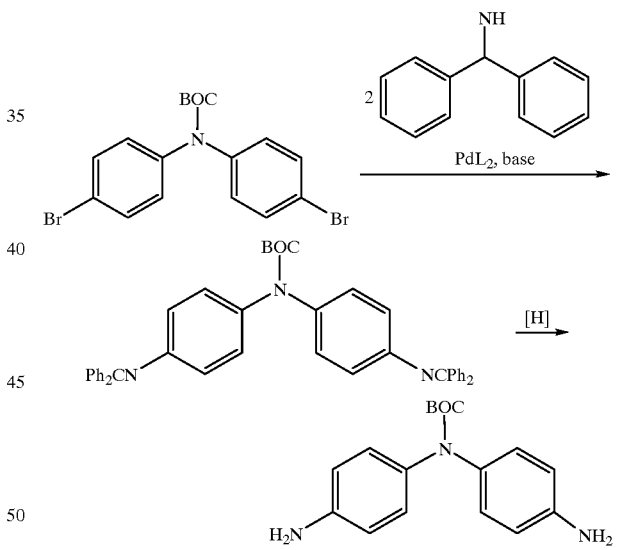

Oligoaniline Deprotection

The protected oligoanilines are soluble in common organic solvents, but non-electroactive; conversely, the deprotected forms are electroactive but exhibit generally poor solubility. The BOC groups may be removed cleanly and quantitatively (as judged by infrared and $^1$H NMR spectroscopy) by thermolysis, affording the fully reduced form of the oligomer as shown in Scheme 8. For longer oligoanilines this form is nearly insoluble in most common solvents, but sufficiently soluble in polar aprotic solvents such as N,N-dimethylformamide or N-methylpyrrolidinone to permit absorption spectroscopy, $^1$H NMR, and the casting of films for electrochemistry.

Scheme 8
Thermal deprotection of oligoanilines.

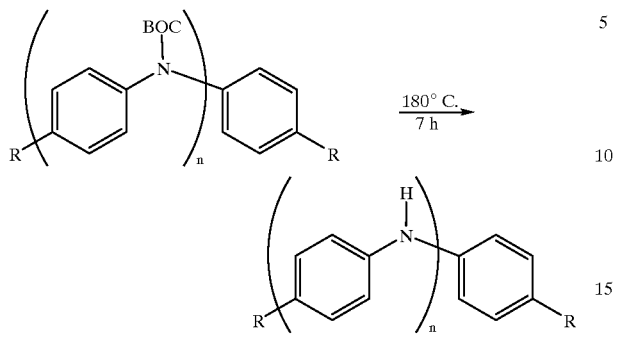

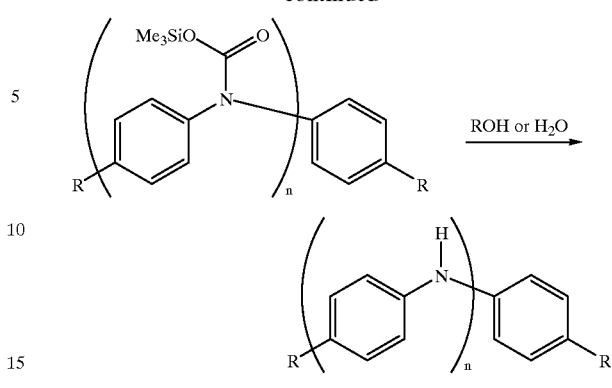

The BOC-protected oligomers react very rapidly with iodotrimethylsilane to form the corresponding trimethylsilyl carbamates. The trimethylsilyl carbamate group confers the same solubility as the tert-butyl carbamate, but is extremely labile in the presence of moisture or protic solvents. Films of the TMS carbamate-protected oligomers may be prepared from volatile solvents such as dichloromethane and subsequently deprotected by exposure to water or alcohols. The deprotection with iodotrimethylsilane is illustrated in Scheme 9.

Scheme 9
Iodotrimethylsilane-mediated deprotection of oligoanilines.

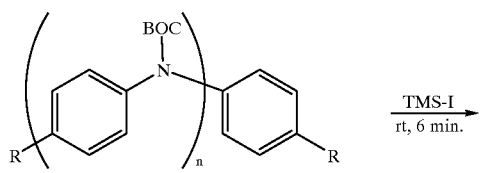

Electrochemical Studies

Cyclic voltammetry of the deprotected oligomers allows the observation of three oxidation states, consistent with previous studies of polyaniiine and phenyl-capped octaaniline. These oxidation states are depicted in Scheme 10. In the fully reduced form, referred to as leucoemeraldine, every nitrogen bears a lone pair, and all arene rings are in the benzenoid form. The emeraldine oxidation state consists of quinonediimine moieties alternating with phenylenediamine moieties, and may be represented as a repeating semiquinone radical cation. In the pernigraniline form, every phenylenediamine moiety has been oxidized to its quinoid form. Electrochemical studies of oligoanilines according to the present invention are presented in Example 2.

Scheme 10
Principal oxidation states of oligoanilines.

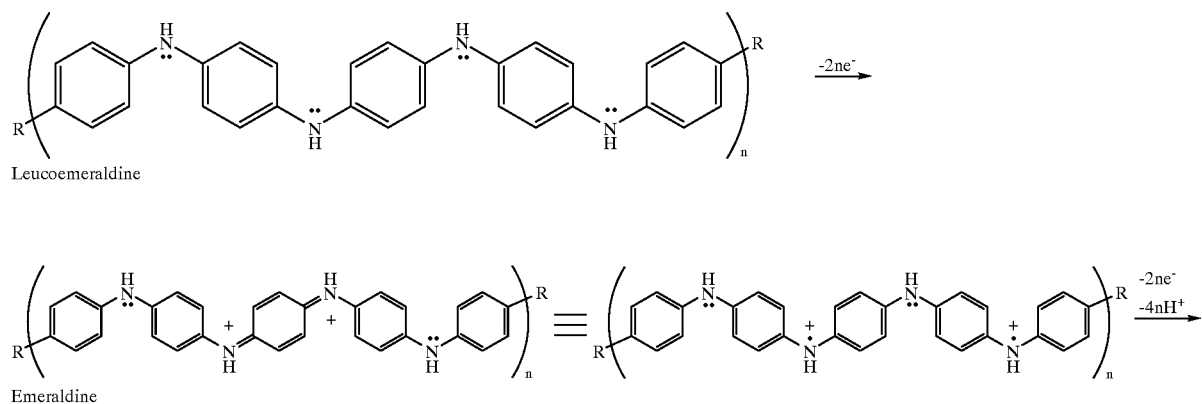

Leucoemeraldine

Emeraldine

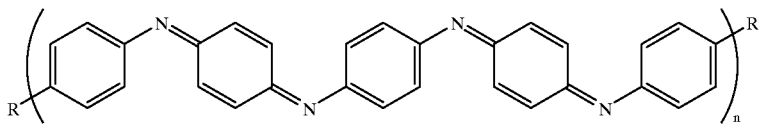

Pernigraniline

Palladium-Catalyzed Polymerization

The divergent-convergent strategy has been modified to provide an aniline dimer containing both an aryl bromide and an arylamine; polymerization of this followed by BOC-protection afforded a polymer sufficiently soluble in chlorinated solvents to permit $^1$H and $^{13}$C NMR spectroscopy and gel permeation chromatography. The sequence is shown in scheme 11.

Scheme 11
Synthesis of protected polyaniline using palladium catalysis.

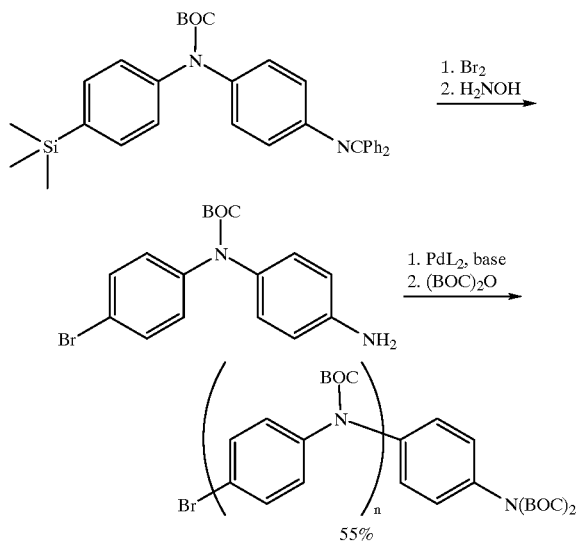

Preliminary results show that chain lengths comparable to those of bulk polyaniline are obtained by this method. Gel permeation chromatography indicates a weight-average molecular weight of 45,300, and a number-average molecular weight of 11,400; the latter corresponds to an average chain length of approximately sixty aniline units, or a degree of polymerization (n) of 30. The polymer shows a remarkably clean 1H NMR spectrum, consisting of a single aryl resonance and a single tert-butyl resonance; no peaks attributable to endgroups are discernible. Further studies of this process, aimed at achieving higher and narrower molecular weight ranges, are in progress. The polydispersity, an index of molecular weight distribution, was calculated as 4.0, versus 9.0 for the conventionally prepared material,[2] the relatively narrow product distribution suggests a solubility-controlled process.

Our synthetic approaches for preparing oligoanilines and polyanilines should lead to practical preparations of a wide range of functionalized derivatives since the methods of assembly (Pd-catalyzed amination reactions) have a high level of functional group tolerance. For applications such as conducting polymers, phenyl-capped octaaniline has previously been shown to serve as a substitute for bulk polyaniline, having similar conductivity and absorption properties. lob The oligomers which we can prepare have several advantages over conventionally prepared (electropolymerized) polyaniline. First, they can be selectively end group functionalized, allowing "tuning" of properties. Second, they can be prepared in monodisperse form with well-defined (and variable at will) chain lengths. Furthermore, "designer" oligomers should be preparable in inherently soluble forms (once deprotected), and due to their homogeneity in composition, result in materials of higher crystallinity and conductivity. Polyanilines prepared via the Pd-catalyzed amination method have an advantage due to their ease of synthesis, while allowing one to obtain extended conjugated systems with useful levels of polydispersity. Of significance is that the materials which we have prepared are very soluble due to the t-butylcarbamate groups (BOC), which make them amenable to processing and prevent their premature oxidation. These carbamate protecting groups can be cleaved either thermally or chemically to liberate the polyaniline or oligoaniline free base (in the leucoemeraldine state).

It is easy to see that the scope of the subject methodology can be readily expanded to include the preparation of conjugated oligomers and polymers derived from functionalized building blocks. Using our synthetic strategies, one can construct novel materials which may be models for application to anticorrosion coatings for metals, conductors in electronic devices, ion sensors, and welding of plastic joints. In addition, the subject method can contribute to the understanding of conducting organic materials and their transport processes through characterization (X-ray crystal structures, ESR, UV, IR, NMR) of our designer oligomers. These studies are outlined below in more detail.

Design of Novel Conducting Oligomers

The subject method can be used to determine structure-property relationships of our oligomers to gain insight into the rational design of such materials. Because our oligomers are prepared in a controlled, stepwise fashion (as described earlier), we can introduce substituents at virtually any location and as frequently as desired throughout the backbone.

We will continue to exploit end group functionalization of the octaanilines. This handle offers the opportunity of introducing substituents for improving intermolecular interactions and solubility. A variety of useful end groups that could be implemented are shown below in Table 2. The oligomer terminated with tributylstannane allows the appending of aryl, vinyl, allyl, or acyl moieties via Stille couplings, as well as attachment to a similarly functionalized oligomer (or polymer) backbone. This system would provide a diverse family of terminally functionalized oligomers from a single precursor. Carbonyl and sulfonate end groups should enhance hydrogen-bonding (Pimentel, G. C.; McClellan, A. L. Annu. Rev. Phys. Chem. 1971, 22, 347) which may aid in organization of oligomer chains. Placing appropriate donors on the ends of oligomers should promote metal binding. A metal bound to multiple oligomers could serve as a template for arranging other chains. In addition, metal crosslinking of oligoanilines may facilitate interchain electron transfer.

TABLE 2

Various end groups for oligomers and their applications.

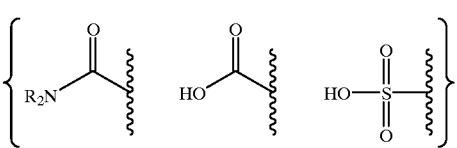

| End Group | Application |
|---|---|
| Bu$_3$Sn | Append substituent via Stille coupling |
| 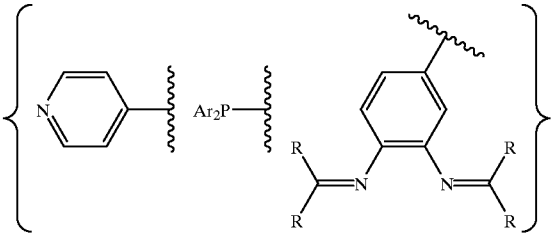 | H-Bonding interactions |
| | Metal binding |

Aside from preparing octaaniline derivatives with end group variation, our synthetic approach (shown in Schemes 3 and 4) should be amenable to making changes to the internal segments. By inserting one or two aromatic groups with substituents in the oligomers, we can probe the influences of various functional groups. Shown below are several groups that may be introduced in the octamers at one site (i.e. replacement for phenylenediamine core) or at two symmetrically located sites. As a result we can probe not only the effects of a given substituent, but also their variation with respect to location in the oligomer. Segments may be substituted to alter redox properties (electron-donating and -withdrawing groups), and solubility. Incorporation of fluorinated arenes should raise the oxidation potentials without significant changes to sterics, while the other groups shown should impair the planar geometry required for optimal conductivity. Placing ortho-substituents on polyaniline leads to significant distortion of the chain from planarity as has been previously observed by the decrease in conductivity (D'Aprano, G.; Leclerc, M. *Chem. Mater.* 1995, 7, 33). It is likely that substituents which perturb the oligomer geometry have a lessened level of deleterious effects on conductivity at positions 3 and 4 (as in Scheme 12) versus positions 1 and 2 since a larger percentage of the system will remain in conjugation.

Scheme 12
Internal segments to be inserted into octaaniline framework to probe effects of Symmetrical construction of an octamer (Schemes 3 and 4) results in symmetrical positions for substitutions.

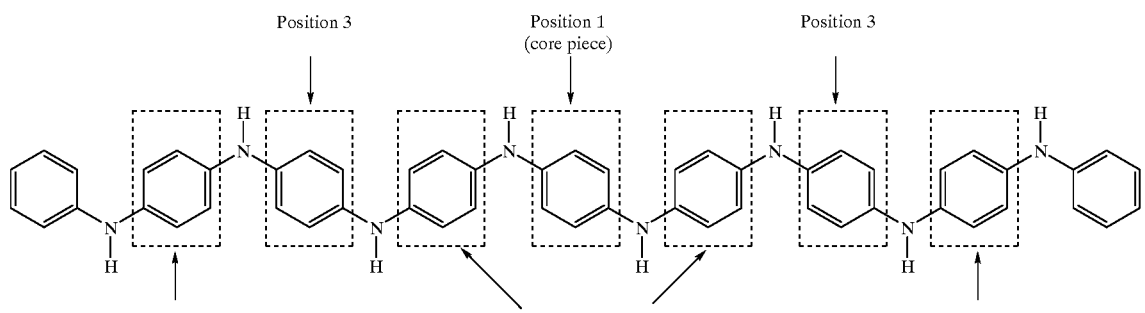

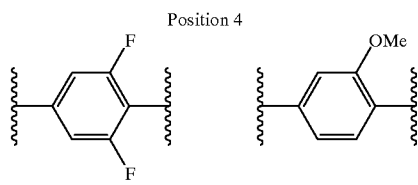
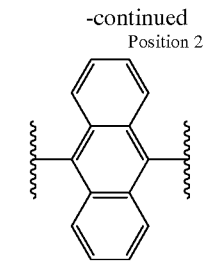
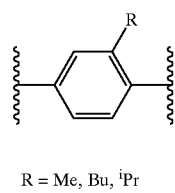

R = Me, Bu, $^i$Pr

It may be desirable to introduce electron-rich heterocycles, such as thiophenes and pyrroles, in the oligomer to modify redox potential and conductivity. However, early attempts to couple thiophene and pyrrole (with the nitrogen unprotected) derivatives via Pd-catalyzed amination have proven difficult. Couplings with pyrroles can most likely be carried out effectively with the current Pd catalyst system by protecting the nitrogen (as an amide). However, we still may need to optimize the Pd catalyst further to be able to utilize thiophenes in the preparation of oligomers and copolymers.

By adapting our synthetic methods to include polyaromatic building blocks, the electronic properties, solubility and crystallinity of the materials can be modified on internal segments of the oligomers without compromising the planar geometry. The polyaromatic groups shown below (Scheme 13) should adjust the electronics (and solubility in some cases) when inserted in the oligomers in place of a phenyl group at any one of the four possible positions without disrupting the conjugation. Utilizing the polyaromatics at one or more positions may improve conductivity significantly due to better organization of chains in the oligoaniline analogues which would be a result of enhanced π-stacking, additional hydrogen-bonding (due to carbonyl and amine moieties), and dipole-dipole interactions (Isaacs, N. S. In *Physical Organic Chemistry*; John Wiley and Sons, Inc.: New York, 1987; pp.46–70).

Scheme 13
Polyaromatic building blocks which may be substituted at any one or all of the 4 positions in an octamer.

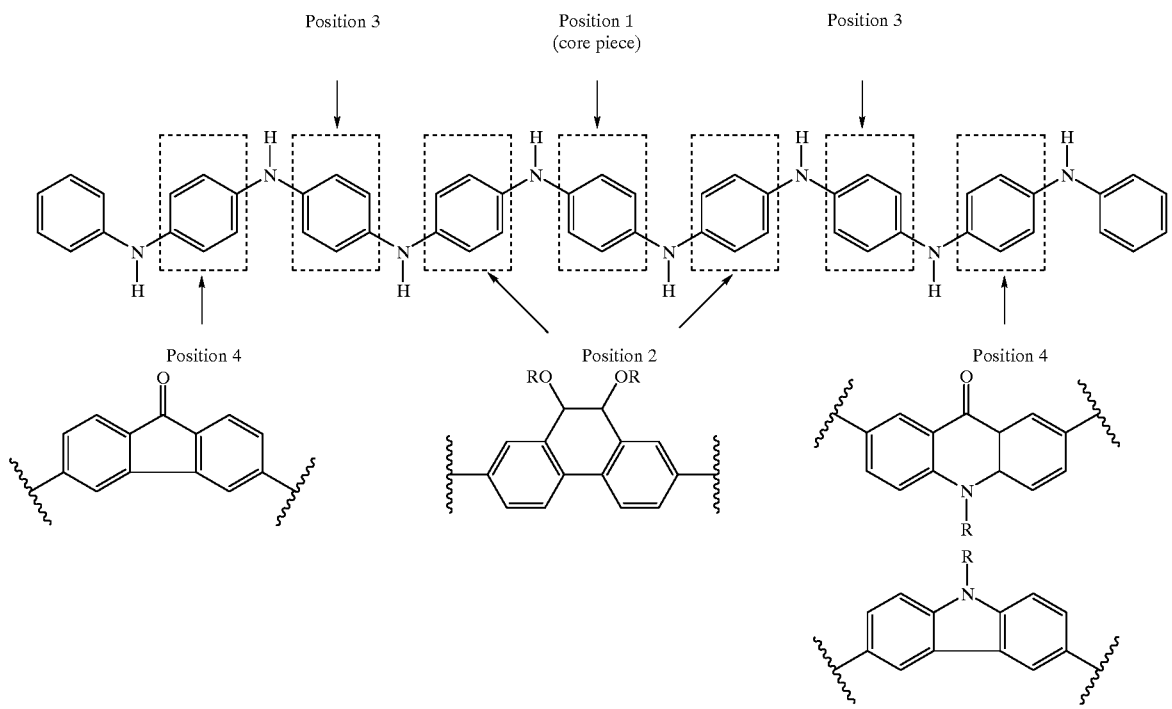

Oligoaniline analogues containing blends of electron-rich and -deficient segments may be able to expand the conducting range beyond that of unsubstituted oligomers and polymers. The first oxidation potential may be lowered (allowing easier access to the conducting emeraldine state) by introducing electron donating groups or polyaromatic groups which are easier to oxidize as a result of a higher level of delocalization. The second potential (entry to the pernigraniline state) may be raised by inserting electron-deficient segments. A hypothetical oligomer which may posses these properties is shown below (Scheme 14).

Scheme 14
Hypothetical nonamer with an electron-rich carbazole core (to lower the first oxidation potential) and fluorinated segments toward the ends (to raise the second potential).

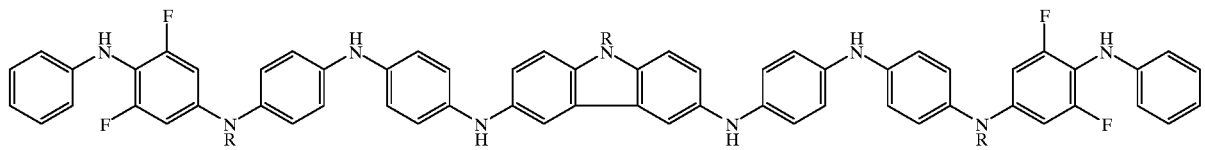

TABLE 3

| Problems with Conventional Conducting Materials | Advantages of Proposed Systems |
| --- | --- |
| • Doped materials have poor solubility properties making processing difficult | • Polyaromatic groups can accommodate solubilizing groups without loss in conductivity |
| • Attempts to introduce solubilizing groups sacrifice conductivity | • Polyaromatics may increase conductivity through enhanced crystallinity and intermolecular interactions |

As an alternative to conventional intermolecular interactions for polymer chain organization, metals binding to ligands incorporated into the backbone of oligomers (or as end groups as mentioned earlier) may form interchain crosslinks. Introducing pyridyl or phenanthroline moieties as shown in Scheme 15 should lead to chelation of metals (Lehn, J. M.; Rigault, A. *Angew. Chem. Int. Ed. Engl.* 1988, 27, 1095). Metals binding to adjacent chains should enforce better alignment (though adjacent chains may traverse in orthogonal directions), possibly improve conductivity (more crystalline or ordered regions of materials conduct better), and facilitate interchain electron transfer.

evaluated by cyclic voltammetry and U.V. to study systematically the influence that the changes in electronic structure and sterics have on the redox potential and band gap. In addition, X-ray studies will be carried out for elucidation of structure-property relationships. We will evaluate the correlation between various substituents, planar geometry, and conductivity by preparing a number of oligomer derivatives for crystal structure determination. As in the studies conducted by Mann and coworkers for oligothiophenes (Graf, D. D.; Duan, R. G.; Campbell, J. P.; Miller, L. L.; Mann, K. R. *J. Am. Chem. Soc.* 1997, 119, 5888), we will attempt to grow crystals of the oligomers in both the doped and undoped states to compare the relative geometries. Certain oligomers will have intended defects or ortho-substituents to relate the effects on geometry (by X-ray analysis), to loss in conductivity (as observed in electrochemical studies). We should observe in crystal structures the loss in planarity caused by substituents ortho to the nitrogens in the oligoaniline analogues.

In addition to conventional conductivity measurements, the oligomers will also be studied for application as molecular wires. The efficiency of the conducting oligomers will be evaluated by measuring the relative rates of electron transfer. Redox-active end groups, such as ferrocenes, on an oligomer should allow comparison of electron transfer rates via the Scheme 15
Pyridyl and phenanthroline chelates that may be inserted into oligoanilines for binding metals and crosslinking chains.

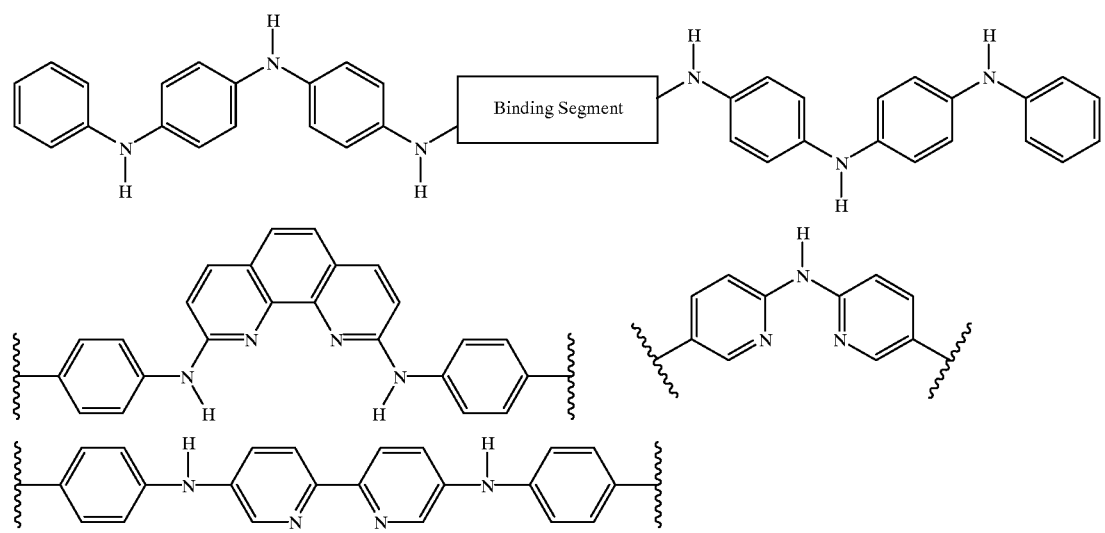

Evaluation of Designed Materials

The novel materials prepared (as described above with various substitutions to phenyl-capped octaaniline) will be magnitude of redox coupling (Field, L. D.; George, A. V.; Laschi, F.; Malouf, E. Y.; Zanello, P. *J. Organomet. Chem.* 1992, 435, 347). The larger the splitting or coupling as measured by cyclic voltammetry, the faster the rate of electron transfer. Redox coupling should only be observed for ferrocene derivatives with oxidation potentials within the conductive range of the oligomer.

In one embodiment, the conducting oligomer candidates can be tested as molecular wires to link metal clusters in self-assembled monolayers. The construction of planar metal cluster arrays coupled by semiconductors or metallic conductors has been proposed as a model for designing nanoscale digital circuits ((a) Tucker, J. R. *J. Appl. Phys.* 1992, 71, 4399. (b) Korotkov, A. N.; Chen, R. H.; Likharev, K. *J. Appl. Phys.* 1995, 78, 2520). Linking the metal clusters covalently with organic materials leads to higher stability of the array and control of electronic coupling (Andres, R. P.; Bielefeld, J. D.; Henderson, J. I.; Janes, D. B.; Kolagunta, V. R.; Kubiak, C. P.; Mahoney, W. J.; Osifchin, R. G. *Science* 1996, 273, 1690). The oligomers prepared for these experiments will have thiol or isocyanide end groups to serve as contacts between two gold particles. The organic conductors will exchange with dodecanethiol ligands on the gold clusters to form an ordered matrix (Scheme 16, FIG. 1). Conductivity will be measured by either using a scanning tunneling microscope to determine current-voltage responses of a gold cluster deposited on a monolayer of organic conductor connected to a gold surface, or by forming a linked gold cluster network between two metal contacts to study the current-voltage relationship. From the current-voltage data, the resistance of an individual oligomer molecule may be calculated (Andres, R. P.; Bein, T.; Dorogi, M.; Feng, S.; Henderson, J. I.; Kubiak, C. P.; Mahoney, W.; Osifchin, R. G.; Reifenberger, R. *Science* 1996, 273, 1323). Studies will be carried out on different chain lengths (4, 8, 12, 16) to determine the relation between oligomer length and resistance.

Design of Conducting Polymers and Copolymers

The trends that we observe from analysis (redox potentials, conductivity, solubility) of the oligomers will be applied to development of polymers and copolymers. While polymers may have poorer homogeneity and solubility than oligomers, their construction only involves the preparation of the monomer and the polymerization step (compared to a multistep synthesis for an oligomer). A polymerization strategy analogous to that described earlier (shown in Scheme 11 and again in Scheme 17) will be applied to linking building blocks which contain a terminal amine and bromide (Scheme 18). Materials comprising of random blends of monomers may be prepared by polymerizing two or more different monomers.

Scheme 17

Polymerization:

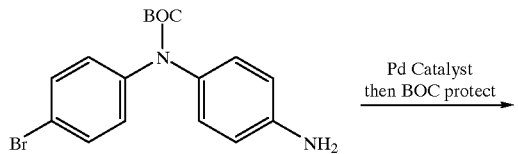

Pd Catalyst
then BOC protect

-continued

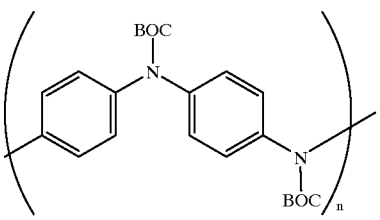

Scheme 18
Other potential monomers for producing polyaniline analogues which incorporate functionality to modify electronics, and solubility.

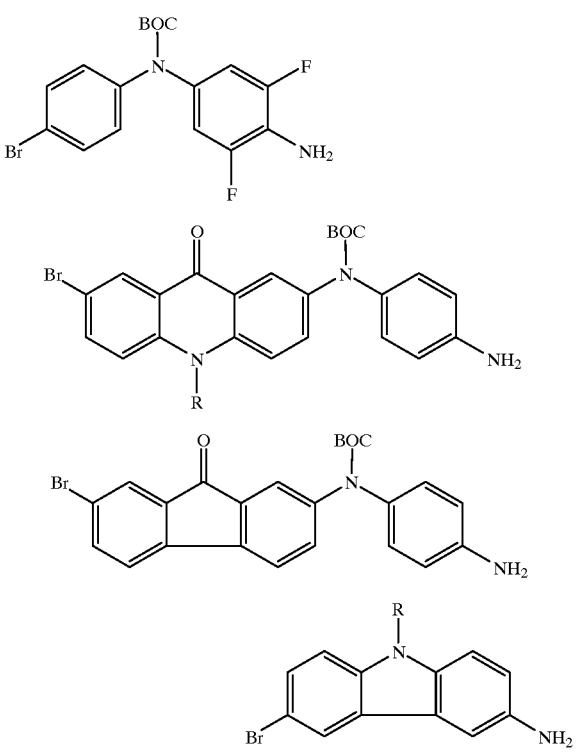

An alternative polymerization strategy involves the use of two functionally distinct monomers. To implement this approach, one of the monomers would require two terminal bromides and the other, two amines. The polymer assembly will alternate with the diamine and dibromide building blocks, allowing absolute control of the copolymer composition as shown in Scheme 19 below. Combining electron-rich and electron-deficient aromatic systems in a material should promote π-stacking arrangements ((a) Cozzi, F.; Cinquini, M.; Annunziata, R.; Dwyer, T.; Siegel, J.S. *J. Am. Chem. Soc.* 1992, 114, 5729. (b) Cozzi, F.; Cinquini, M.; Annunziata, R.; Siegel, J. S. *J. Am. Chem. Soc.* 1993, 115, 5330) which may enhance organization of the chains and lead to increased conductivity (Scheme 20).

Scheme 19

Representative Polymerization:
Controlled Copolymer Growth, Alternating Segments of Each Monomer

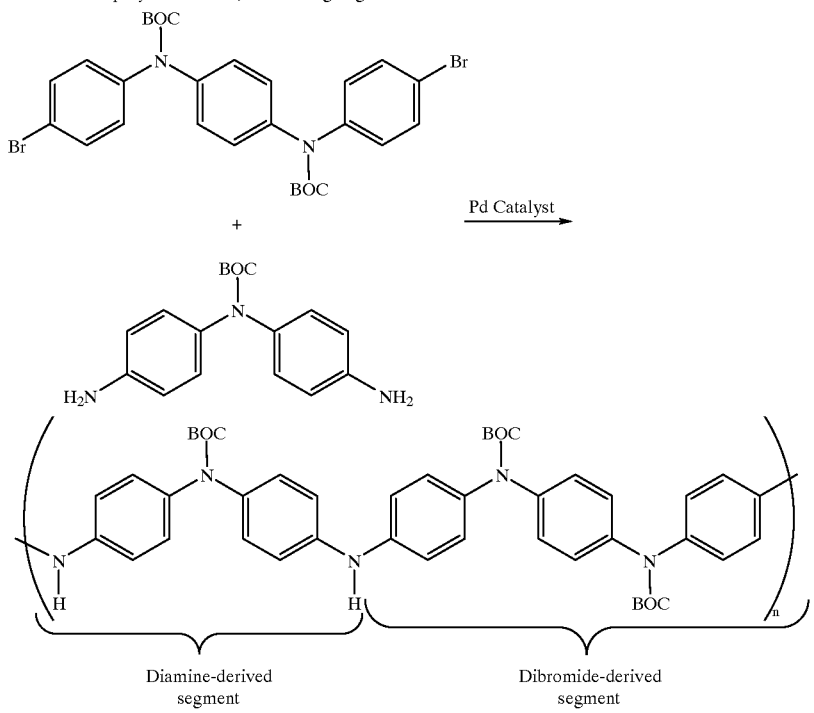

Scheme 20

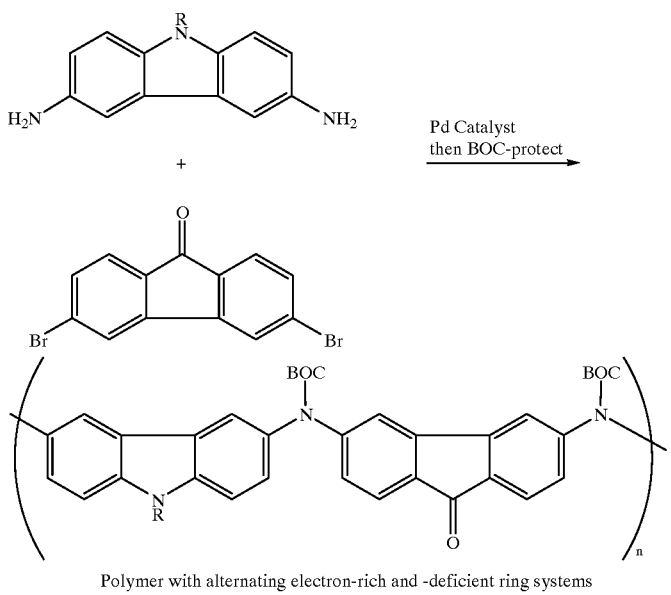

Polymer with alternating electron-rich and -deficient ring systems

Conventional Problem with Applications of Designer Polymers and Oligomers

In addition to the application of molecular wires for microelectronic devices, the flexibility in our synthetic approach permits designing materials for a broad range of potential applications including ion sensors, photolithography, fusing of plastics, and anticorrosion coatings.

Ion Sensors

To construct ion sensors, a ligand for recognition of the metal must be introduced into the oligoaniline backbone (Swager, T. M.; Marsella, M. J. Adv. Mater. 1994, 6, 595). When binding the appropriate substrate, conductivity through the oligomer must be affected to obtain a measurable response. For instance, one can incorporate various crown ether moieties into our oligoaniline framework for selectively binding metal ions (Izatt, R. M.; Bradshaw, J. S.; Neilson, S. A.; Lamb, J. D.; Christensen, J. J.; Sen, D. *Chem. Rev.* 1985, 85, 271) as shown in Scheme 21. The bound metals will fuinction analogously to protons for doping the emeraldine free-base state of the oligoaniline. As a result, metal binding, if as effective as proton doping, should enhance conductivity by up to 10 orders in magnitude (Chiang, J-C.; MacDiarmid, A. G. *Synth. Met.* 1986, 13, 193).

Other possible strategies include the disruption of oligomer conjugation with crown ethers or related macrocycles (Scheme 22). Upon metal binding, the segments of the oligomer will be linked, lowering the resistance. Alternatively, metal binding in such systems as shown in Scheme 22 could promote a redox process which would adjust the oxidation state of the oligomer. In this case specificity would not only arise from the binding recognition, but also electrochemically, since only a metal with a redox potential appropriately matched to the oligomer would alter the resistance ((a) Paul, E. W.; Ricco, A. J.; Wrighton, M. S. *J. Phys. Chem.* 1985, 89, 1441. (b) Beer, P. D. *Adv. Mater.* 1994, 6, 607).

Scheme 21
Doping induced by metal ion binding in crown ether-containing oligoanilines.

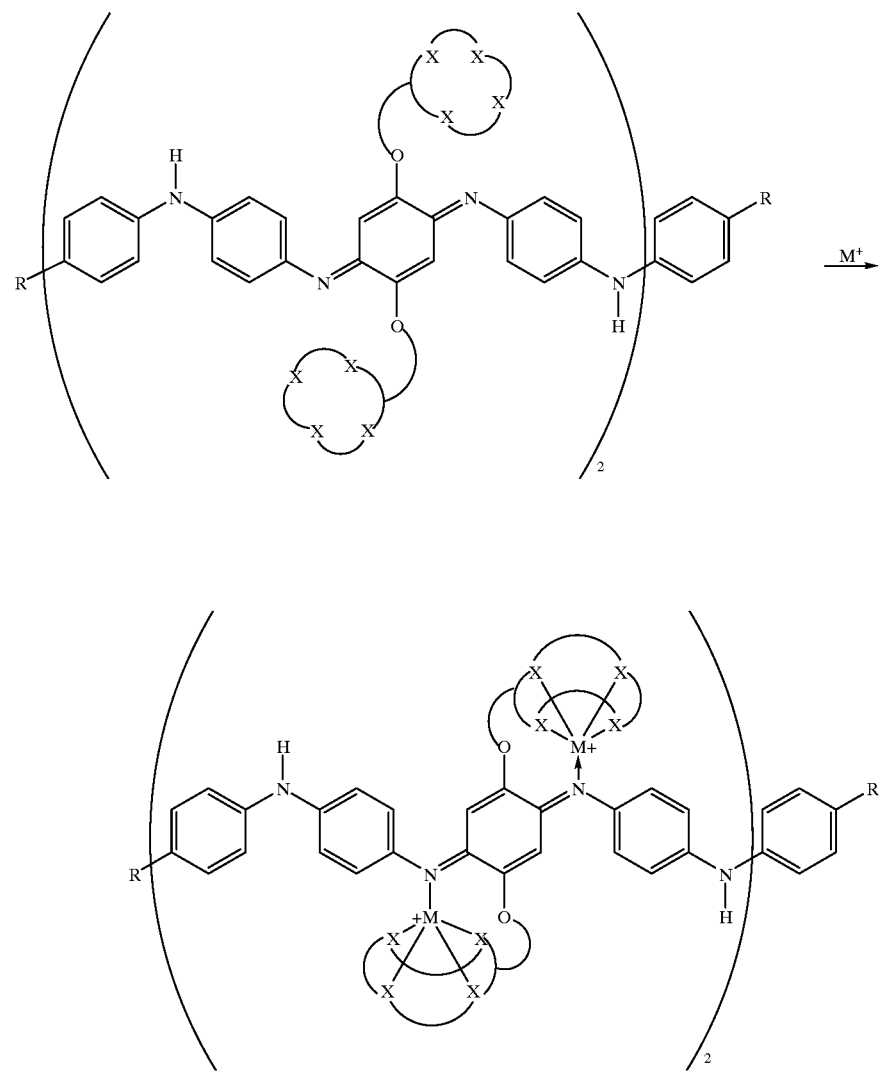

Scheme 22
Crown ether and tetraaza-macrocycle placed in oligoaniline backbone. Metal binding to macrocycle allows bridging of gap (conductively) between segments in oligomer.

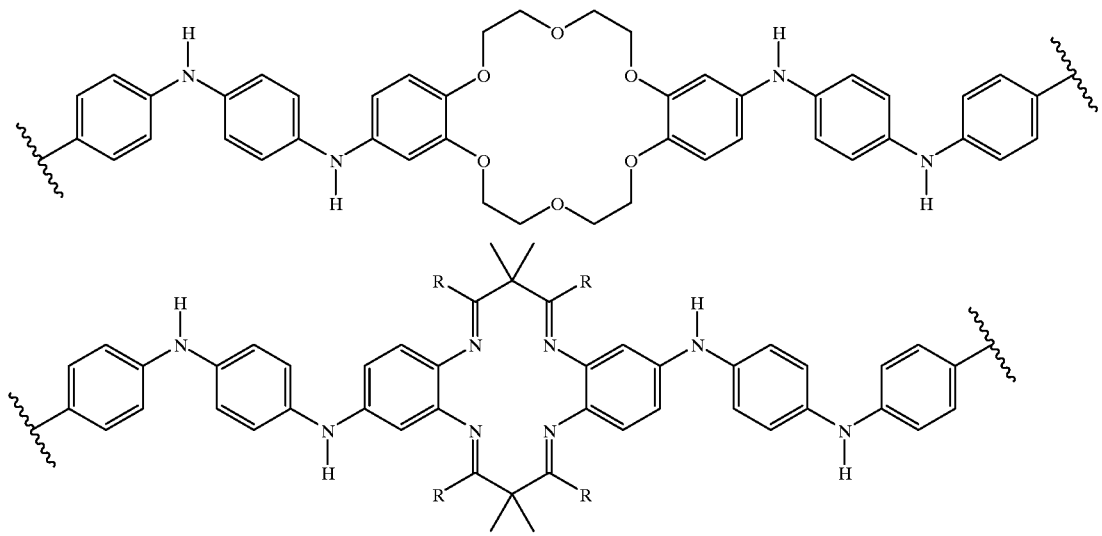

Organic molecules may be detected with systems designed similarly to those described above. The organic molecules may finction as ligands to displace or expel the metal from a ligand connected to the oligomer framework, which would result in an electrical resistance increase. It has recently been demonstrated by Swager and coworkers that ethylenediamine will displace copper from polyrotaxanes (a macrocyclic structure resembling a crown ether) (Zhu, S. S.; Carroll, P. J.; Swager, T. M. *J. Am. Chem. Soc.* 1996, 118, 8713). The same principle could be applied to our systems.

Other reactive or nucleophilic organic materials may be detected in analogous fashion. One potential application would be the design of specific sensors for toxic organic compounds. In Scheme 23 below, copper(I) is displaced from a bipyridyl ligand by cyanide ions (Sharpe, A. G. In *The Chemistry of Cyano Complexes of the Transition Metals*; Academic Press: London, 1976; pp 265–272) which should result in a loss in conductivity (by several orders of magnitude) of the oligomer.

Scheme 23
Sensor for cyanide. Cyanide ions displace copper from tetraaza-macrocycle in segment of oligomer causing a loss in conductivity.

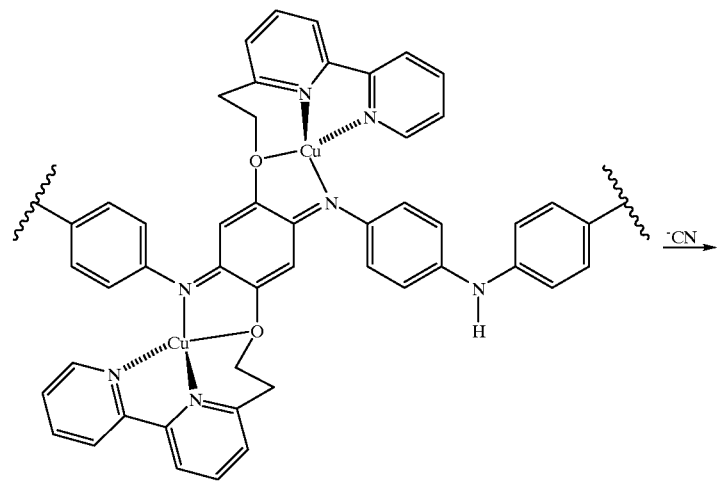

-continued

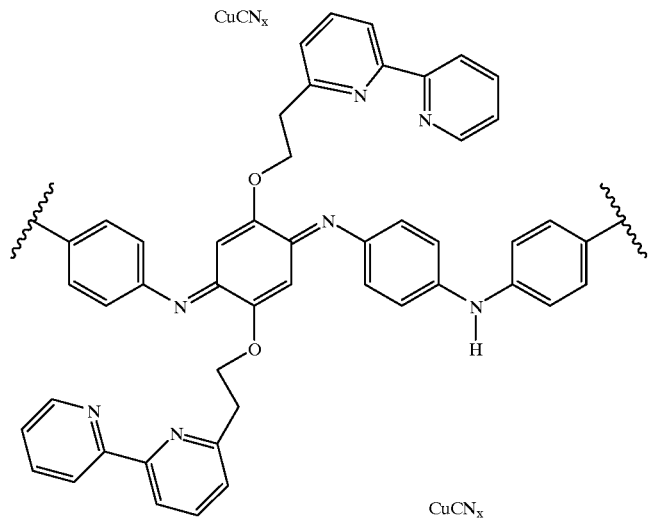

Limitations of Conventional Ion Sensors

Bound metals may cause quenching of fluorescence, or minor absorption change, by altering a single chromophore Bound metals affect only a localized chromophore; minor change to one chromophore in oligomer or polymer can be relatively difficult to detect

Advantages of Proposed Systems

Bound metals detected by conductivity enhancement, which is a bulk property of material (much more sensitive than absorption properties)

Enhancement in conductivity should be of several orders of magnitude with bound metal

Photolithography

Oligomers and polymers may be prepared which have photolabile protecting groups ((a) Pillai, V. N. R. *Synthesis* 1980, 1. (b) Amit, B.; Zehavi, U.; Patchornik, A. *J. Org. Chem.* 1974, 39, 192) rather than t-butylcarbamates (BOC), or a blend of the two as shown below in Scheme 24. It may be desirable to prepare analogues of oligoanilines or polyanilines which incorporate solubilizing groups throughout the chain (in the absence of the BOC groups) for ease in laying films from organic solvents. After deposition of a film of the protected material on a surface such as a silicon wafer, a laser could be used to expose the regions Scheme 24

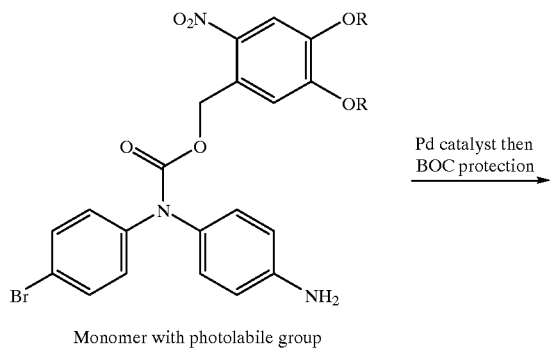

Monomer with photolabile group

Pd catalyst then BOC protection →

-continued

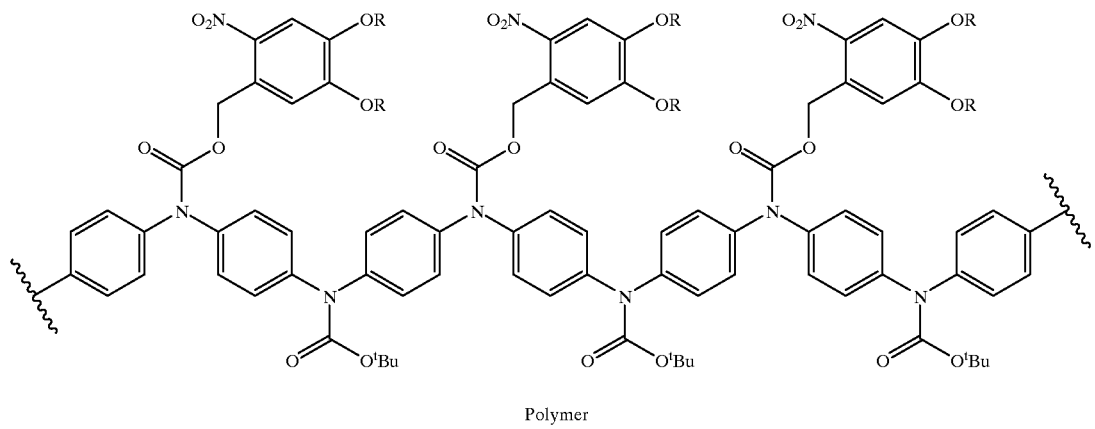

Polymer desired to function as conducting wires (shown in Scheme 25, FIG. 2). The deprotected regions could be doped to function as digital circuits while the unexposed regions remain insulating. Levels of complexity may be introduced by casting layers of films, each layer comprising of a polymer with protecting groups that may be removed orthogonally to the other polymer layers. For example, protecting groups may be differentiated in various layers by polymers possessing photolabile groups, each sensitive to a different wavelength range. Other means of differentiation include utilizing protecting groups labile to alternative methods of removal, such as thermolysis, acid, or base. Such systems could be models to replace conventional photoresists and conductors in silicon wafer technology (DeForest, W. S. In *Photoresist*; McGraw-Hill Book Company: New York, 1975; pp 132–213).

Fusing of Plastics

It has been demonstrated that plastic joints may be welded together with selective heating at the contact points through the combined use of polyanilines and thermoplastics (such as high density polyethylene) Epstein, A. J.; Joo, J.; Wu, C-Y.; Benatar, A.; Faisst, C. F.; Zegarski, J.; MacDiarmid, A. G. In *Intrinsically Conducting Polymers: An Emerging Technology*, Aldissi, M. Ed.; Kluwer Academic Publishers: Netherlands, 1993; p 165). The absorption of microwave radiation by the polyaniline results in heat evolution, melting the thermoplastic. Cooling of the blended polyaniline and thermoplastic causes fusing of the joined materials. The process may be reversed by reexposure to microwaves.

We could design materials combining the desired conductive and thermoplastic properties by the preparation of oligoaniline-polyurethane copolymers as shown in Scheme 26. The materials could be prepared from a dfisocyanate-capped oligomer, which could be copolymerized with (hydrocarbon chains terminated with) diols and diisocyanates. The advantage of such a system is that the thermoplastic and conducting oligomer will be blended evenly by the nature of the preparation, facilitating coherent heating and melting. The properties of the polyurethane can be tuned by choice of diol and diisocyanate (Callport, D.; Janes, W. H. In *Block Copolymers*; Applied Science Publishers Ltd.: London, 1973; p 224). Use of more soluble oligoaniline derivatives may aid in the handling and casting of such materials. In addition, we could prepare materials with functionality for more efficient microwave absorption. For example, employing oligomers with polyaromatic components (i.e. acridone, or carbazole) may lead to increased microwave absorption.

Scheme 26
Octaaniline/polyurethane copolymer. The thermoplastic properties of the polyurethane vary with the chain length of the diol (x) and of the diisocyanate (y).

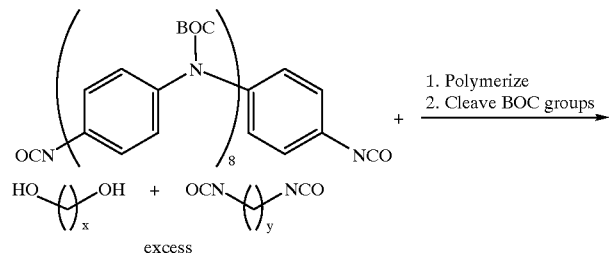

-continued

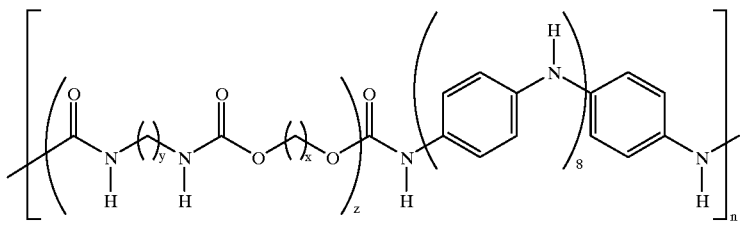

Anticorrosion Coatings

DeBerry discovered in 1985 that polyaniline deposited on a steel surface provided protection against corrosion (DeBerry, D. W. *J. Electrochem. Soc.* 1985, 132, 1022). The mechanism of protection was determined to be anodic in nature, such that the doped polyaniline stabilized a passive metal oxide coating from dissolution and reduction.

Our derivatives of oligoanilines and polyanilines could be applied to improving the anodic protection of the steel and preparing materials that adhere better to the metal surface. We could prepare oligomers, such as those shown below, with wide variations in redox potentials to alter electrochemical stability. In addition, polymer blends may be prepared which incorporate electron-rich or electron-poor components. After finding the optimal electronic composition of the material, we could introduce donor substituents (as end groups on oligomers, blends of copolymers, or as substituents on the backbone) which would be more amenable to metal adhesion. For example, the aryl end groups could be replaced by pyridyl rings, or the carbonyl of the fluorenone could be converted to a thiocarbonyl.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

Scheme 27
Electron-rich and -deficient octaanilines for studying the electronic properties of protecting steel against corrosion. The upper oligomer contains a carbazole group (in the center), alkoxy end groups and two methoxy groups (near the ends) to lower redox potentials. In contrast the lower oligomer has fluorinated aryl groups (near the ends), amide end groups, and a fluorenone group (in the center) to raise redox potentials.

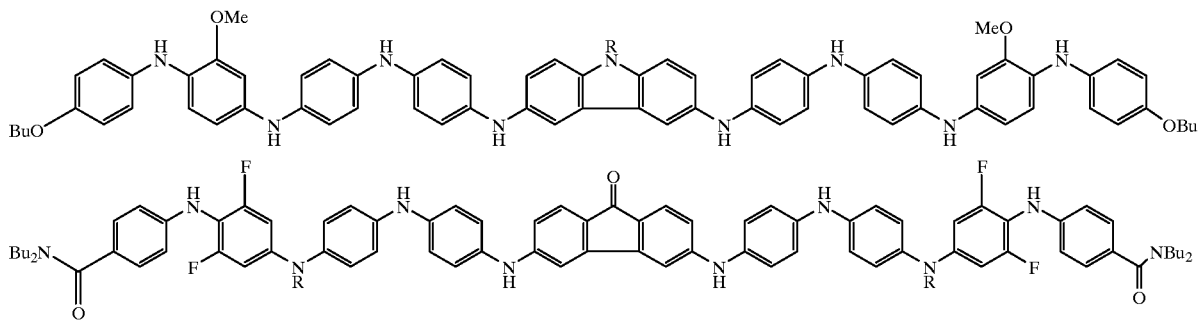

III. Reaction Conditions

The reactions of the present invention may be performed under a wide range of conditions, though it will be understood that the solvents and temperature ranges recited herein are not limiting and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants and catalyst. The reactions will usually be run at temperatures in the range of 25° C. to 300° C., more preferably in the range 25° C. to 150° C.

In certain embodiments it is preferable to perform the reactions under an inert atmosphere of a gas such as nitrogen or argon.

The reaction processes of the present invention can be conducted in continuous, semi-continuous, or batch fashion and may involve a liquid recycle operation as desired. The processes of this invention are preferably conducted in batch fashion. Likewise, the manner or order of addition of the reaction ingredients, catalyst and solvent are also not generally critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivativation with one or more of substituents of the aryl group.

IV Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g. a variation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Eliman U.S. Pat. No. 5,288,514: the Still et al. PCT publication WO 94/08051; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, for example, being linked to a polymer bead by a hydrolyzable or photolyzable group, for example, located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

Direct Characterization

A growing trend in the field of combinatorial chemistry is to exploit the sensitivity of techniques such as mass spectrometry (MS), for example, which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) PNAS 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811–5814; Valerio et al. (1991) Anal Biochem 197:168–177; Bray et al. (1991) Tetrahedron Lett 32:6163–6166).

C) Divide-Couple-Recombine

In yet another embodiment, a variegated library of compounds can be provided on a set of beads utilizing the strategy of divide-couple-recombine (see, for example, Houghten (1985) PNAS 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271–280; Fodor, S.P.A. (1991) Science 251:767; Pirrung et al. (1992) U.S. Pat. No. 5,143,854; Jacobs et al. (1994) Trends Biotechnol 12:19–26). The spatial resolution of photolithography affords miniaturization. This technique can be carried out through the use protection/deprotection reactions with photolabile protecting groups.

The key points of this technology are illustrated in Gallop et al. (1994) J Med. Chem. 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g. oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) PNAS 89:5381–5383), and an example of such a library appeared the following year (Needles et al. (1993) PNAS 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529–2531), orthogonality in synthesis is achieved by employing acid-labile protection for the coding strand and base-labile protection for the compound strand.

In an alternative approach (Nikolaiev et al. (1993) Pept Res 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags have confinmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) PNAS 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (i.e. upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention and are not intended to limit the invention.

Example 1

A General Synthesis of End-Functionalized Oligoanilines via Palladium-Catalyzed Amination The palladium-catalyzed amination of aryl halides has been applied to the synthesis of octaanilines utilizing a bidirectional assembly strategy. The materials are prepared in four isolated steps which proceed in good yield. Oligoanilines of other chain lengths may be prepared by appending different side chains to a symmetrical core building block. The synthesis of oligoanilines with functionalized terminal aryl groups is accomplished in a facile manner.

Polyaniline has attracted much attention in the field of organic conducting polymers due to its robust nature in the doped emeraldine state.[1] Among the many industrial applications it has found are its use as components in rechargeable batteries,[2] electromagnetic interference shielding,[3] and anticorrosion coatings for steel.[4]

In 1986, Wudl and coworkers demonstrated that synthetically prepared phenyl-capped octaaniline exhibited properties similar to bulk polyaniline (comparable UV/vis, IR, CV, and conductivity).[5] Consequently, an octaaniline could be considered a good model or substitute for applications involving polyaniline. Aside from the modified Honzl condensation method Wudl employed for synthesizing oligoanilines, other methods of preparation include titanium alkoxide-mediated couplings with aniline derivatives,[6] Ullmann couplings,[7] and an adaptation of the Willstätter-Moore approach.[8] All of these methods have yet to demonstrate generality in the choice of substrates for carrying out oligomerizations and have the common drawback of lacking the ability to functionalize end groups.

We desired to expand the repertoire of techniques available for constructing oligoanilines and their analogs to include a strategy based on Pd-catalyzed amination methodology. We speculated that such a method would demonstrate efficiency in the preparation of oligoanilines and derivatives due to the broad scope of the Pd-catalyzed amination reaction.[9] To undertake such an objective, three issues had to be confronted. First, an orthogonal protecting group strategy had to be developed to differentiate internal and terminal nitrogens. Second, a means of masking or selectively introducing terminal bromides for use in couplings with aniline derivatives had to be implemented. Third, and most importantly, construction would have to be carried out in a bi-directional mode to produce materials with symmetry. Herein we report our first efforts toward a unified strategy for synthesizing oligoanilines with end group functionalization. In light of Wudl's pioneering studies,[5] we initially chose to target functionalized octaanilines.

As a surrogate for 4-bromoaniline in the controlled construction of oligoanilines we used N-diphenylmethylene-4-bromoaniline (1).[10] The imine group serves the dual purposes of protecting the nitrogen and activating the compound to oxidative-addition to the Pd catalyst. To build symmetrical oligomers we employed 1,4-phenylenediamine dihydrochloride (2) as a core piece for initiating two-directional growth. We found that coupling took place smoothly using 1 (2 equiv) and 2 (1 equiv) in the presence of Pd(OAc)$_2$ (1 mol %), BINAP (1.5 mol %) and NaO$^t$Bu (4.5 equiv) in toluene at 80° C. To avoid oxidation of the desired product, each of the internal amines was protected, in situ, as a tert-butyl carbamate (BOC) by addition of (BOC)$_2$O and a catalytic amount of 4-dimethylaminopyridine (DMAP). The crude diphenyl ketimine product was cleaved with hydroxylamine hydrochloride[11] to afford 3 in an overall yield of 91%.

Scheme 1

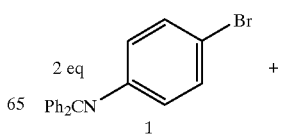

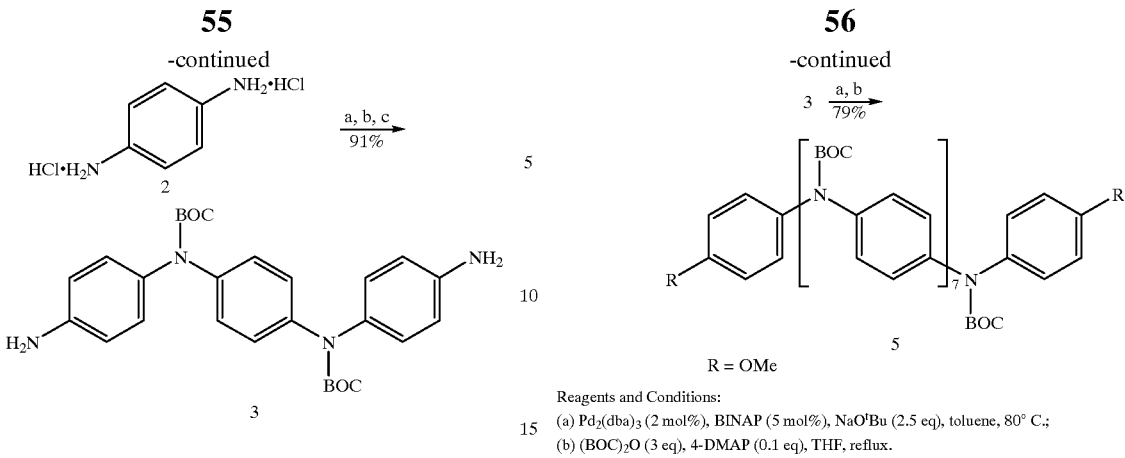

Two approaches were taken to complete the assembly of the octamers. The first strategy (Scheme 2) entails coupling diamine 3 with bromide 4 (2 equiv)[12] followed by BOC-protection of the initially formed intermediate. The 4-methoxyphenyl-capped octamer (5, R=OMe) was constructed in this manner in 79% yield.

Scheme 2

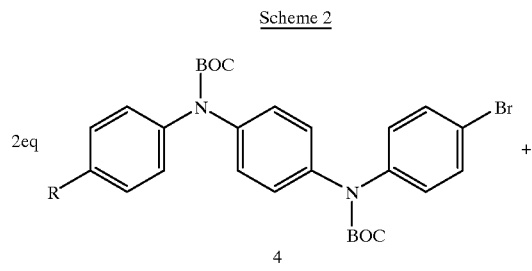

While this first strategy (Scheme 2) is highly convergent, a second route was adopted for the purpose of rapidly building a family of octaanilines from a common precursor as shown below in Scheme 3. This alternative route commences with a Pd-catalyzed coupling of 3 and 8 (see below) to produce 9 after in situ BOC-protection (74%). Diamine 10 was obtained in 86% by hydrogenolysis of 9 with Pd(OH)$_2$/carbon and ammonium formate. Capping 10 by Pd-catalyzed coupling with the appropriate aryl bromide (followed by in situ BOC-protection) provided the desired octaaniline (77–82%). Octamers (5) capped with R=H, tert-butyl, dodecyl and cyano were prepared in this fashion and were found to be soluble in most common organic solvents.[13]

Scheme 3

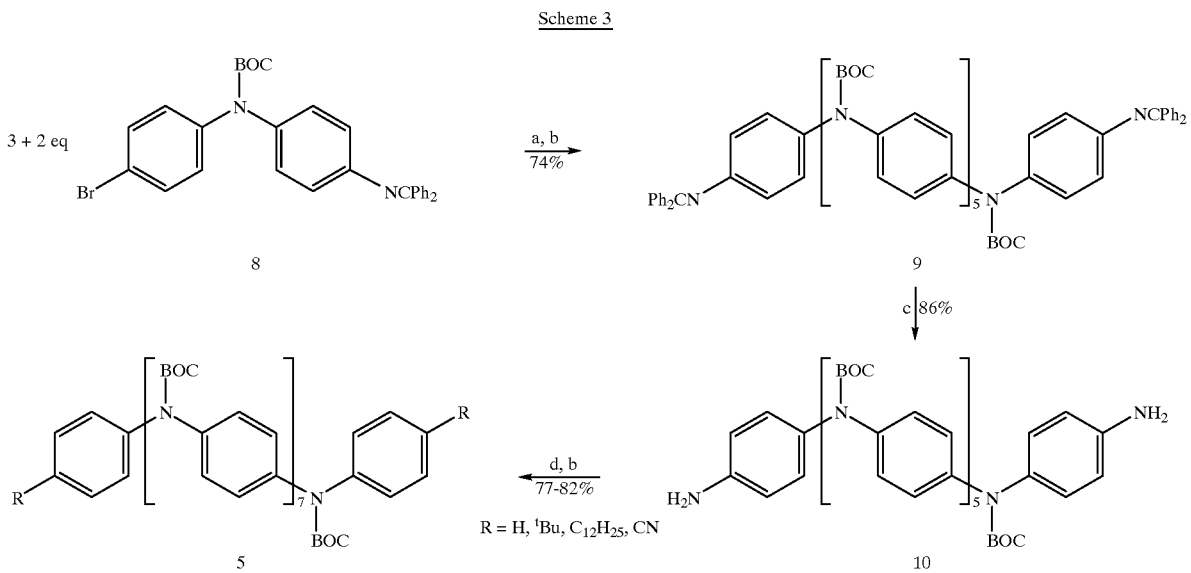

Reagents and Conditions:
(a) Pd(OAc)$_2$ (6 mol%), BINAP (7 mol%), NaO$^t$Bu (2.8 eq), toluene, Et$_3$N, 90° C.;
(b) (BOC)$_2$O (3 eq), 4-DMAP (0.1 eq), THF, reflux;
(c) 20% Pd(OH)$_2$/C (0.4 eq), (NH$_4$)HCO$_2$ (20 eq), THF/EtOH (2:1), 70° C.;
(d) RC$_6$H$_4$Br (2.1 eq), Pd$_2$(dba)$_3$ (2 mol%), BINAP (6 mol%), NaO$^t$Bu (2.5 eq), THF, reflux.

Essential to the efficiency of this route is the facile construction of 8 as illustrated in Scheme 4. Coupling of 1 with aniline with $Pd_2(dba)_3$ (0.1 mol %) and BINAP (0.24 mol %) proceeded cleanly to give intermediate 11. Regioselective bromination followed by BOC-protection of the crude coupling product (11) provided 8 in 81% yield for the 3 step sequence.[14]

Scheme 4

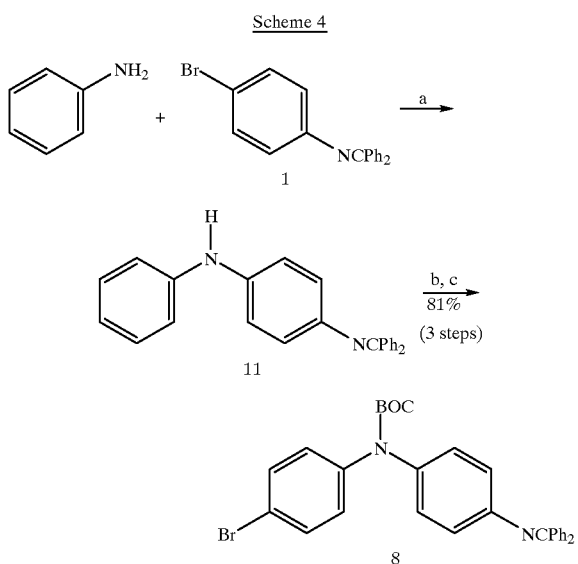

Reagents and Conditions:
(a) $Pd_2(dba)_3$ (0.1 mol%), BINAP (0.24 mol%), $NaO^tBu$ (1.4 eq), THF, reflux;
(b) $Bu_4NBr_3$, $CH_2Cl_2$, rt;
(c) $(BOC)_2O$ (1.5 eq), 4-DMAP (0.05 eq), THF, reflux.

The BOC groups throughout the backbone of the octamers prevent oxidation of the material and ease its handling by improving solubility.[15] The BOC groups were removed quantitatively either by thermolysis[16] (185° C., 9 h), or by treatment with TMSI[17] at rt in $CH_2Cl2$, followed by addition of triethylamine and methanol. Analysis by $^1H$ NMR, IR and UV/vis spectroscopies indicated that the deprotection was clean in each case producing octaanilines in the leucoemeraldine state. When these materials were oxidized to the emeraldine state[18] under acidic conditions, we observed, by UW-visible spectroscopy, an absorption between 700 and 1000 nm, characteristic of the narrow band gap in oligoanilines and polyaniline.[5b]

Scheme 5

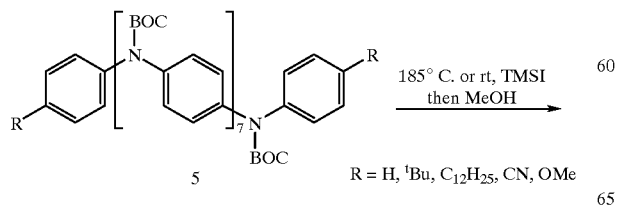

R = H, $^tBu$, $C_{12}H_{25}$, CN, OMe

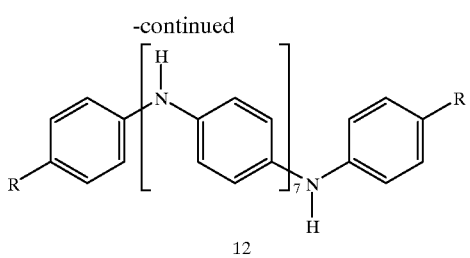

Oligoanilines other than octamers or tetramers (capping of 3) are accessible by appending different side chains to 3. Towards this end, we developed a divergent/convergent approach[19] (Scheme 6) to build nonsymmetrical oligomers. The key component in this strategy is 13 prepared from the Pd-catalyzed coupling of 4-(trimethylsilyl)aniline[20] with 1, followed by in situ BOC-protection. One portion of 13 was subjected to hydrogenolysis, affording amine 14, and a second portion was regioselectively brominated to produce 8. The combination of 14 and 8 was subjected to Pd-catalyzed amination. After in situ BOC-protection of the crude product, 15 was obtained in 89% yield. This process may be used to construct oligomers of longer chain lengths, doubling in length with each iteration.

Scheme 6

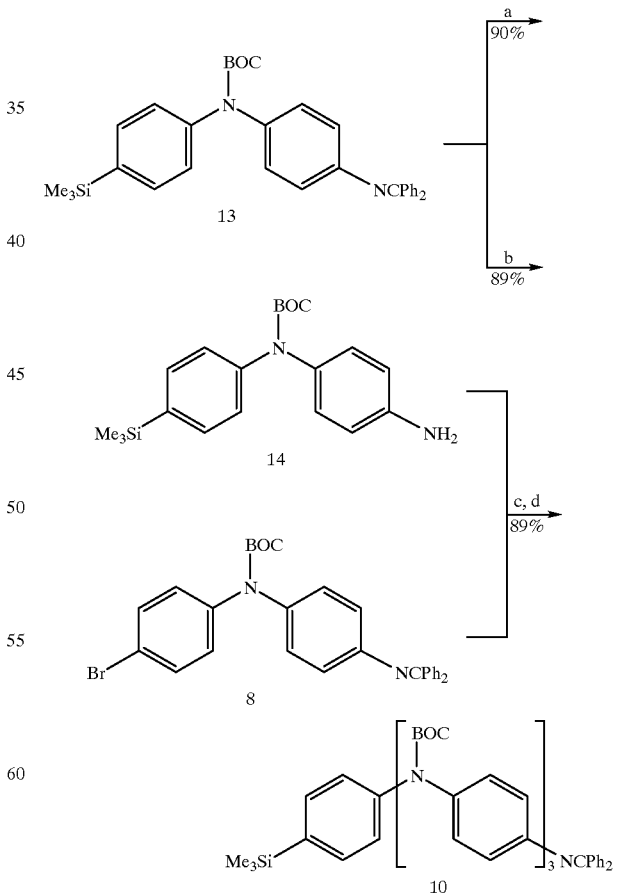

-continued

Reagents and Conditions:
(a) (NH₄)HCO₂ (12 eq), 10% Pd/C (0.1 eq), EtOH, 60° C.;
(b) Br₂, NaOAc, THF, 0° C.;
(c) Pd₂(dba)₃ (2 mol%), BINAP (5 mol%), toluene, 80° C.;
(d) (BOC)₂O (1.5 eq), 4-DMAP (0.1 eq), THF, reflux.

This new approach to constructing oligoanilines should prove to be general in nature for building oligomers of any length by combining the products assembled from the divergent/convergent strategy with various symmetrical building blocks (2, 3, 10, or others[21]). The current work provides octaanilines with flexibility in modification of the end groups. In addition, protecting the amines as tert-butyl carbamates facilitates manipulations of the materials by impeding oxidation and solubilizing the oligoaniline. The syntheses of the materials can be efficiently carried out on a multigramn scale since all intermediates and end products were isolated as solids by recrystallization or precipitation.[22] Electrochemical studies as well as the preparation of oligoanilines of varying chain length are in progress and will be reported in due course. Representative procedures for the synthesis of various ring-substituted monomer equivalents, ring-substituted oligomer fragments, and protected polyaniline can be found in Example 2.

References for Example 1

(1) (a) Huang, W.-S.; Humphrey, B. D.; MacDiarmid, A. G. *J. Chem. Soc., Faraday Trans.* 1 1986, 82, 2385–2400. (b) Chen, S.-A.; Fang, W.-G. *Macromolecules* 1991, 24, 1242–1248. (c) Chiang, J.-C.; MacDiarmid, A. G. *Synth. Met.* 1985, 13, 193–205.

(2) MacDiarmid, A. G.; Mu, S.-L.; Somasiri, N. L. D.; Wu, W. *Mol. Cryst. Liq. Cryst.* 1985, 121, 187–190.

(3) (a) Taka, T. *Synth. Met.* 1991, 41, 1177–1180. (b) Colaneri, N. F.; Shacklette, L. W. *IEEE Trans. Instrum. Meas.* 1992, 41, 291. (c) Joo, J.; Epstein, A. *J. Appl. Phys. Lett.* 1994, 65, 2278–2280.

(4) (a) DeBerry, D. W. *J. Electrochem. Soc.* 1985, 132, 1022–1026. (b) Ahmad, N.; MacDiarmid, A. G. *Synth. Met.* 1996, 78, 103–110. (c) Lu, W.-K.; Elsenbaumer, R. L.; Wessling, B. *Synth. Met.* 1995, 71, 2163–2166.

(5) (a) Lu, F.-L.; Wudl, F.; Nowak, M.; Heeger, A. J. *J. Am. Chem. Soc.* 1986, 108, 8311–8313. (b) Wudl, F.; Angus, R. O., Jr.; Lu, F. L.; Allemand, P. M.; Vachon, D. J.; Nowak, M.; Liu, Z. X.; Heeger, A. J. *J. Am. Chem. Soc.* 1987, 109, 3677–3684.

(6) Ochi, M.; Furusho, H.; Tanaka, J. *Bull. Chem. Soc. Jpn.* 1994, 67, 1749–1752.

(7) Rebourt, E.; Joule, J. A.; Monkinan, A. P. *Synth. Met.* 1997, 84, 65–66.

(8) Zhang, W. J.; Feng, J.; MacDiarmid, A. G.; Epstein, A. J. *Synth. Met.* 1997, 84, 119–120.

(9) (a) Wolfe, J. P.; Wagaw, S.; Buchwald, S. L. *J. Am. Chem. Soc.* 1996, 118, 7215–7216 and references cited therein. (b) Driver, M. S.; Hartwig, J. F. *J. Am. Chem. Soc.* 1996, 118, 7217–7218.

(10) Taguchi, K.; Westheimer, F. H. *J. Org. Chem.* 1971, 36, 1570–1572.

(11) Fasth, K.-J.; Antoni, G.; Långström, B. *J. Chem. Soc. Perkin Trans.* 1 1988, 3081–3084.

(12) Precursor 4 was prepared in two isolated steps. Intermediate 7 was isolated in 84% yield following a Pd coupling and in situ BOC-protection. Hydrogenolysis of 7, followed by coupling with 1,4-dibromobenzene and in situ BOC-protection afforded 4 in 75% yield. For experimental details, see supplementary material.

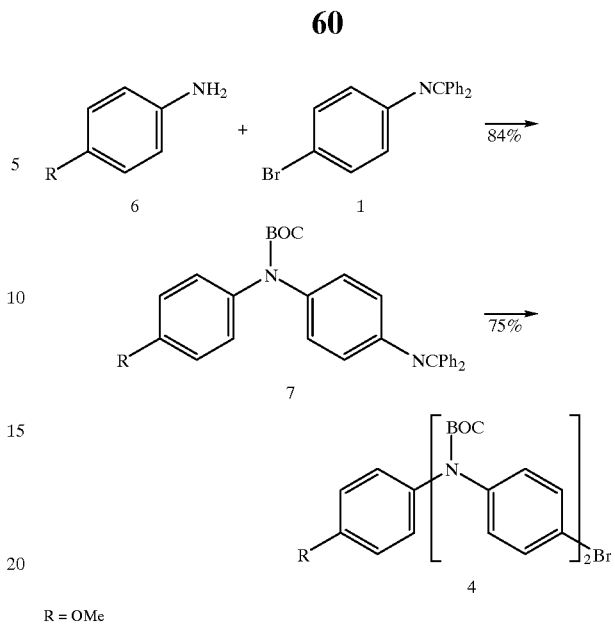

R = OMe

(13) The BOC-protected oligomers (5) were quite soluble in solvents such as CH₂Cl₂, EtOAc, THF, Et₂O; however, the deprotected oligoanilines were only sparingly soluble in polar solvents such as DMF or NMP, as observed in previous studies.[5–8]

(14) Berthelot, J.; Guette, C.; Desbène, P.-L.; Basselier, J.-J.; Chaquin, P.; Masure, D. *Can. J. Chem.* 1989, 67, 2061–2066.

(15) An additional benefit of the BOC group lies in its ability to activate toward Pd oxidative addition substrates which contain a secondary aromatic amine para to a bromide (such as 4 or 8). In the absence of BOC-protection, such substrates generally fail to couple with amines under standard Pd-catalyzed amination conditions.

(16) Rawal, V. H.; Jones, R. J.; Cava, M. P. *J. Org. Chem.* 1987, 52, 19–28.

(17) Lott, R. S.; Chauhan, V. S.; Stammer, C. H. *J. Chem. Soc., Chem. Commun.* 1979, 495–496.

(18) MacDiarmid, A. G.; Chiang, J. C.; Richter, A. F.; Somasiri, N. L. D.; Epstein, A. J. *Conducting Polymers* 1987, 105–120.

(19) For a description of the divergent/convergent approach applied to the construction of other electroactive oligomers, see: Tour, J. M. *Chem. Rev.* 1996, 96, 537–553.

(20) Walton, D. R. M. *J. Chem. Soc.* C 1966, 1706–1707.

(21) Odd-numbered oligoanilines should be accessible from p-H₂NC₆H₄)₂N-BOC (in place of 3 in Scheme 2) which may be derived from 4,4'-dibromodiphenylamine as described in: Wolfe, J. P.; Åhman, J.; Sadighi, J. P.; Singer, R. A.; Buchwald, S. L. *Tetrahedron Lett.* 1997, 38, 6367–6370.

(22) All isolated intermediates and products (3, 4, 5, 7, 8, 9, 10, 13, 14, 15) were characterized by ¹H and ¹³C NMR spectroscopy, IR, and C,H elemental analysis.

Supporting Information for Example 1

Experimental Data

General Information. Proton and carbon nuclear magnetic resonance spectra (¹H NMR and ¹³C NMR) were recorded on Varian XL-300, UN-300 or XL-500 spectrometers and referenced with respect to residual solvent. Data for ¹H NMR are reported as follows: chemical shift (δ in ppm), multiplicity (s singlet, bs broad singlet, d doublet, t triplet, q quartet, dd doublet of doublets, dt doublet of triplets, m multiplet), coupling constant (J in Hz), and integration. Infrared spectroscopy was carried out on a Perkin-Elmer 1600 Series FT-IR spectrometer. UV/Visible spectra were obtained using a Hewlett-Packard 8453A spectrophotometer. FAB high resolution mass spectroscopy was carried out using a 3-nitrobenzyl alcohol matrix. Elemental analyses were carried out by E & R Microanalytical Laboratory Inc., Corona, N.Y. Thin layer chromatography was carried out on E. Merck SIlica Gel 60 F-254 TLC plates.

Reactions under an argon atmosphere were carried out in oven-dried glassware using standard Schlenk techniques. Tetrahydrofuran (THF) was distilled under argon from sodium benzophenone ketyl. Toluene was distilled under nitrogen from molten sodium. Dichloromethane, used in oligomer deprotections, was purchased anhydrous from Aldrich Chemical Company and stored under nitrogen over activated 3 Å molecular sieves. Absolute ethanol was purchased from Pharmco and used as supplied. Diethyl ether, analytical reagent grade, was purchased from Mallinckrodt and used as supplied. N-Methylpyrrolidinone, anhydrous, and N,N-dimethylformamide, reagent grade, were purchased from Aldrich Chemical Company and used as supplied. Deuterated solvents were purchased from Cambridge Isotope Laboratories and used as supplied. All other solvents were of liquid chromatography grade quality, purchased from EM Science and used as supplied.

Molecular sieves were purchased from Aldrich Chemical Company and activated at 180° C. and $10^{-3}$ mm Hg for 12 h prior to use. Sodium tert-butoxide was purchased from Aldrich Chemical Company and stored in a Vacuum Atmospheres glovebox under nitrogen. Small amounts were removed from the glovebox as needed, stored in a dessicator for up to one week, and weighed in the air. 4-Bromoaniline, benzophenone, chlorotrimethylsilane, p-anisidine, 1,4-dibromobenzene, di-tert-butyl dicarbonate solution (1.0 M in THF), tetra-$^n$butylammonium tribromide, palladium hydroxide (moist, 20% on carbon), 1,4-phenylenediamine dihydrochloride, aniline, bromobenzene, 4-bromo-tert-butylbenzene, 4-bromobenzonitrile, ammonium formate, hydroxylamine hydrochloride, and hexamethyldisilane were purchased from Aldrich Chemical Company and used as supplied. Di-tert-butyl dicarbonate and 4-dimethylaminopyridine (4-DMAP) were purchased from Lancaster Synthesis Inc. and used as supplied. 4-Bromo-$^n$dodecylbenzene was purchased from TCI America and used as supplied. S-BINAP, a gift from Pfizer, was used as supplied. Tris(dibenzylideneacetone)dipalladium, palladium acetate, palladium on carbon, $^n$butyllithium (1.6 M in hexanes) and bromine were purchased from Strem Chemical Company and used without further purification. All other inorganic reagents were analytical reagent grades purchased from Mallinckrodt and used as supplied.

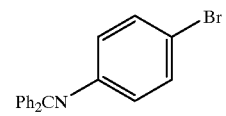

1

N-Diphenylmethylene-4-bromoaniline (1). The method of Taguchi and Westheimer[1] was modified as follows: benzophenone (455 g, 2.50 mol) and 4-bromoaniline (473 g, 2.75 mol) were dissolved in toluene (1.2 L) under argon in a 5 L flask containing activated molecular sieves (5 Å, 1.25 kg). The flask was fitted with a reflux condenser, rubber septum, and pressure outlet. The mixture was heated to gentle reflux and shaken occasionally; an intense yellow color soon developed. After 18 h, heating was discontinued and the solution was cooled to rt. The solution was decanted from the molecular sieves, and the sieves were washed with Et$_2$O until the filtrate was colorless. The combined organic solutions were concentrated in vacuo to give an orange oil. MeOH (ca. 80 mL) and a seed crystal of 1 were added. The product was allowed to crystallize at 0° C. and the precipitate was collected by filtration. The mother liquor was further concentrated, and a second crop of crystals was collected from MeOH. Recrystallization of the combined material from MeOH afforded yellow crystals (760 g, 90%). 1: mp 82–83° C.; $^1$H NMR (300 Mz, CDCl$_3$) δ 7.75 (dd, J=6.9, 1.6 Hz, 2H), 7.52–7.39 (m, 3H), 7.32–7.23 (m, 5H), 7.11 (dd, J=8.5, 2.0 Hz, 2H), 6.61 (dt, J=8.5, 2.0 Hz, 2H); $^{13}$C NMR (75 MHz, CDCl$_3$) δ 168.7, 150.4, 139.5, 136.1, 131.6, 131.0, 129.5, 128.8, 128.3, 128.2, 122.8, 116.3, 103.6;IR(CDCl$_3$) 3058, 3024, 1615, 1478 cm$^{-1}$; Anal. Calcd for C$_{19}$H$_{14}$BrN: C, 67.87; H, 4.20. Found: C, 68.08; H, 4.28.

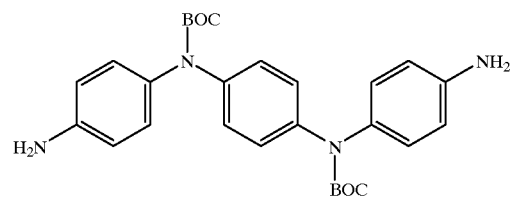

3

Diamine 3. A solution of 1,4-phenylenediamine dihydrochloride (4.53 g, 25.0 mmol), bromide 1 (17.0 g, 50.5 mmol), sodium tert-butoxide (10.8 g, 113 mmol), Pd(OAc)$_2$ (56.1 mg, 0.250 mmol), and BINAP (234 mg, 0.375 mmol) in toluene (200 mL) under Ar was heated to 80° C. for 24 h. The heat was temporarily removed and 4-DMAP (305 mg, 2.50 mmol), THF (50 mL) and a 1.0 M solution of (BOC)$_2$0 (87.5 mmol) in THF (87.5 mL) were added. Heating was then resumed for another 24 h. The hot reaction mixture was poured onto hot EtOH (400 mL) and allowed to stand for 6 h at rt. The yellow powder which formed was collected by filtration. The crude product and hydroxylamine hydrochloride[2] (4.34 g, 62.5 mmol) were suspended in CHCl$_3$ (400 mL), THF (100 mL), EtOH (50 mL), and pyridine (8.00 mL). The suspension was stirred for 3 h and then was treated with triethylamine (34.8 mL, 250 mmol). After stirring for another 3 h, the reaction mixture was concentrated in vacuo. The residue was heated in a mixture of isopropanol (600 mL), CHCl$_3$ (120 mL) and water (60 mL) for 10 min and then allowed to stand at rt for 12 h. The precipitate which formed was collected by filtration, and washed with water followed by isopropanol. The solid was dried under vacuum to afford a white powder (11.1 g, 91%). 3: mp 208–211° C.; $^1$H NMR (300 MHz, DMSO-$d_6$) δ 7.06 (s, 4H), 6.81 (d, J=8.4 Hz, 4H), 6.49 (d, J=8.4 Hz, 4H), 5.11 (s, 4H), 1.33 (s, 18 H); $^{13}$C NMR (75 MHz, DMSO-$d_6$) δ 153.4, 146.9, 140.2, 131.1, 128.0, 125.9, 113.8, 79.6, 27.8; IR (CH$_2$Cl$_2$) 3460, 3364, 1707 cm$^{-1}$; Anal. Calcd for $C_{28}H_{34}N_4O_4$: C, 68.55; H, 6.99. Found: C, 68.57; H, 7.05.

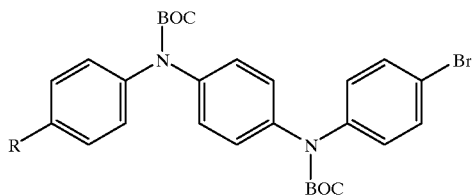

4

Bromide 4 (R=OMe). A suspension of imine 7 (1.00 g, 2.09 mmol), ammonium formate (2.64 g, 41.8 mmol), and Pd(OH)$_2$ (291 mg, 0.209 mmol) in EtOH (20 mL) was heated to 60° C. for 30 min. The reaction mixture was then cooled to rt and diluted with EtOAc (40 mL) prior to being passed through a plug of Celite. The filtrate was diluted with additional EtOAc (60 mL) and washed with 2.0 M NaOH (100 mL). The organic layer was washed with saturated aqueous NaCl (50 mL), dried over anhydrous Na$_2$SO$_4$, and concentrated in vacuo. The white solid which formed was redissolved in THF (10 mL) under Ar, and 1,4-dibromobenzene (470 mg, 1.99 mmol), sodium tert-butoxide (268 mg, 2.79 mmol), Pd$_2$(dba)$_3$ (18.2 mg, 0.0199 mmol), and BINAP (37.2 mg, 0.0598 mmol) were added. The solution was heated to reflux for 24 h. Heating was then stopped, and 4-DMAP (24.0 mg, 0.199 mmol) and a 1.0 M solution of (BOC)$_2$O in THF (3.00 mL) were added. Heating was resumed for 3 h and then the reaction mixture was cooled to rt. The reaction mixture was then diluted with 2:1 hexane/EtOAc (10 mL) and passed through a plug of Celite. The filtrate was concentrated in vacuo to yield a solid. The solid was recrystallized from CH$_2$Cl$_2$ (6 mL) and MeOH (30 mL). The resulting crystalline material which formed was isolated by filtration and dried under vacuum to afford white crystals (847 mg, 75%). 4 (R=OMe): mp 169–170° C.; $^1$H NMR (300 MHz, CDCl$_3$) δ 7.40 (d, J=8.7 Hz, 2H), 7.17–7.06 (m, 8H), 6.84 (d, J=9.0 Hz, 2H), 3.80 (s, 3H), 1.44 (s, 18H); $^{13}$C NMR (75 MHz, CDCl$_3$) δ 157.7, 153.9, 153.4, 142.0, 141.0, 139.3, 135.6, 131.7, 128.5, 128.3, 127.0, 126.4, 118.9, 114.1, 81.6, 81.1, 55.4, 28.2, 28.2; IR (CDCl$_3$) 1709 cm$^{-1}$; Anal. Calcd for $C_{29}H_{33}BrN_2O_5$: C, 61.16; H, 5.84. Found: C, 61.15; H, 5.81.

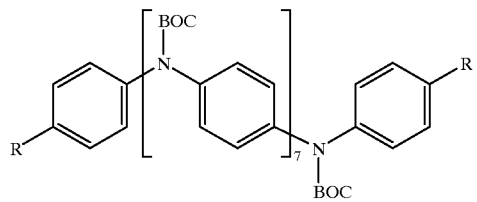

5

Octamer 5 (=OMe). A solution of bromide 4 (300 mg, 0.527 mmol), diamine 3 (123 mg, 0.251 mmol), sodium tert-butoxide (60 mg, 0.627 mmol), Pd$_2$(dba)$_3$ (4.6 mg, 0.00502 mmol), and BINAP (9.4 mg, 0.0151 mmol) in toluene (3 mL) under Ar was heated to reflux for 48 h. The heat was removed temporarily, and 4-DMAP (3.1 mg, 0.0251 mmol) and a 1.0 M solution of (BOC)$_2$O in THF (879 μL) were added. Heating was resumed for 3 h and then the solution was cooled to rt. The reaction mixture was then diluted with 2:1 hexane/EtOAc (6 mL) and passed through a plug of Celite. The filtrate was concentrated in vacuo and the residue was heated in a mixture of isopropanol (15 mL) and water (2 mL). The precipitate which formed was isolated by filtration and dried under vacuum to give a white solid (332 mg, 79%). 5 (R=OMe): mp 173–176° C.; $^1$H NMR (300 MHz, CDCl$_3$) δ 7.12 (s, 28H), 7.11 (d, J=9.0 Hz, 4H), 6.84 (d, J=9.0 Hz, 4H), 3.79 (s, 6H), 1.43 (s, 72H); $^{13}$C NMR (75 MHz, CDCl$_3$) δ 157.6, 153.9, 153.6, 140.8, 140.2, 139.7, 135.8, 128.4, 127.0, 126.9, 114.1, 81.3, 81.2, 81.0, 55.4, 28.2; IR (CDCl$_3$) 1711 cm$^{-1}$; HRMS (FAB) m/z 1666.8244 (1666.8251 calcd for $C_{96}H_{114}N_8O_{18}$, M$^+$); Anal. Calcd for $C_{96}H_{114}N_8O_{18}$: C, 69.13; H, 6.89. Found: C, 69.28; H, 7.11.

General Procedure for Capping of Diamine 10 to Afford 5. A solution of octamer diamine 10 (1.26 g, 1.00 mmol), the appropriate aryl bromide (2.30 mmol), sodium tert-butoxide (240 mg, 2.50 mmol), Pd$_2$(dba)$_3$ (18.7 mg, 0.0204 mmol), and BINAP (38.1 mg, 0.0613 mmol) in THF (10 mL) under Ar was heated to a reflux for 48 h. The heat was then temporarily removed, and 4-DMAP (12.0 mg, 0.100 mmol) and a 1.0 M solution of (BOC)$_2$O (3.50 mmol) in THF (3.50 mL) were added. Heating was resumed for 3 h and then the solution was cooled to rt. The solution was then diluted with 2:1 hexane/EtOAc (10 mL) and passed through a plug of Celite. The filtrate was concentrated in vacuo.

5 (R=H). Obtained as a powder by precipitation from 6:1 MeOH/CHCl$_3$ in 77% yield: mp 171–173° C.; $^1$H NMR (300 MHz, CDCl$_3$) δ 7.30 (t, J=8.7 Hz, 2H), 7.20–7.15 (m, 4H), 7.13 (s, 32H), 1.44 (s, 18H), 1.43 (s, 54H); $^{13}$C NMR (75 MHz, CDCl$_3$) δ 153.7, 153.6, 153.6, 142.8, 140.5, 140.2, 140.0, 128.7, 127.0, 125.7, 81.3, 81.3, 81.2, 28.2; IR (CDCl$_3$) 1711 cm$^{-1}$; HRMS (FAB) m/z 1606.8043 (1606.8037 calcd for $C_{94}H_{110}N_8O_{16}$, M$^+$); Anal. Calcd for $C_{94}H_{110}N_8O_{16}$: C, 70.22; H, 6.90. Found: C, 70.25; H, 6.91.

5 (R=tBu). Obtained as a powder by precipitation from 10:1 EtOH/CHCl$_3$ in 82% yield: mp 172–176° C.; $^1$H NMR (300 MHz, CDCl$_3$) δ 7.30 (d, J=9.0 Hz, 4H), 7.12 (s, 28H), 7.10 (d, J=9.0 Hz, 4H), 1.44 (s, 18H), 1.43 (s, 54H), 1.29 (s, 18H); $^{13}$C NMR (75 MHz, CDCl$_3$) δ 153.8, 153.6, 153.6, 148.6, 140.6, 140.2, 140.1, 139.9, 127.0, 126.3, 125.6, 81.3, 81.3, 81.0, 24.4, 31.3, 28.2; IR (CDCl$_3$) 1713 cm$^{-1}$; HRMS (FAB) m/z 1718.9275 (1718.9292 calcd for $C_{102}H_{126}N_8O_{16}$, M$^+$); Anal. Calcd for $C_{102}H_{126}N_8O_{16}$: C, 71.22; H, 7.38. Found: C, 71.02; H, 7.27.

5 (R=C$_{12}$H$_{25}$). Obtained as a powder by precipitation from 10:1 MeOH/CHCl$_3$ in 82% yield: mp 172–175° C.; $^1$HNMR (300 MHz, CDCl$_3$) δ 7.16–7.08 (m, 36H), 2.57 (t, J=8.0 Hz, 4H), 1.65–1.53 (m, 4H), 1.43 (s, 72H), 1.32–1.20 (m, 36H), 0.88 (t, J=7.3 Hz, 6H); $^{13}$C NMR (75 MHz, CDCl$_3$) δ 153.8, 153.7, 153.6, 140.6, 140.3, 140.2, 139.8, 128.7, 127.0, 126.9, 126.8, 81.3, 81.3, 81.0, 35.4, 31.9, 31.3, 29.6, 29.6, 29.6, 29.5, 29.3, 29.3, 28.2, 27.9, 22.6, 14.1; IR(CDCl$_3$) 1712cm$^{-1}$; Anal. Calcd for $C_{118}H_{158}N_8O_{16}$: C, 72.88; H, 8.19. Found: C, 72.71; H, 8.24.

5 (R=CN). Obtained as a powder by precipitation from MeOH in 79% yield: mp 163–166° C.; $^1$H NMR (300 MHz, CDCl$_3$) δ 7.55 (d, J=9.0 Hz, 4H), 7.31 (d, J=9.0 Hz, 4H), 7.21 (d, J=8.7 Hz, 2H), 7.16–7.13 (m, 24H), 7.08 (d, J=8.7 Hz, 2H), 1.44 (s, 36H), 1.43 (s, 36H); $^{13}$C NMR(75 MHz, CDCl$_3$) δ 153.6, 153.5, 151.6, 147.0, 140.2, 140.1, 140.1, 140.1, 136.9, 132.5, 128.2, 128.0, 127.3, 127.0, 126.7, 125.6, 82.6, 82.2, 81.3, 28.2, 27.9; IR (CDCl$_3$) 1713 cm$^{-1}$; HRMS (FAB) m/z 1656.7952 (1656.7945 calcd for C$_{96}$H$_{108}$N$_{10}$O$_{16}$, M$^+$); Anal. Calcd for C$_{96}$H$_{114}$N$_8$O$_{18}$: C, 69.55; H, 6.57. Found: C, 69.24; H, 6.68.

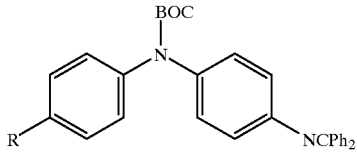

7

Imine 7 (R=OMe). A solution of p-anisidine (1.00 g, 8.13 mmol), bromide 1 (2.60 g, 7.74 mmol), sodium tert-butoxide (1.04 g, 10.8 mmol), Pd$_2$(dba)$_3$ (35.0 mg, 0.0387 mmol), and BINAP (72.0 mg, 0.116 mmol) in THF (25 mL) under Ar was heated to reflux for 18 h. Heating was temporarily stopped, and 4-DMAP (47.0 mg, 0.774 mmol) and a 1.0 M solution of (BOC)$_2$O in THF (11.6 mL) were added. Heating was resumed for 3 h and then the solution was cooled to rt. The reaction mixture was then diluted with 2:1 hexane/EtOAc (25 mL), passed through a plug of Celite, and concentrated in vacuo. The residue was heated in MeOH (40 mL). Cooling of the solution promoted formation of yellow crystals which were isolated by filtration and dried under vacuum (3.11 g, 84%). 7 (R=OMe): mp 148–149° C.; $^1$H NMR (300 MHz, CDCl3) δ 7.73 (d, J=7.1 Hz, 2H), 7.50–7.36 (m, 4H), 7.25 (d, J=6.0 Hz, 2H), 7.11 (d, J=7.1 Hz, 2H), 7.07 (d, J=9.1 Hz, 2H), 6.97 (d, J=8.8Hz, 2H), 6.80 (d, J=9.1 Hz, 2H), 6.65 (d, J=8.8 Hz, 2H), 3.77 (s, 3H), 1.39 (s, 9H); $^{13}$C NMR (75 MHz, CDCl$_3$) δ 168.3, 157.0, 153.9, 148.4, 139.4, 138.5, 130.7, 129.4, 129.2, 128.5, 128.1, 127.8, 127.6, 126.8, 121.2, 113.7, 80.6, 55.4, 28.3; IR (CDCl$_3$) 1705, 1612 cm$^{-1}$; Anal. Calcd for C$_{31}$H$_{30}$N$_2$O$_3$: C, 77.80; H, 6.32. Found: C, 77.77; H, 6.38.

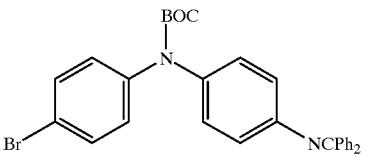

8

Bromide 8 (Method A). A solution of aniline (4.00 mL, 43.9 mmol), bromide 1 (14.1g, 41.8 mmol), sodium tert-butoxide (5.63 g, 58.5 mmol), Pd$_2$(dba)$_3$ (38.2 mg, 0.0418 mmol), and BINAP (62.5 mg, 0.100 mmol) in THF (80 mL) under Ar was heated to reflux for 24 h. After this time, heat was removed and the solution was cooled to rt and then was diluted with EtOAc (80 mL) prior to being washed with 2.0 M NaOH (80 mL). The organic layer was then washed with a saturated solution of NaCl (80 mL), dried over anhydrous Na$_2$SO$_4$, and concentrated in vacuo. The residue was redissolved in CH$_2$Cl$_2$ (88 mL) and treated with tetrabutylammonium tribromide[3] (23.3 g, 48.3 mmol). After stirring the solution for 30 min, a saturated aqueous Na$_2$SO$_3$ solution (80 mL) was added. After the mixture had stirred for another 10 min, it was diluted with 2.0 M NaOH (40 mL), and the layers were separated. The organic layer was washed with a saturated solution of NaCl (80 mL), dried over anhydrous Na$_2$SO$_4$, and concentrated in vacuo. The residue and 4-DMAP (536 mg, 4.39 mmol) were dissolved in THF (50 mL), and a 1.0 M solution of (BOC)$_2$O (57.1 mmol) in THF (57.1 mL) was added. The resulting solution was heated to a reflux for 3 h, cooled to rt, and then was concentrated in vacuo. The residue was heated in MeOH (200 mL). Cooling of the solution afforded yellow crystals (18.7 g, 81%). 8: mp 159–160° C.; $^1$H NMR (300 MHz, CDCl$_3$) δ 7.75 (dd, J=8.5, 1.6 Hz, 2H), 7.50–7.35 (m, 6H), 7.27 (d, J=8.5 Hz, 7.12 (dd, J=7.7, 1.5 Hz, 2H), 7.02 (dd, J=9.0, 2.1 Hz, 2H), 6.94 (d, J=8.5 Hz, 2H), 6.69 (d, J=8.5 Hz, 2H), 1.39 (s, 9H); $^{13}$C NMR (75 MHz, CDCl$_3$) δ 168.8, 153.5, 149.4, 142.3, 139.4, 137.8, 136.1, 131.5, 130.9, 129.5, 129.3, 128.7, 128.2, 127.9, 127.5, 127.4, 121.5, 118.1, 81.2, 28.2; IR (CDCl$_3$) 1710 cm$^{-1}$; Anal. Calcd for C$_{30}$H$_{27}$BrN$_2$O$_2$: C, 68.13; H, 5.16. Found: C, 68.52; H, 5.33.

Bromide 8 (Method B). To a solution of 13 (7.29 g, 14.0 mmol) and sodium acetate (1.15 g, 14.0 mmol) in THF (100 mL) at 0° C. was added Br$_2$ (1.50 mL, 29.1 mmol) dropwise. After 30 min at 0° C. a solution of NaHCO$_3$ (0.5 M) and Na$_2$SO$_3$ (0.5 M) in water was added to the reaction mixture with vigorous stirring. After stirring the mixture for 5 minutes, it was transferred to a separatory funel containing Et$_2$O (50 mL). The phases were separated, and the aqueous phase extracted with Et$_2$O (2×50 mL). The combined organic layers were dried over K$_2$CO$_3$ and concentrated in vacuo, giving a yellow oil which crystallized on standing. Recrystallization from hexane/ethyl acetate afforded pale yellow crystals, 6.55 g (89%).

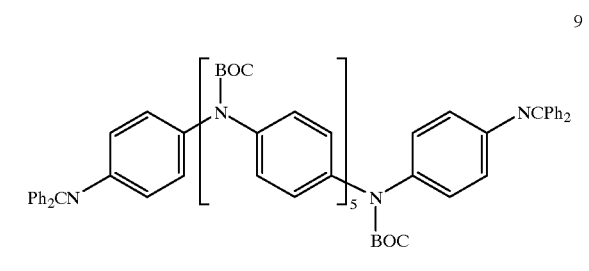

9

Octamer bis-imine 9. A solution of diamine 3 (4.23 g, 8.63 mmol), bromide 8 (9.56 g, 18.1 mmol), sodium tert-butoxide (2.32 g, 24.2 mmol), Pd(OAc)$_2$ (116 mg, 0.518 mmol), and BINAP (376 mg, 0.604 mmol) in THF (43 mL) and triethylamine (11 mL) under Ar was heated to 90° C. After heating the solution for 48 h, the heat was temporarily removed, and 4-DMAP (105 mg, 0.863 mmol), THF (20 mL), and a 1.0 M solution of (BOC)$_2$O (34.5 mmol) in THF (34.5 mL) were added. Heating was resumed at 67° C. and continued for 24 h. The heat was removed, the solution was cooled to rt, and EtOAc (100 mL) and 2.0 M NaOH (60 mL) were added. The mixture was stirred for 15 minutes and then diluted further with EtOAc (100 mL), and water (250 mL). The organic layer was separated, washed with a saturated solution of NaCl (200 mL), dried over anhydrous Na$_2$SO$_4$, and concentrated in vacuo to yield a solid. The solid was heated in a mixture of CHCl$_3$ (20 mL) and isopropanol (200 mL). Cooling of the solution afforded a yellow precipitate. The mother liquor was concentrated in vacuo. The residue was heated in a solution of isopropanol (100 mL) and cooled to precipitate a second crop. The combined solid which formed was isolated by filtration and was dried under vacuum to afford a yellow powder (10.1 g, 74%). 9: mp 154–158° C.; $^1$H NMR (300 MHz, CDCl$_3$) δ 7.74 (d, J=7.0 Hz, 4H), 7.48–7.381 (m, 8H), 7.27–7.23 (m, 8H), 7.11 (s, 16H), 7.08 (s, 4H), 6.95 (d, J=8.4 Hz, 4H), 6.67 (d, J=8.4 Hz, 4H), 1.42 (s, 36 H), 1.38 (s, 18H); $^{13}$C NMR (75 MHz, CDCl$_3$) δ 168.5, 153.6, 153.5, 149.0, 140.5, 140.1, 140.0, 140.0, 139.4, 139.4, 137.9, 136.0, 130.7, 130.7, 129.4, 129.2, 128.6, 128.1, 127.8, 127.4, 126.9, 126.8, 126.0, 121.3, 81.3, 81.3, 81.0, 28.3; IR(CDCl$_3$) 1711 cm$^{-1}$; Anal. Calcd for C$_{98}$H$_{102}$N$_8$O$_{12}$: C, 74.31; H, 6.49. Found: C, 74.36; H, 6.54.

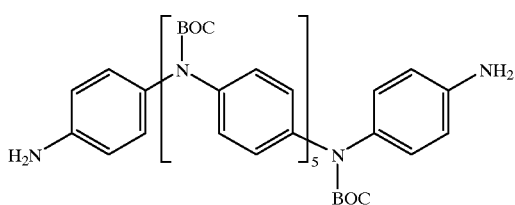

Octamer Diamine 10. A suspension of bis-imine 9 (3.00 g, 1.89 mmol), ammonium formate (2.39 g, 37.9 mmol), and 20% Pd(OH)$_2$ on carbon (0.758 mmol) in THF (50 mL) and EtOH (25 mL) was heated to 70° C. After about 30 min effervescence slowed, and an additional portion of ammonium formate (2.39 g, 37.9 mmol) was added. Ammonium formate was continually added every 60 min until conversion to diamine 10 was complete (as monitored by thin layer chromatography). At this point, the reaction mixture was cooled to rt, diluted with EtOAc (40 mL) and passed through a plug of Celite. The filtrate was diluted with 2:1 hexane/EtOAc (40 mL) and washed with 2.0 M NaOH (40 mL). The organic layer was washed with a saturated solution of NaCl (40 mL), dried over anhydrous Na$_2$SO$_4$, and concentrated in vacuo. The residue was heated in a mixture of hexane (15 mL) and isopropanol (15 mL). Cooling of the solution provided a white precipitate which was isolated by filtration, and dried under vacuum to afford a white powder (2.03 g, 86%). 10: mp 169–172° C.; $^1$H NMR (300 MHz, CDCl$_3$) δ 7.16–7.07 (m, 20H), 6.96 (d, J=8.4 Hz, 4H), 6.60 (d, J=8.4 Hz, 4H), 3.65 (bs, 4H), 1.43 (s, 54 H); $^{13}$C NMR (75 MHz, CDCl$_3$) δ 154.1, 153.6, 153.6, 144.6, 141.0, 140.3, 140.1, 140.0, 139.4, 137.8, 133.7, 128.4, 126.9, 126.9, 126.8, 126.2, 115.1, 81.2, 81.2, 80.7, 28.2, 28.1; IR(CDCl$_3$) 3460, 3369, 1702 cm$^{-1}$; Anal. Calcd for C$_{72}$H$_{86}$N$_8$O$_{12}$: C, 68.88; H, 6.90. Found: C, 68.68; H, 6.84.

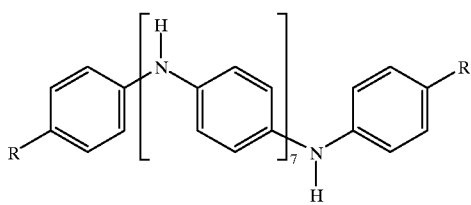

General Procedure for Deprotection of Oligomers (12). Method A[4] (thermolysis): The (solid) protected octamer was placed in a flask under Ar. The system was heated to 185° C. for 9 h. After this time the system was cooled to rt and the powder was removed.

Method B[5] (TMSI): The protected oligomer (0.020 mmol) was dissolved in anhydrous CH$_2$Cl$_2$ (5.0 mL) in a Schienk tube under Ar. Iodotrimethylsilane (20% excess) was added dropwise via syringe, with stirring, causing a pale yellow color to develop. After 15–30 min degassed triethylamine (200 μL) was added, followed by degassed MeOH (200 μL). Within seconds, the clear solution became cloudy and deposited a pale yellow precipitate. After stirring for 30 min, the suspension was cannula-filtered, washing twice with MeOH (5 mL). The collected product was dried in vacuo, affording a white microcrystalline powder.

12 (R=H): mp>300° C.; $^1$H NMR (300 MHz, DMF-d$_7$) δ 7.76 (s, 2H), 7.59 (s, 2H), 7.51 (s, 2H), 7.49 (s, 2H), 7.18 (t, J=7.4 Hz, 4H), 7.10–6.96 (m, 32H), 6.71 (t, J=7.4 Hz, 2H); IR (CDCl$_3$) 3388, 1598, 1514, 1495, 1292, 1214, 814, 744, 697. 509 cm$^{-1}$; UV-vis (NMP) $\lambda_{max}$ 337 nm (ε=6.62×10$^4$); Anal. Calcd for C$_{54}$H$_{46}$N$_8$: C, 80.37; H, 5.75. Found: C, 80.24; H, 5.62.

12 (R=$^t$Bu): mp>300° C.; $^1$H NMR (300 MHz, DMF-d$_7$) δ 7.60 (s, 2H), 7.48 (s, 2H), 7.43 (s, 2H), 7.41 (s, 2H), 7.16 (d, J=8.7 Hz, 4H), 6.93 (d, J=8.7 Hz, 4H), 6.88–6.82 (m, 28H), 1.22 (s, 18H); IR (CDCl$_3$) 3389, 2957, 1610, 1499, 1291, 815 cm$^{-1}$; UV-vis (NMP) $\lambda_{max}$ 336 nm (ε=7.80×104); HRMS (FAB) m/z 918.5090 (918.5097 calcd for C$_{62}$H$_{62}$N$_8$, M$^+$).

12 (R=C$_{12}$H$_{25}$): mp>300° C.; $^1$H NMR (300 MHz, DMF-d$_7$) δ 7.64 (s, 2H), 7.54 (s, 2H), 7.49 (s, 2H), 7.48 (s, 2H), 7.06–6.94 (m, 36H), 2.51 (t, J=7.5 Hz, 4H), 1.61–1.50 (m, 4H), 1.36–1.24 (m, 36H), 0.88 (t, J=6.2, 6H); IR (CDCl$_3$) 3390, 2922, 2852, 1610, 1515, 1498,1293, 1215, 815 cm$^{-1}$; UV-vis (NMP) $\lambda_{max}$ 336 nm (ε=7.34×10$^4$); Anal. Calcd for C$_{78}$H$_{94}$N$_8$: C, 81.92; H, 8.28. Found: C, 81.74; H, 8.09.

12 (R=OMe): mp>300° C.; $^1$H NMR (300 MHz, DMF-d$_7$) δ 7.48 (s, 4H), 7.47 (s, 4H), 7.01 (d, J=8.7 Hz, 4H), 6.99 (s, 28H), 6.84 (d, J=8.7 Hz, 4H), 3.74 (s, 6H); IR (CDCl$_3$) 3389, 1514, 1498, 1292, 1237, 815, 515 cm$^{-1}$; UV-vis (NMP) $\lambda_{max}$ 335 nm (ε=5.38×10$^4$); Anal. Calcd for C$_{56}$H$_{50}$N$_8$O$_2$: C, 77.57; H, 5.81. Found: C, 77.37; H, 5.75.

12 (R=CN): mp>300° C.; $^1$H NMR (300 MHz, DMF-d$_7$) δ 8.60 (s, 2H), 7.79 (s, 2H), 7.58 (d, J=8.4 Hz, 4H), 7.53 (s, 2H), 7.52 (s, 2H), 7.14–6.98 (m, 28H); IR (CDCl$_3$) 3385, 2213, 1602, 1498, 1293, 1237, 1172, 815, 515 cm$^{-1}$; UV-vis (NMP) $\lambda_{max}$ 336 nm (ε=7.34×10$^4$); Anal. Calcd for C$_{56}$H$_{44}$N$_{10}$: C, 78.48; H, 5.17. Found: C, 78.53; H, 4.95.

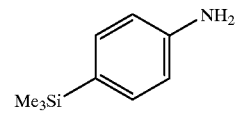

4-(Trimethylsilyl)aniline.[6] Aryl bromide 1 (16.8 g, 50.0 mmol) was dissolved in THF (250 mL) in a dry Schlenk flask under Ar and cooled to −78° C. $^n$BuLi (31.5 mL, 50.4 mmol) was added dropwise, causing the yellow solution to turn deep red. After 20 min TMSCl (6.96 mL, 55.0 mmol) was added dropwise (over 5 min); the red color lightened considerably. Solvent was removed in vacuo; the product was taken up in CH$_2$Cl$_2$, washed with aqueous NaHCO$_3$ (1.0 M), dried over K$_2$CO$_3$, and concentrated in vacuo. The resulting red-orange oil was dissolved in MeOH (100 mL). Sodium acetate (8.20 g, 100 mmol) and hydroxylamine hydrochloride (5.21 g, 75.0 mmol) were added to the rapidly stirring solution. After 5 min, solid K$_2$CO$_3$ (13.8 g, 100 mmol) was added. The mixture was filtered, concentrated in vacuo, and redissolved in CH$_2$Cl$_2$ (30 mL). Cooling to −40° C. resulted in the precipitation of most of the benzophenone oxime, which was removed by filtration. The filtrate was concentrated under reduced pressure and distilled from CaH$_2$ under vacuum, affording a colorless oil (5.42 g, 66%): $^1$H NMR (300 MHz, CDCl$_3$) δ 7.39 (d, J=8.1 Hz, 2H), 6.75 (d, J=8.1 Hz, 2H), 3.75 (s, 2H), 0.29 (s, 9H).

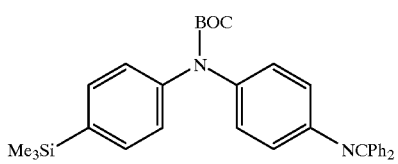

13

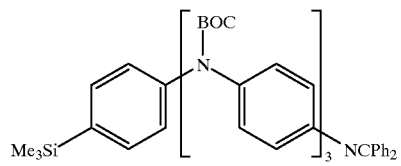

15

13. 4-(Trimethylsilyl)aniline (13.0 g, 78.6 mmol), 1 (25.2 g, 74.8 nunol), NaO$^t$Bu (10.1 g, 105 mmol), Pd$_2$(dba)$_3$ (0.171 g, 0.187 mmol), and BINAP (0.349 g, 0.560 mmol) were dissolved in THF (75 mL) in a Schlenk flask under Ar. The resultant homogeneous red solution was heated to a gentle reflux for 17 h. After this time heating was discontinued; then the solution was cooled to rt, concentrated in vacuo, taken up in CH$_2$Cl$_2$ (200 mL), washed with brine, and dried over K$_2$CO$_3$. The solution was concentrated under reduced pressure to yield an orange solid. This crude product, 4-DMAP (1.64 g, 13.4 mmol), and a 1.0 M solution of (BOC)$_2$O (100 mmol) in THF (100 mL) were heated to a gentle reflux under Ar, causing a rapid evolution of CO$_2$. Heating was discontinued after 2 h. The solution was cooled to rt and concentrated in vacuo to give an orange solid. Recrystallization from MeOH afforded pale yellow crystals (32.9 g, 84%). 13: mp 123–124° C.; $^1$H NMR (300 MHz, CDCl$_3$) δ 7.75 (d, J=7.0 Hz, 2H), 7.49–7.40 (m, 5H), 7.28 (d, J=6.2 Hz, 3H), 7.19 (d, J=8.2 Hz, 4H), 6.98 (d, J=8.5 Hz, 2H), 6.69 (d, J=8.7 Hz, 2H), 1.41 (s, 9H), 0.24 (s, 9H); $^{13}$C NMR (75 MHz, CDCl$_3$) δ 168.8, 154.0, 149.5, 143.9, 139.8, 138.4, 137.0, 136.4, 133.8, 131.0, 129.7, 129.5, 128.8, 128.4, 128.1, 127.9, 125.3, 121.6, 81.1, 28.4, −0.9; IR (CDCl$_3$) 1711 cm$^{-1}$; Anal. calcd for C$_{33}$H$_{36}$N$_2$O$_2$Si: C, 76.11; H, 6.97. Found: C, 76.06; H, 7.18.

14

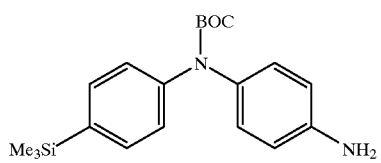

Amine 14. A solution of 3 (3.64 g, 7.00 mmol), ammonium formate (5.30 g, 84.0 mmol), and 10% Pd/C (0.740 g, 0.700 mmol) under Ar in MeOH (100 mL) was heated to 60° C. Heating was discontinued after 45 min. After cooling the reaction mixture to rt, MeOH and some excess ammonium formate were removed in vacuo. The residue was taken up in CH$_2$Cl$_2$, filtered through Celite, and concentrated in vacuo. The resulting white solid was triturated with hexanes (20 mL), cooled to 0° C., and filtered to give white crystals (2.25 g, 90%). 14: mp 108–109° C.; $^1$H NMR (300 MHz, CDCl$_3$) δ 7.42 (d, J=8.5 Hz, 2H), 7.20 (d, J=8.5 Hz, 2H), 7.00 (d, J=8.5 Hz, 2H), 6.64 (d, J=8.5 Hz, 2H), 3.66 (s, 2H), 1.45 (s, 9H), 0.24 (s, 9H); $^{13}$C NMR (75 MHz, CDCl$_3$) δ 154.3, 144.7, 144.1, 136.7, 134.1, 133.7, 128.8, 125.2, 115.4, 80.9, 28.4, −0.9; IR (CDCl$_3$) 1696 cm$^{-1}$; Anal. Calcd for C$_{20}$H$_{28}$N$_2$O$_2$Si: C, 67.38; H, 7.92. Found: C, 67.54; H, 7.99.

15. A solution of 14 (2.35 g, 6.60 mmol), 8 (3.17 g, 6.00 mmol), NaO$^t$Bu (0.807 g, 8.40 mmol), Pd$_2$(dba)$_3$ (54.9 mg, 0.060 mmol), and BINAP (89.7 mg, 0.144 mmol) in toluene (24 mL) was heated with stirring at 80° C. for 19 h under Ar. At this time, heating was discontinued and the solution was cooled to rt. The mixture was diluted with CH$_2$Cl$_2$ (50 mL), and washed with H$_2$O (50 mL). The organic layer was dried over K$_2$CO$_3$ and concentrated in vacuo. The residual solid and 4-DMAP (0.147 g, 1.20 mmol) were dissolved in THF (12 mL) in a Schlenk tube under Ar. A solution of 1.0 M (BOC)$_2$O in THF (12 mL) was added, and the solution was heated to 60° C., resulting in vigorous effervescence. After 2 h of heating, the solution was cooled to rt, and concentrated in vacuo. The residue was heated in MeOH, giving a pale yellow powder (4.63 g, 85%) with cooling. 15: mp 131–133° C.; $^1$H NMR (300 MHz, CDCl$_3$) δ 7.76 (d, J=7.2 Hz, 2H), 7.50–7.42 (m, 5H), 7.28 (m, 3H), 7.19 (d, J=8.1 Hz, 2H), 7.13 (d, J=11.7 Hz, 10H), 6.98 (d, J=8.5 Hz, 2H), 6.69 (d, J=8.5 Hz, 2H), 1.47 (s, 9H), 1.45 (s, 9H), 1.41 (s, 9H), 0.26 (s, 9H); $^{13}$C NMR (75 MHz, CDCl$_3$) δ 169.0, 154.1, 154.0, 149.5, 143.5, 140.8, 140.6, 140.5, 139.8, 138.3, 137.8, 136.4, 134.0, 131.1, 129.8, 129.6, 129.0, 128.5, 128.2, 127.8, 127.5, 127.3, 127.2, 126.4, 126.2, 121.7, 81.6, 81.3, 28.4, −0.9; IR (CDCl$_3$) 1711 cm$^{-1}$; Anal. calcd for C$_{55}$H$_{62}$N$_4$O$_6$Si: C, 73.14; H, 6.92. Found: C, 72.79; H, 6.86.

References for Supporting Information for Example 1

(1) Taguchi, K.; Westheimer, F. H. *J. Org. Chem.* 1971, 36, 1570–1572.
(2) Fasth, K.-J.; Antoni, G.; Langstrom, B. *J. Chem. Soc. Perkin Trans.* 1 1988, 3081–3084.
(3) Berthelot, J.; Guette, C.; Desbene, P.-L.; Basselier, J. J.; Chaquin, P.; Masure, D. *Can. J. Chem.* 1989, 67, 2061–2066.
(4) Rawal, V. H.; Jones, R. J.; Cava, M. P. *J. Org. Chem.* 1987, 52, 19–28.
(5) Lott, R. S.; Chauhan, V. S.; Stammer, C. H. *J. Chem. Soc., Chem. Commun.* 1979, 495–496.
(6) This compound had previously been obtained by an analogous sequence using 4-bromo-N,N-bis(trimethylsilyl)aniline: Walton, D. R. M. *J. Chem. Soc. C* 1966, 1706–1707. We found it more convenient to use the crystalline and moisture-stable N-diphenylmethylene-4-bromoaniline.

Example 2

A. Preparation of Ring-Substituted Monomer Equivalents

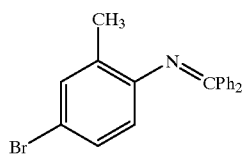

N-Diphenylmethylene-4-bromo-2-methylaniline

Benzophenone (4.89 g, 26.9 mmol), 4-bromo-2-methylaniline (5.00 g, 26.9 mmol), and 5 Å molecular sieves (2.0 g) were placed in a 250 mL round-bottomed flask. Toluene (30 mL) was added, and the flask was fitted with a reflux condenser, purged with argon, and connected to a pressure vent. The reaction mixture was heated to 110° C. with stirring. Analysis by GC after 3.5 d indicated that most of the starting materials had been consumed; no further conversion was observed after an additional 12 h. The mixture was cooled to room temperature, filtered through Celite, and concentrated in vacuo. The residual oil was crystallized from methanol, affording the title compound as yellow crystals, 7.84 g (83%).

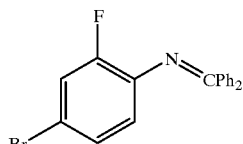

N-Diphenylmethylene-4-bromo-2-fluoroaniline

Benzophenone (4.80 g, 26.3 mmol), 4-bromo-2-fluoroaniline (5.00 g, 26.3 mmol), and 5 Å molecular sieves (2.0 g) were placed in a 250 mL round-bottomed flask. Toluene (30 mL) was added, and the flask was fitted with a reflux condenser, purged with argon, and connected to a pressure vent. The reaction mixture was heated to 110° C. with stirring. Analysis by GC after 2 d indicated that most of the starting materials had been consumed; no further conversion was observed after an additional 12 h. The mixture was cooled to room temperature, filtered through Celite, and concentrated in vacuo. The residual oil was crystallized from methanol, affording the title compound as yellow crystals, 6.82 g (73%).

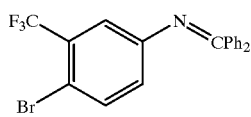

N-Diphenylmethylene-4-bromo-3-trifluoromethylaninline

Benzophenone imine (2.65 mL, 15.8 mL) and 4-bromo-3-trifluoromethylaniline (3.60 g, 15.0 mmol) were placed in a dry 100 mL Schienk flask, which was evacuated, backfilled with argon, and capped with a rubber septum. Dry acetonitrile (25 mL) was added via syringe, followed by methanesulfonic acid (1.00 mL, 15.4 mmol). The resulting red-brown solution was heated with stirring to 75° C.; a white precipitate soon formed. Analysis by GC after 2 h showed the near-complete consumption of the starting aniline. The mixture was cooled to room temperature, taken up in diethyl ether (100 mL), and washed with aqueous sodium hydroxide solution (1 N, 50 mL). The aqueous phase was extracted with two 25-mL portions of diethyl ether. The combined ether extracts were dried over solid potassium carbonate, filtered, and concentrated in vacuo, giving a yellow oil which crystallized on standing. The resulting product was recrystallized from methanol containing a small proportion (<10%) of water, affording the title compound as yellow crystals, 5.344 g (88%)

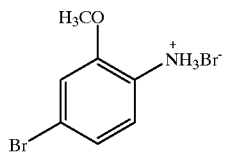

4-Bromo-2-methoxyaninline Hydrobromide

Tetra-n-butylammonium tribromide (9.74 g, 20.2 mmol) was dissolved in dichloromethane (100 mL) in a 250 mL Erlenmeyer flask and cooled to 0° C. A solution of o-anisidine (2.25 mL, 20.0 mmol) in dichloromethane (50 mL) was added via pipette, with stirring, over 5 min; a precipitate formed during the addition. The resulting suspension was stirred for 10 min at 0° C., then the precipitate was collected by filtration and washed with three 10-mL portions of cold dichloromethane. The product consisted of blue-tinged white crystals, 5.432 g (96%). Analysis of a deprotonated solution by GC shows the presence of 2.5% of the starting material, believed to have coprecipitated as the hydrobromide.

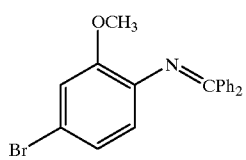

N-Diphenylmethylene-4-bromo-2-methoxyaniline

In a dry 100 mL Schlenk flask, 4-bromo-2-methoxyaniline hydrobromide (4.53 g, 16.0 mmol) was suspended in dry acetonitrile (40 mL) under argon. Benzophenone imine (2.75 mL, 16.4 mmol) was added via syringe. The resulting suspension was heated to 80° C. with stirring. Analysis by GC after 3 h indicated the complete consumption of the starting aniline. The mixture was cooled to room temperature and concentrated in vacuo. The residue was taken up in diethyl ether (100 mL), and washed with aqueous sodium hydroxide solution (2 N, 50 mL). The ether phase was dried over solid potassium carbonate, filtered, and concentrated in vacuo, giving a thick yellow oil. The crude product was purified by flash chromatography on silica gel, using 4:1 hexanes:ethyl acetate as the eluant. The product was obtained as a thick yellow oil which crystallized on standing. Recrystallization from methanol afforded the title compound as yellow crystals, 5.19 g (89%).

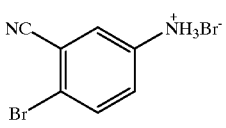

4-Bromo-3-cyanoaniline Hydrobromide

In a 250 mL Erlenmeyer flask, tetra-n-butylammonium tribromide (9.74 g, 20.2 mmol) was dissolved in dichloromethane (100 mL). A solution of 3-aminobenzonitrile (2.36 g, 20.0 mmol) in dichloromethane (100 mL) was added via pipette, with stirring, over 5 min. A precipitate slowly formed. The reaction mixture was stirred at room temperature for 16 h; analysis of a deprotonated aliquot by GC showed the presence of 11% of the starting material. (Previous experiments had indicated that no further reaction takes place on longer stirring or addition of more brominating agent.) The precipitate was collected by filtration and recrystallized three times from ethanol, affording the product as white crystals, 2.94 g (53%). Analysis of a deprotonated solution by GC showed a ratio of product to starting material of 99:1.

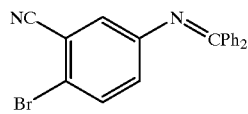

N-Diphenylmethylene-4-bromo-3-cyanoaniline

In a dry 100 mL Schlenk flask, 4-bromo-3-cyanoaniline hydrobromide (2.78 g, 10.0 mmol) was suspended in dry acetonitrile (30 mL) under argon. Benzophenone imine (1.71 mL, 10.2 mmol) was added via syringe. The suspension was heated to 80° C. with stirring. Analysis by GC after 12 h indicated the complete consumption of the starting aniline. The mixture was cooled to room temperature and concentrated in vacuo. The residue was taken up in diethyl ether (100 mL), and washed with aqueous sodium hydroxide solution (2 N, 50 mL). The aqueous phase was extracted with diethyl ether (20 mL). The combined ether portions were dried over solid potassium carbonate, filtered, and concentrated in vacuo, giving yellow crystals. Recrystallization from ethanol afforded the title compound as pale yellow needles, 3.15 g (87%).

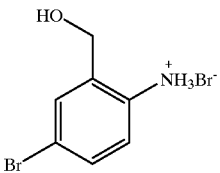

4-Bromo-2-(hydroxymethyl)aniline Hydrobromide

In a 250 mL Erlenmeyer flask, tetra-n-butylammonium tribromide (7.91 g, 16.4 mmol) was dissolved in dichloromethane (100 mL). A solution of 2-aminobenzyl alcohol (2.00 g, 16.2 mmol) in dichloromethane (100 mL) was added via pipette, with stirring, over 5 min. A white precipitate soon formed. The resulting suspension was stirred for 5 min at room temperature, then cooled to 0° C. The precipitate was collected by filtration and washed with two 10-mL portions of cold dichloromethane. The title compound was obtained as white crystals, 3.54 g (63%). Analysis of a deprotonated solution by GC indicated the presence of 5% of the starting material.

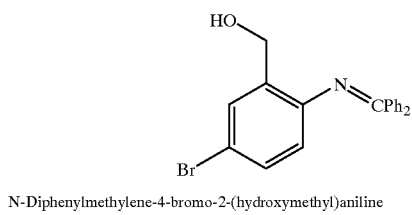

N-Diphenylmethylene-4-bromo-2-(hydroxymethyl)aniline

In a dry 100 mL Schlenk flask, 4-bromo-2-(hydroxymethyl)aniline hydrobromide (3.40 g, 12.0 mmol) was suspended in dry acetonitrile (30 mL) under argon. Benzophenone imine (2.05 mL, 12.2 mmol) was added via syringe. The resulting suspension was heated to 80° C. with stirring. Analysis by GC after 2 h indicated nearly complete consumption of the starting aniline. The mixture was cooled to room temperature and concentrated in vacuo. The residue was taken up in diethyl ether (100 mL), and washed with aqueous sodium hydroxide solution (2 N, 50 mL). The aqueous phase was extracted with diethyl ether (20 mL). The combined ether portions were dried over solid potassium carbonate, filtered, and concentrated in vacuo, giving a thick yellow oil. Crystallization from 9:1 hexanes: ethyl acetate, and recrystallization from ethanol containing a small proportion of toluene afforded the title compound as pale yellow crystals, 3.314 g (75%). It should be noted that the compound decomposes partially under GC conditions, forming a cyclic aminal, but analysis by $^1$H NMR indicates high purity.

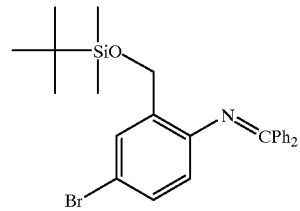

N-Diphenylmethylene-4-bromo-2-(tert-butyldimethylsiloxymethyl)aniline

Imidazole (0.511 g, 7.50 mmol), tert-butyldimethylsilyl chloride (0.543 g, 3.60 mmol), and N-diphenylmethylene-4-bromo-2-(hydroxymethyl)aniline (1.10 g, 3.00 mmol) were placed in a dry 25 mL Schlenk tube, which was evacuated and backfilled with argon. Anhydrous N,N-dimethylformamide (3 mL) was added. The resulting yellow solution was stirred at room temperature. Analysis by GC showed complete consumption of the starting alcohol. The solution was taken up in diethyl ether (75 mL) and washed with aqueous sodium bicarbonate solution (saturated, 50 mL). The ether phase was dried over solid potassium carbonate, filtered, and concentrated in vacuo. The residual oil was purified by flash chromatography on silica gel, using 19:1 hexanes: ethyl acetate as the eluant, to afford the product as a thick yellow oil, 1.29 g (90%).

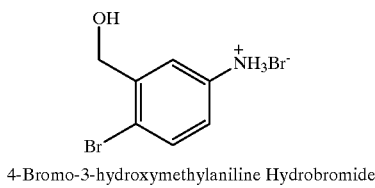

4-Bromo-3-hydroxymethylaniline Hydrobromide

In a 500 mL Erlenmeyer flask, tetra-n-butylammonium tribromide (9.74 g, 20.2 mmol) was dissolved in dichloromethane (50 mL). A solution of 3-aminobenzyl alcohol (2.46 g, 20.0 mmol) in dichloromethane (200 mL) was added via pipette, with stirring, over 5 min. A white precipitate soon formed. The resulting suspension was stirred for 10 min at room temperature. The precipitate was collected by filtration and washed with two 10-mL portions of dichloromethane. The title compound was obtained as white crystals, 5.06 g, containing 5.2% starting material and some minor impurities as judged by GC analysis of a deprotonated solution. Recrystallization of the crude product from ethanol afforded the title compound as white crystals, 3.18 g (56%), of high purity as judged by GC and $^1$H NMR analysis.

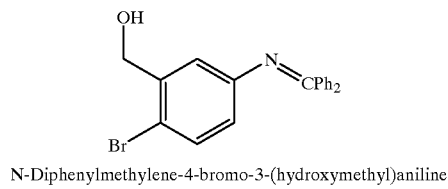

N-Diphenylmethylene-4-bromo-3-(hydroxymethyl)aniline

In a dry 100 mL Schlenk flask, 4-bromo-3-hydroxymethylaniline hydrobromide (2.83 g, 10.0 mmol) was suspended in dry acetonitrile (40 mL) under argon. Benzophenone imine (1.71 mL, 10.2 mmol) was added via syringe. The resulting suspension was heated to 80° C. with stirring. Analysis by GC after 3 h indicated complete consumption of the starting aniline. The mixture was cooled to room temperature and concentrated in vacuo. The residue was taken up in diethyl ether (100 mL), and washed with aqueous sodium hydroxide solution (2 N, 50 mL). Considerable undissolved solid was present; the addition of dichloromethane (150 mL) was necessary to achieve complete dissolution. The organic phase was dried over solid potassium carbonate, filtered, and concentrated in vacuo. The resulting yellow solid was recrystallized twice from ethanol to afford the title compound as yellow crystals, 3.11 g (85%).

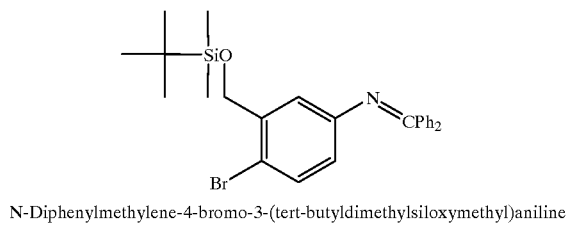

N-Diphenylmethylene-4-bromo-3-(tert-butyldimethylsiloxymethyl)aniline

Imidazole (0.511 g, 7.50 mmol), tert-butyldimethylsilyl chloride (0.543 g, 3.60 mmol), and N-diphenylmethylene-4-bromo-3-(hydroxymethyl)aniline (1.10 g, 3.00 mmol) were placed in a dry 25 mL Schlenk tube, which was evacuated and backfilled with argon. Anhydrous N,N-ditnethylformamide (3 mL) was added. The resulting yellow solution was stirred at room temperature. Analysis by GC showed complete consumption of the starting alcohol. The solution was taken up in diethyl ether (75 mL) and washed with aqueous sodium bicarbonate solution (saturated, 50 mL). The ether phase was dried over solid potassium carbonate, filtered, and concentrated in vacuo. The residual oil was purified by flash chromatography on silica gel, using 19:1 hexanes:ethyl acetate as the eluant, to afford the product as a thick yellow oil, 1.29 g (90%).

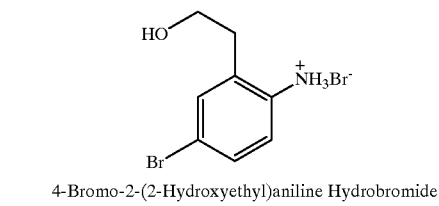

4-Bromo-2-(2-Hydroxyethyl)aniline Hydrobromide

In a 250 mL Erlenmeyer flask, tetra-n-butylammonium tribromide (4.92 g, 10.2 mmol) was dissolved in dichloromethane (30 mL). A solution of 2-aminophenethyl alcohol (1.39 g, 10.1 mmol) in dichloromethane (30 mL) was added via pipette, with stirring, over 5 min. A white precipitate soon formed. The resulting suspension was stirred for 10 min at room temperature, then cooled to 0° C. The precipitate was collected by filtration and washed with two 10-mL portions of cold dichloromethane. The title compound was obtained as white crystals, 2.32 g (78%). Analysis of a deprotonated solution by GC indicated the presence of 5% of the starting material.

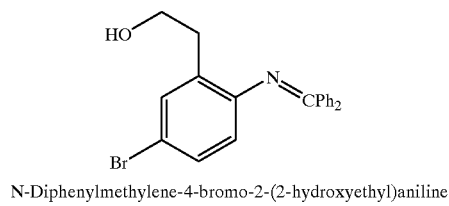

N-Diphenylmethylene-4-bromo-2-(2-hydroxyethyl)aniline

In a dry 100 mL Schlenk flask, 4-bromo-2-(2-hydroxyethyl)aniline hydrobromide (2.08 g, 7.00 mmol) was suspended in dry acetonitrile (25 mL) under argon. Benzophenone imine (1.20 mL, 7.15 mmol) was added via syringe. The resulting suspension was heated to 80° C. with stirring. Analysis by GC after 3 h indicated complete consumption of the starting aniline. The mixture was cooled to room temperature and concentrated in vacuo. The residue was taken up in diethyl ether (100 mL), and washed with aqueous sodium hydroxide solution (2 N, 50 mL). The aqueous phase was extracted with diethyl ether (20 mL). The combined ether portions were dried over solid potassium carbonate, filtered, and concentrated in vacuo. The residue was purified by flash chromatography on silica gel, using 4:1 hexanes:ethyl acetate as the eluant, giving a thick yellow oil which crystallized on standing. The title compound was obtained as yellow crystals, 2.47 g (93%). recrystallization from ethanol containing a small proportion of toluene afforded the title compound as pale yellow crystals, 3.314 g (75%/o). Note that this compound decomposes partially under GC conditions, forming a cyclic aminal. Analysis by $^1$H NMR indicates high purity, except for the presence of 5% of the nonbrominated analogue.

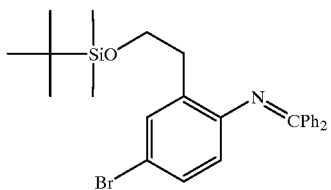

N-Diphenylmethylene-4-bromo-2-(2-tert-butyldimethylsiloxyethyl)aniline

Imidazole (1.04 g, 15.3 mmol), tert-butyldimethylsilyl chloride (1.10 g, 7.32 mmol), and N-diphenylmethylene-4-bromo-2-(2-hydroxyethyl)aniline (1.10 g, 3.00 mmol) were placed in a dry 25 mL Schlenk tube, which was evacuated and backfilled with argon. Anhydrous N,N-dimethylformamide (6 mL) was added. The resulting yellow solution was stirred at room temperature. Analysis by GC showed complete consumption of the starting alcohol. The solution was taken up in diethyl ether (75 mL) and washed with aqueous sodium bicarbonate solution (saturated, 50 mL). The ether phase was dried over solid potassium carbonate, filtered, and concentrated in vacuo. The residual oil was purified by flash chromatography on silica gel, using 19:1 hexanes:ethyl acetate as the eluant, to afford the product as a thick yellow oil, 2.94 g (97%). Analysis by GC indicates the presence of 5% of the nonbrominated analogue.

B. Examples of Ring-Substituted Oligomer Fragments

Note on nomenclature: As these are the first compounds of this general structure, and the IUPAC names for these compounds would generally be extremely awkward, we employ the following informal nomenclature: The oligomer is named according to the number of nitrogen atoms, whether internal or terminal. The standard substitution pattern bears a trimethylsilyl group at the leftmost aryl ring, tert-butyl carbamate protective groups at the internal (secondary) nitrogen atoms, and a diphenylmethylene-protected terminal amine; exceptions are noted. The rings are denoted by letters from the left (C-terminus), and substituents of each ring are numbered with respect to the nitrogen closest to the N-terminus.

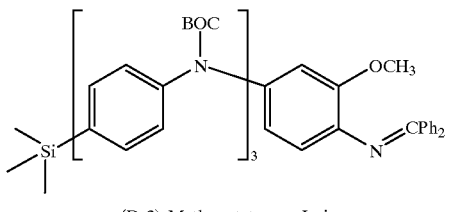

(D-2)-Methoxytetramer Imine

Trimer amine (0.575 g, 1.05 mmol), N-diphenylmethylene-4-bromo-2-methoxyaniline (0.366 g, 1.00 mmol), sodium tert-butoxide (0.135 g, 1.40 mmol), Pd$_2$(dba)$_3$ (4.6 mg, 0.005 mmol, 1 mol % Pd), and 2,2'-bis(diphenylphosphino)phenyl ether (8.1 mg, 0.015 mmol) were placed in a dry 25 mL Schlenk tube, which was evacuated, backfilled with argon, and capped with a rubber septum. Toluene (4 mL) was added via syringe, and the resulting mixture was heated with stirring to 80° C., forming a clear orange solution. Analysis by TLC after 16 h indicated the complete consumption of starting materials. The mixture was cooled to room temperature, taken up in diethyl ether (100 mL), and washed with brine (70 mL). The ether phase was dried over solid potassium carbonate, filtered, and concentrated in vacuo, giving a red-brown oil.

The crude coupling product was transferred to a dry 25 mL Schlenk tube, and 4-dimethylaminopyridine (0.024 g, 0.20 mmol) was added. The flask was evacuated, then backfilled with argon and capped with a rubber septum. Di-tert-butyl dicarbonate (0.29 mL, 1.25 mmol) was added via syringe, followed by tetrahydrofuran (4 mL). The resulting red solution was heated with stirring to 60° C., resulting in a visible effervescence. Analysis of the reaction mixture by TLC after 1.5 h showed the complete consumption of starting material. The mixture was cooled to room temperature and concentrated in vacuo. The resulting solid was crystallized from ethanol, affording the title compound as pale yellow microcrystals, 0.701 g (75%).

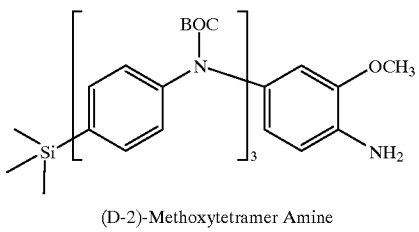

(D-2)-Methoxytetramer Amine

The (D-2)-methoxytetramer imine, ammonium formate (0.349 g, 5.53 mmol), and palladium on carbon (10 wt. %, 0.0583 g, 0.055 mmol Pd) were placed in a dry 25 mL Schlenk tube which was evacuated and backfilled with argon. Methanol (8 mL) was added via syringe, followed by tetrahydrofuran (4 mL). The resulting mixture was heated with stirring to 60° C.; a steady effervescence ensued. Analysis of the reaction mixture after 5 h indicated complete consumption of the starting material. The mixture was cooled to room temperature and concentrated in vacuo. The residue was taken up in dichloromethane (50 mL) and filtered through Celite; the resulting solution was concentrated in vacuo. The residual solid was triturated with hexanes (20 mL), affording the title compound as a white solid, 0.393 g (93%).

C. Synthesis of Protected Polyaniline Using Palladium Catalysis

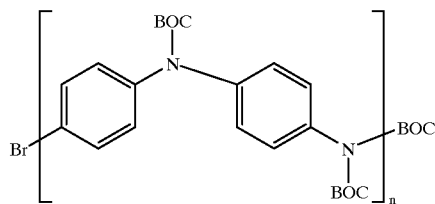

Poly(N-tert-butoxycarbonyl) aniline

A dry 25 mL Schlenk tube was charged with 4-bromo-4'-amino-N-(tert-butoxycarbonyl)diphenylamine (0.363 g, 1.00 mmol), sodium tert-butoxide (0.1345 g, 1.40 mmol), Pd$_2$(dba)$_3$ (4.6 mg, 0.005 mmol, 1 mol % Pd), and (rac)-BINAP (9.3 mg, 0.015 mmol). The tube was evacuated and backfilled with argon, then capped with a rubber septum. Toluene (3 mL) was added via syringe, and the resulting mixture was heated with stirring to 80° C., giving a clear red solution. After 24 h, the reaction mixture was cooled to room temperature and concentrated in vacuo. The residual solid was pulverized in a mortar and pestle, then collected in a fritted funnel and washed with diethyl ether (20 mL), water (20 mL), isopropyl alcohol (5 mL), and diethyl ether (20 mL). The crude polymerization product was obtained as a gray powder, 0.252 g (89% assuming complete consumption of aryl bromide).

The crude product and 4-dimethylaminopyridine (0.024 g, 0.20 mmol) were placed in a dry 25 mL Schlenk tube, which was evacuated, backfilled with argon, and capped with a rubber septum. Tetrahydrofuran (10 mL) was added via syringe, forming a fine suspension. The mixture was sonicated for 10 min, then di-tert-butyl dicarbonate (0.32 mL, 1.4 mmol) was added via syringe. The resulting mixture was heated with stirring to 60° C., resulting in a visible effervescence.

After 14 h, the reaction mixture was cooled to room temperature and concentrated in vacuo. The residue was taken up in dichloromethane (160 mL), and washed with aqueous ammonium chloride solution (saturated, 60 mL), aqueous sodium hydroxide solution (1 N, 60 mL), and brine (60 mL). A considerable quantity of a rubbery pink solid was observed; when removed from the mixture, this material failed to dissolve to any observable degree in dichloromethane. Analysis of this material by IR spectroscopy indicates that it consists of incompletely protected polymer.

The organic solution was dried over solid potassium carbonate, filtered through Celite and concentrated in vacuo. The resulting red solid was dissolved in dichloromethane and reprecipitated by the addition of ethanol to the boiling solution followed by cooling. The product was isolated as pale pink microcrystals, 0.167 g (44%). Analysis by $^1$H NMR shows a single aryl resonance and a single tert-butyl resonance, consistent with an average degree of polymerization of over 20: In shorter polymers, the two N-terminal BOC groups display a resonance distinct from that of the internal BOC groups. Analysis by GPC (calibrated against polystyrene standards) indicates a weight-average molecular weight of 45,300, and a number-average molecular weight of 11,400; the latter corresponds to an average chain length of approximately 60 aniline units (n=ca. 30).

Example 3

Palladium-Catalyzed Synthesis of Monodisperse, Controlled-Length and Functionalized Oligoanilines The palladium-catalyzed amination of aryl halides, in conjunction with an orthogonal protective group scheme, forms the basis of two routes to oligoaniline precursors. One method consists of a bidirectional chain growth from a symmetric core piece, whereas the other involves a divergent-convergent synthesis of nonsymmetric fragments, followed by coupling to a symmetric core fragment. The oligoaniline precursors are soluble in a variety of common organic solvents, and are easily converted to the deprotected oligoanilines. The method allows the preparation of even or odd chain lengths, and the incorporation of a variety of functional groups. The synthesis of phenyl-capped heptaaniline through decaaniline, of four end-functionalized octaaniline derivatives, and of phenyl-capped 16-mer and 24-mer, is described. The effects of chain length and substitution upon oligomer behavior have been investigated by electronic absorption spectroscopy and cyclic voltammetry.

Introduction

Well over a century after the first oxidation of aniline,[1] the electrical conductivity of polyaniline was recognized.[2] Among conductive polymers, polyaniline is remarkable for its excellent environmental stability,[3] and unique in the ease with which its properties may be tuned by changes in oxidation state[4] or in degree of protonation.[5] Advances in the electropolymerization of aniline,[6] and in solution-processing of the chemically synthesized polymer,[7] have allowed the study of polyaniline in numerous practical applications, including rechargeable organic batteries,[8] electrochromic displays,[9] electromechanical actuators,[10] anti-corrosion coatings for steel,[11] and electromagnetic interference shielding.[12]

Soon after polyaniline was identified as an electrical conductor, Honzl et al. prepared and investigated the first phenyl-capped oligoanilines of controlled chain length as models for the poorly defined polymer.[13] The synthetic method involved the condensation of small oligoanilines (dimer, trimer and tetramer)[14] with diethyl succinoylsuccinate, followed by hydrolysis, decarboxylation, and aromatization. This sequence afforded phenyl-capped tetraaniline and hexaaniline; diazotization and reduction of tetraaniline gave rise to phenyl-capped trianiline. The authors apparently did not isolate phenyl-capped octaaniline from the condensation reaction when tetraaniline was used.

In 1986, Wudl and coworkers modified the Honzl condensation approach and succeeded in obtaining phenyl-capped octaaniline.[15] This compound proved identical to bulk polyaniline by ESR, UV-vis, and IR spectroscopy, and displayed conductivity on the same order of magnitude as that of the bulk polymer, demonstrating that useful electrical properties may be realized even in relatively short oligoaniline systems.

More recently, other methods for the synthesis of oligoanilines have been reported. A titanium alkoxide-mediated coupling of anilines with phenols has been used to prepare phenyl-capped tetraaniline and pentaaniline.[16] An Ullmann coupling reaction between acetanilides and 4-iodonitrobenzene was used in an iterative coupling/reduction sequence, followed by deacetylation to afford trianiline and tetraaniline, the starting anilines for the Wudl-Honzl oligoaniline synthesis.[17] Finally, in a modem variant of the Wilstätter-Moore approach,[14] MacDiarmid, Epstein et al. have oxidized N-phenyl-1,4-phenylenediamine to tetraaniline; they report that oxidation of the latter compound affords a 16-mer.[18]

The palladium-catalyzed amination of aryl halides and triflates[19] has emerged as a powerful method for the synthesis of a wide variety of arylamines. The high efficiency and broad substrate scope of the reaction make it an ideal method for the preparation of novel oligoaniline derivatives. We have developed a general route to oligoanilines, using palladium catalysis to assemble the aryl-nitrogen framework and an orthogonal protective group scheme to control the course of the reactions. The protective groups confer excellent solubility upon the products, and are easily removed to form the electroactive oligomers. This method offers great synthetic flexibility: even- or odd-numbered oligomers may be prepared, and functional groups may be introduced at the ends of the chains to modify the properties of the materials without disrupting the coplanarity between rings. We have prepared and investigated phenyl-capped heptaaniline through decaaniline, a series of end-functionalized octamers, and the phenyl-capped 16-mer and 24-mer.

Results and Discussion

Oligomer Synthesis. The simplest palladium-catalyzed synthesis of polyaniline would involve the polymerization of 4-bromoaniline, or the copolymerization of 1,4- phenylenediamine with 1,4-dibromobenzene. However, the coupling products would be easily oxidized, even short oligomers would present problems in solubility and purification, and precise control over chain length would be difficult.

Several strategies,[20] illustrated in Scheme 1, may be envisioned for the synthesis of discrete oligoanilines by sequences of aryl amination and deprotection. The reaction of an arylamine with a protected 4-bromoaniline, followed by deprotection, would result in an increase in chain length of one unit for each iteration. The disadvantages of such a method are the relatively slow increase in chain length for a given number of steps, and the increasing difficulty of separating the products from any unreacted starting material or byproducts as the chain length increases. An outward growth of the oligoaniline from a symmetric core would permit the chain to grow by two units in one iteration, and result in a larger difference in size between starting material and desired product. As in the monodirectional strategy, the chain length increases by the same increment with each iteration of the sequence.

A geometric growth in chain length is possible using a divergent-convergent approach.[21] In this strategy, a suitably protected oligomer is divided into two portions; one is converted to an arylamine, and the other to an aryl bromide. The coupling of the two produces a homologous oligomer, with a doubling in chain length.

Scheme 1
Possible strategies for the synthesis of oligoanilines by aryl amination.

Monodirectional Growth:

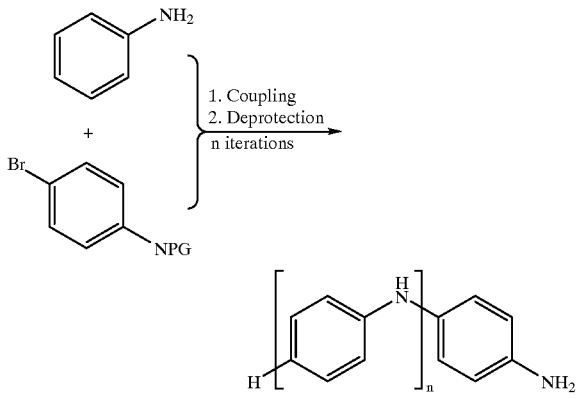

Bidirectional Growth:

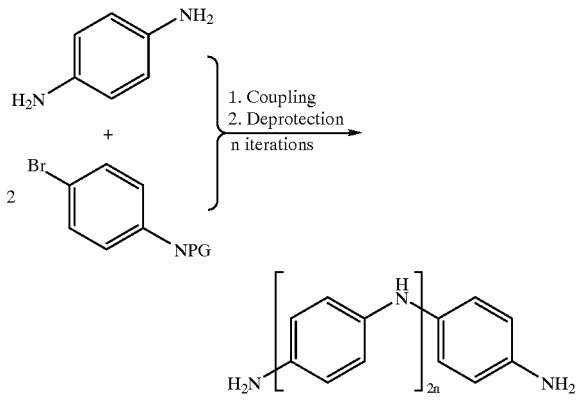

Divergent-Convergent Growth:

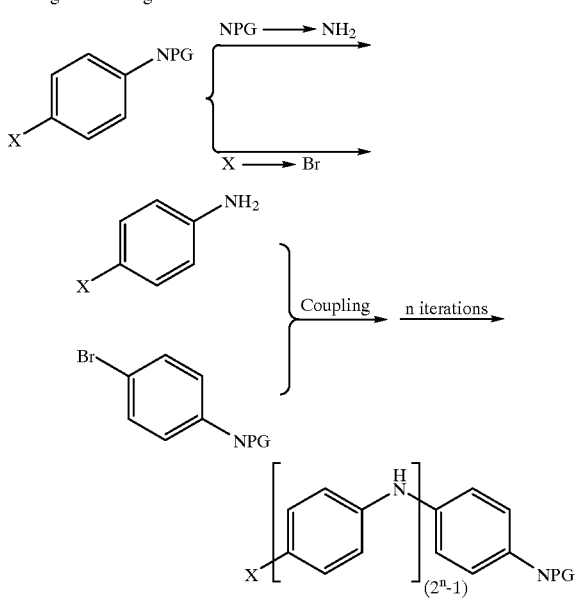

For electrochemical studies and applications of oligoanilines, symmetric products are desirable, to avoid the complications of parallel and antiparallel orientations between chains. Our synthetic methods combine the divergent-convergent approach with a modified bidirectional approach, which links the chain fragments to form a symmetric oligomer. This strategy requires the use of suitable equivalents for the aryl bromide and arylamine functional groups, so that each may be unmasked without affecting the other.

The facile electrophilic substitution of the trimethylsilyl group[22] allows it to function as a masked aryl bromide. The nitrogen protecting group was therefore required to be stable to the reaction conditions of bromodesilylation, as well as to those of aryl amination, and to be removable without the use of strong acid, which would cleave the aryl-silicon bond.

After investigating a number of possibilities, we found the diphenylmethylene group to be extremely useful for several reasons. Condensation of 4-bromoaniline with benzophenone is easily carried out on large scale and in high yield. The resulting N-(diphenylmethylene)-4-bromoaniline (1) is a convenient substrate for palladium-catalyzed aryl amination; the reactions proceed rapidly and cleanly, with no detectable transamination, and the diphenylmethylene group imparts excellent crystallinity to the products. This protective group is stable to bromine under the conditions used in bromodesilylation. The free primary amine may be liberated by hydrogenolysis,[23] or by treatment with hydroxylamine under weakly acidic conditions.[24] Finally, the stability of the imine to alkyllithium reagents at low temperature allows halogen-metal exchange to be carried out on 1, leading to a convenient preparation of 4-(trimethylsilyl)aniline (2).[25] The preparation of 4-bromoaniline equivalents 1 and 2 is outlined in Scheme 2.

Scheme 2[a]

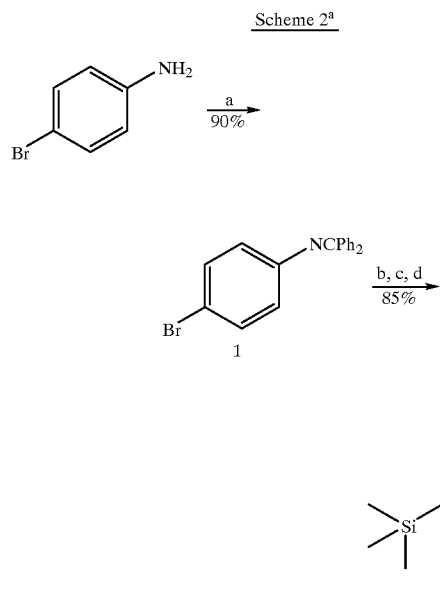

[a]Key:
(a) Ph$_2$CO, 5Å mol. sieves, PhCH$_3$, 120° C.;
(b) n-C$_4$H$_9$Li, THF, -78° C.;
(c) (CH$_3$)$_3$SiCl, THF, -78° C.;
(d) H$_2$NOH·HCl (1.5 eq), NaOAc (2 eq), CH$_3$OH.

Palladium-catalyzed coupling of 1 and 2 affords an aniline dimer with a masked bromide at one end and a protected amine at the other. Protection of the internal NH group as its tert-butyl carbamate (BOC) derivative forms a dimer derivative (3) which may be homologated by the divergent-convergent approach. The tert-butyl carbamate confers excellent solubility upon intermediates and products, prevents the oxidation of the phenylenediamine moieties in higher oligomers to quinonediimines, and allows bromodesilylation to occur without detectable overbromination. The divergent-convergent process is easily carried out on multigram scale; the yield for each step is high, and the intermediates are easily purified by crystallization. Scheme 3 shows the synthesis of several chain fragments (5, 7, 10) used in the preparation of symmetric oligomers.

Scheme 3[a]

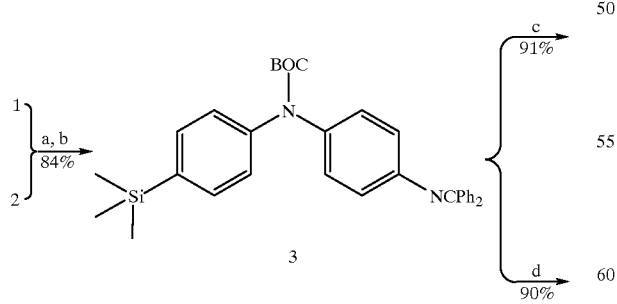

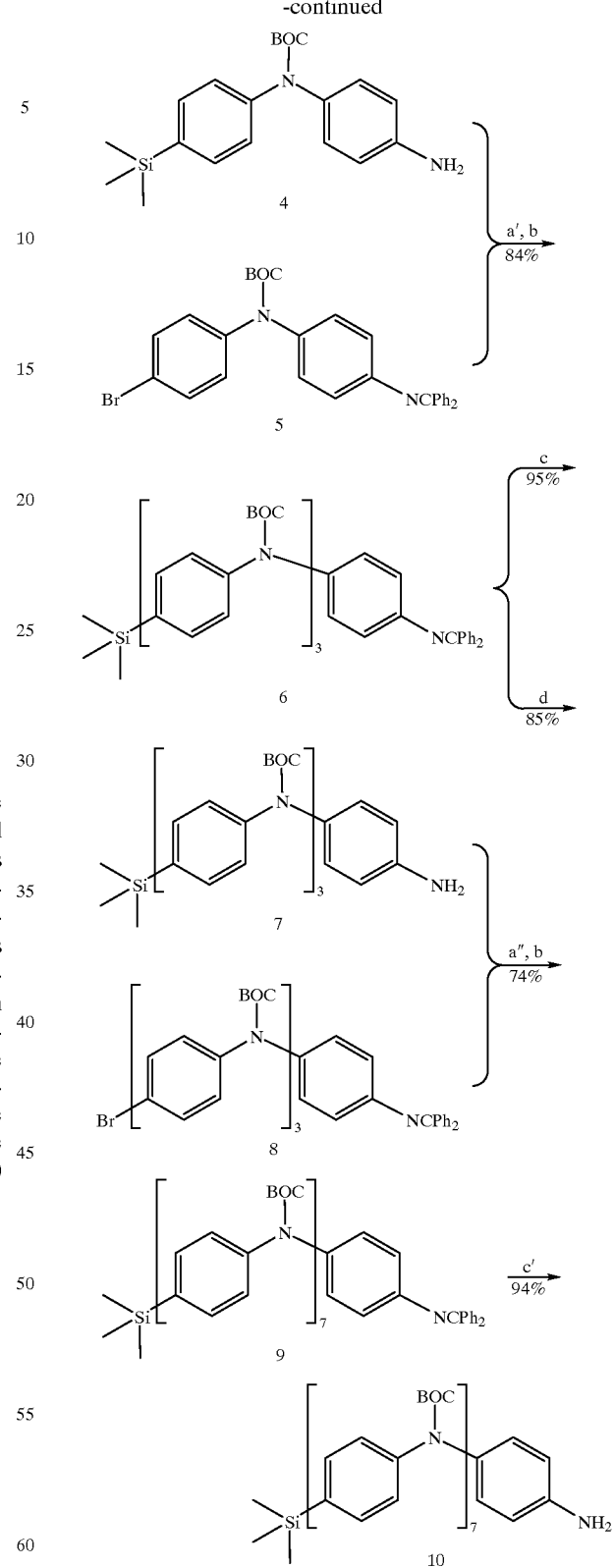

-continued

<sup>a</sup>Key:
(a) Pd<sub>2</sub>(dba)<sub>3</sub> (0.25 mol%), S-BINAP[26] (0.75 mol%), NaOtBu (1.4 eq), THF, reflux; (a′) Pd<sub>2</sub>(dba)<sub>3</sub> (1 mol%), S-BINAP (2.4 mol%), NaOtBu (1.4 eq), toluene, 80° C.; (a″) Pd<sub>2</sub>(dba)<sub>3</sub> (2 mol%), S-BINAP (4.8 mol%), NaOtBu (1.4 eq), toluene, 80° C.;
(b) (BOC)<sub>2</sub>O (1.3 eq), 4-DMAP (0.2 eq), THF, reflux;
(c) NH<sub>4</sub><sup>+</sup>HCO<sub>2</sub><sup>−</sup> (12 eq), 10% Pd/C (0.1 eq Pd), THF/CH<sub>3</sub>OH, 60° C.; (c′) NH<sub>4</sub><sup>+</sup>HCO<sub>2</sub><sup>−</sup>(>30 eq), 20% Pd(OH)<sub>2</sub>/C (0.5 eq Pd), iPrOH, 80° C.;
(d) NaOAc (1 eq), Br<sub>2</sub> (2 eq), THF, -78° C. to 0° C..

Other nonsymmetric chain fragments may be prepared by modifications of this synthetic methodology; the synthesis of a trimer derivative (12) is shown in Scheme 4. The synthesis of aryl bromide 14 (Scheme 5) is noteworthy for the selective monoamination of 1,4-dibromobenzene; the highly electron-rich coupling product 13.2 reacts so slowly with the palladium catalyst that, under these conditions, the amination stops cleanly at this stage. Protection of the secondary amine as its BOC derivative results in an aryl bromide substrate (14) which is activated toward oxidative addition.

Scheme 4<sup>a</sup>

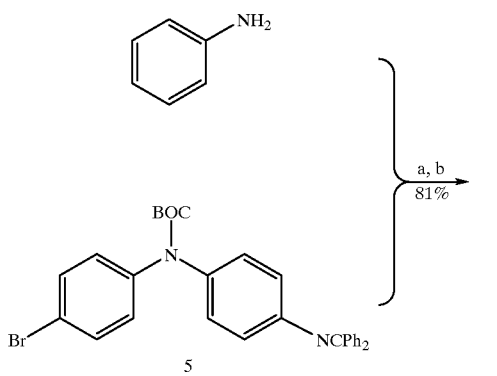

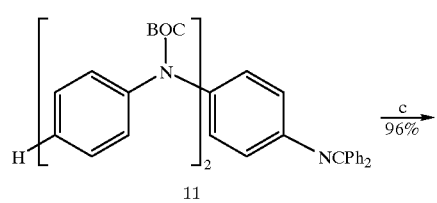

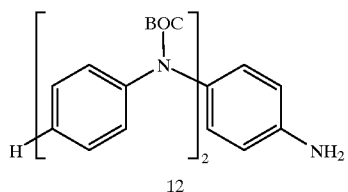

<sup>a</sup>Key:
(a) Pd<sub>2</sub>(dba)<sub>3</sub> (1 mol%), S-BINAP (2.5 mol%), NaOtBu (1.4 eq), toluene, 80° C.;
(b) (BOC)<sub>2</sub>O (1.5 eq), 4-DMAP (0.2 eq), THF, 60° C.;
(c) 5% Pd/C (0.1 eq Pd), NH<sub>4</sub><sup>+</sup>HCO<sub>2</sub><sup>−</sup>(15 eq), THF/CH<sub>3</sub>OH, 60° C..

Scheme 5<sup>a</sup>

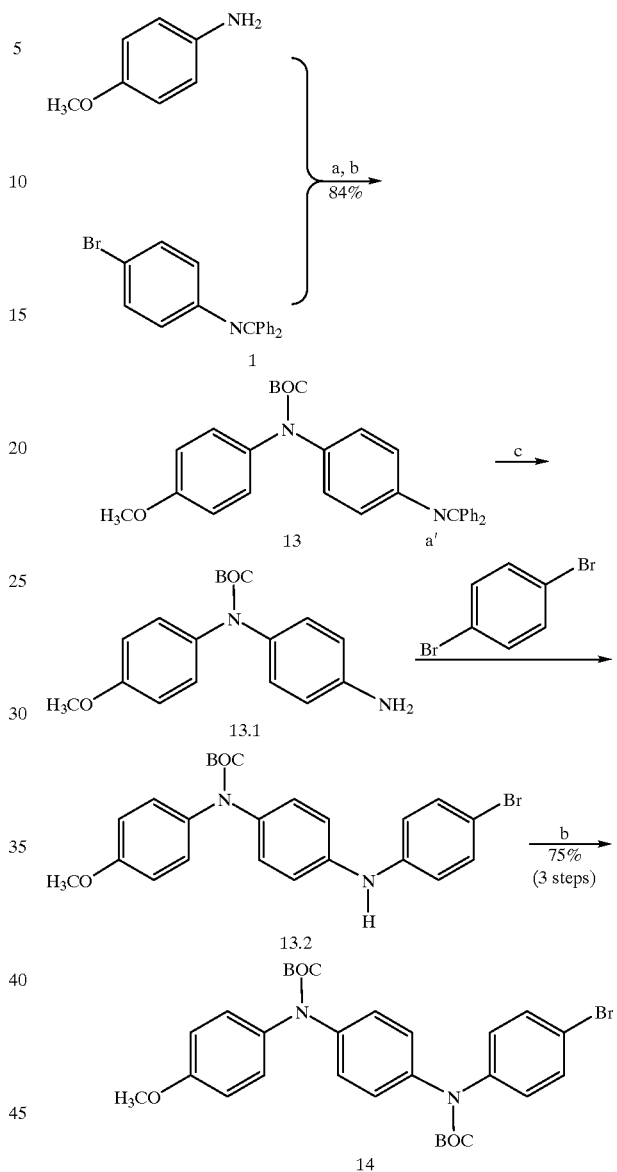

<sup>a</sup>Key:
(a) Pd<sub>2</sub>(dba)<sub>3</sub> (0.5 mol%), S-BINAP (1.5 mol%), NaOtBu (1.4 eq), THF, reflux;
(a′) Pd<sub>2</sub>(dba)<sub>3</sub> (1 mol%), S-BINAP (3 mol%), NaOtBu (1.4 eq), THF, reflux;
(b) (BOC)<sub>2</sub>O (1.5 eq), 4-DMAP (0.1 eq), THF, reflux; (c) 20% Pd(OH)<sub>2</sub>/C (0.1 eq Pd), NH<sub>4</sub><sup>+</sup>HCO<sub>2</sub><sup>−</sup>(20 eq), EtOH, 60° C..

The synthesis of substituted octamers 18 was carried out by the bidirectional approach illustrated in Scheme 6. The symmetric N<sub>4</sub>-diamine 15 is obtained by the reaction of 1,4-phenylenediamine with two equivalents of monomer 1, followed by BOC-protection and imine cleavage.[27] Iteration of the sequence using aryl bromide 5 allows more rapid growth, giving the N<sub>8</sub>-diamine 17. This diamine reacts with simple aryl bromides to give a variety of α-ωdisubstituted phenyl-capped octamers (18a–d) from a common precursor. Alternatively, the N<sub>4</sub>-diamine 15 may be converted directly to a capped octamer by reaction with the appropriate N₂-aryl bromide, as in the synthesis of the bis(methoxy)-substituted octamer (18e).

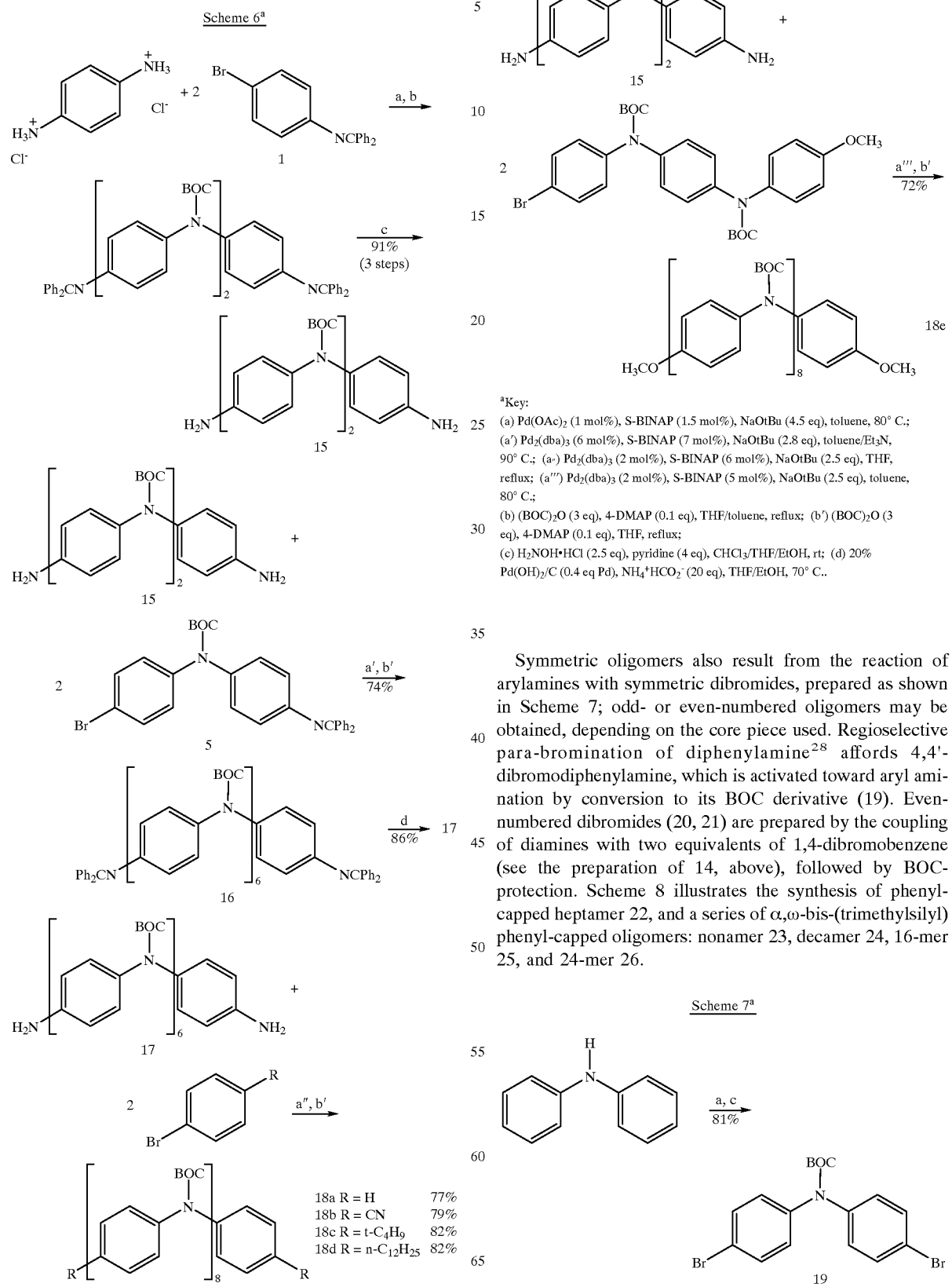

ᵃKey:
(a) Pd(OAc)₂ (1 mol%), S-BINAP (1.5 mol%), NaOtBu (4.5 eq), toluene, 80° C.;
(a′) Pd₂(dba)₃ (6 mol%), S-BINAP (7 mol%), NaOtBu (2.8 eq), toluene/Et₃N, 90° C.; (a″) Pd₂(dba)₃ (2 mol%), S-BINAP (6 mol%), NaOtBu (2.5 eq), THF, reflux; (a‴) Pd₂(dba)₃ (2 mol%), S-BINAP (5 mol%), NaOtBu (2.5 eq), toluene, 80° C.;
(b) (BOC)₂O (3 eq), 4-DMAP (0.1 eq), THF/toluene, reflux; (b′) (BOC)₂O (3 eq), 4-DMAP (0.1 eq), THF, reflux;
(c) H₂NOH•HCl (2.5 eq), pyridine (4 eq), CHCl₃/THF/EtOH, rt; (d) 20% Pd(OH)₂/C (0.4 eq Pd), NH₄⁺HCO₂⁻ (20 eq), THF/EtOH, 70° C..

Symmetric oligomers also result from the reaction of arylamines with symmetric dibromides, prepared as shown in Scheme 7; odd- or even-numbered oligomers may be obtained, depending on the core piece used. Regioselective para-bromination of diphenylamine[28] affords 4,4′-dibromodiphenylamine, which is activated toward aryl amination by conversion to its BOC derivative (19). Even-numbered dibromides (20, 21) are prepared by the coupling of diamines with two equivalents of 1,4-dibromobenzene (see the preparation of 14, above), followed by BOC-protection. Scheme 8 illustrates the synthesis of phenyl-capped heptamer 22, and a series of α,ω-bis-(trimethylsilyl) phenyl-capped oligomers: nonamer 23, decamer 24, 16-mer 25, and 24-mer 26.

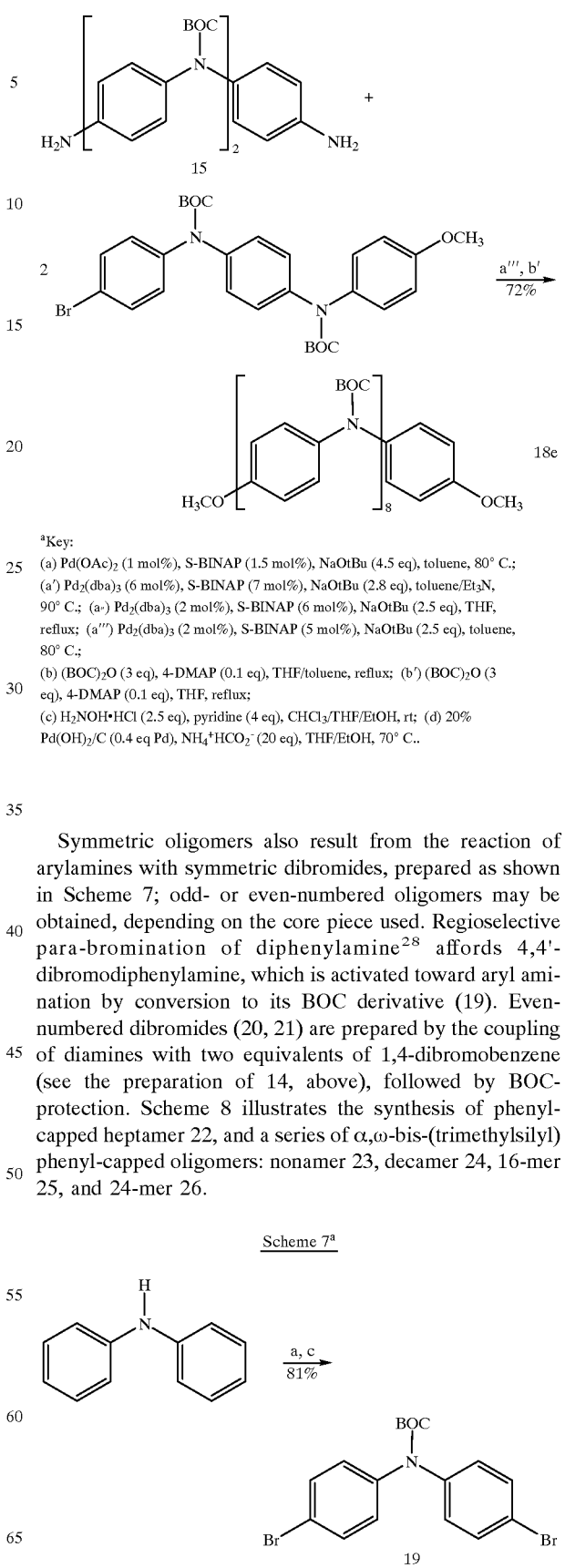

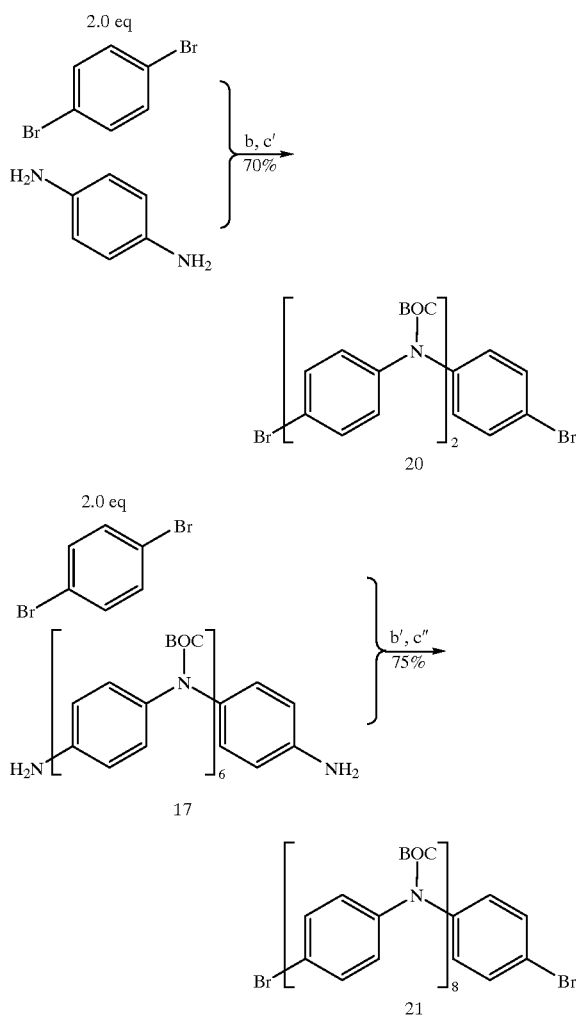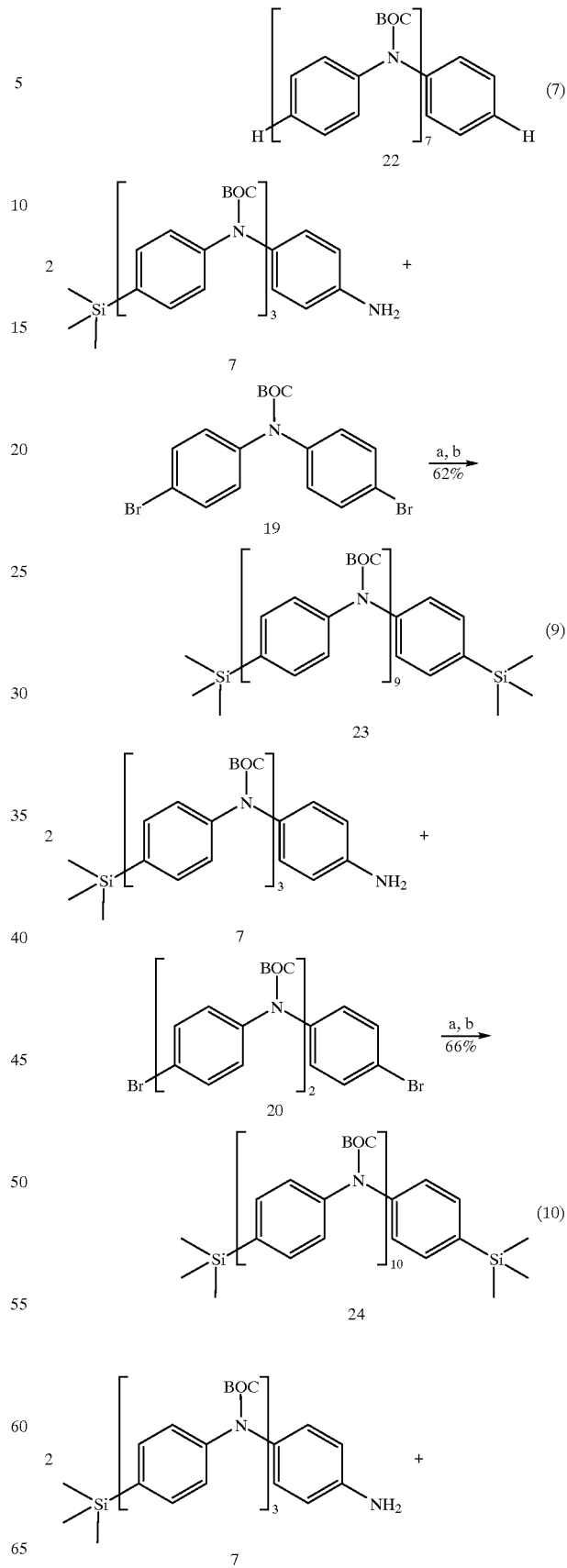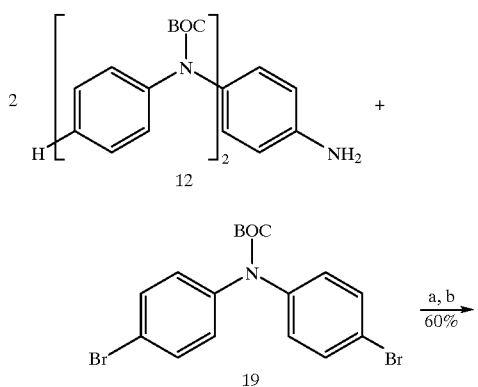
Scheme 8[a]
[a]Key: (n-C$_4$H$_9$)$_4$N$^+$Br$_3^-$ (2 eq), CH$_2$Cl$_2$, rt, 5 min; (b) Pd$_2$(dba)$_3$ (1.2 mol%), S-BINAP (3.7 mol%), NaOtBu (2.6 eq), THF, reflux; (b′) Pd(OAc)$_2$ (4 mol%), S-BINAP (4.8 mol%), NaOtBu (2.6 eq), toluene/Et$_3$N, 90° C.; (c) (BOC)$_2$O (1.1 eq), 4-DMAP (0.2 eq), THF, reflux; (c′) (BOC)$_2$O (3.5 eq), 4-DMAP (0.2 eq), THF, reflux; (c″) (BOC)$_2$O (3.5 eq), 4-DMAP (0.1 eq), THF/toluene/Et$_3$N, 67° C..

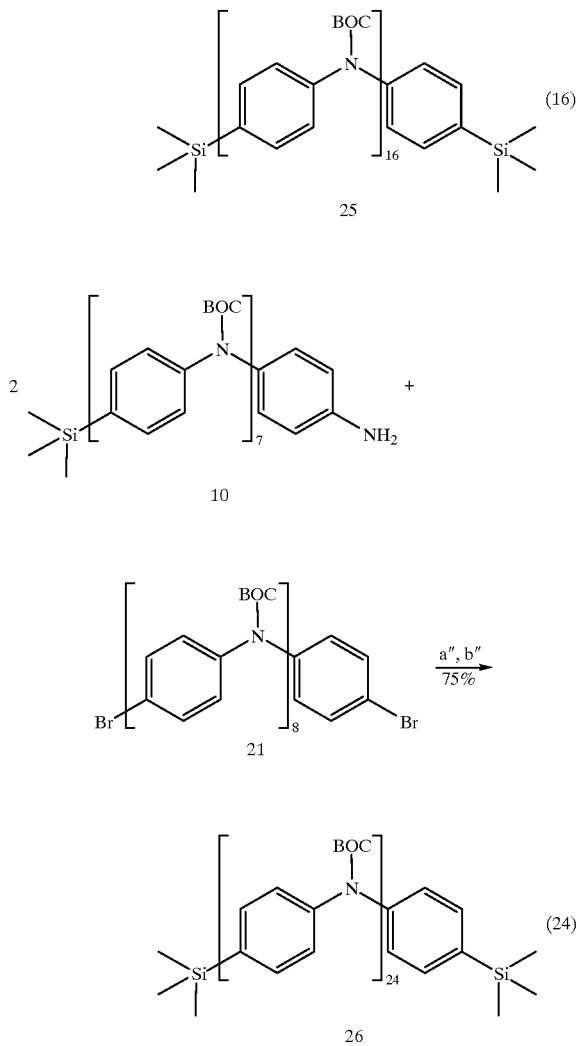

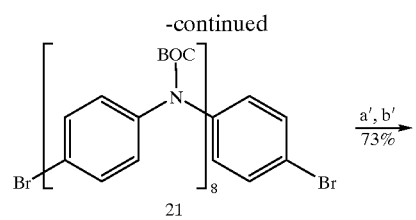

<sup>a</sup>Key:
(a) Pd(dba)₃ (2 mol%), S-BINAP (4.8 mol%), NaOtBu (2.9 eq), toluene, 80° C.;
(a') Pd(OAc)₂ (4 mol%), S-BINAP (4.8 mol%), NaOtBu (2.8 eq), toluene/Et₃N, 90° C.; (a'') Pd(OAc)₂ (6 mol%), S-BINAP (7.2 mol%), NaOtBu (3 eq), toluene/Et₃N, 90° C.;
(b) (BOC)₂O (2.5 eq), 4-DMAP (0.5 eq), THF, 60° C.; (b') (BOC)₂O (3.5 eq), 4-DMAP (0.1 eq), THF, toluene/Et₃N, 67° C.; (b'') (BOC)₂O (4 eq), 4-DMAP (0.2 eq), THF/toluene/Et₃N, 67° C.;

The protected oligomers exhibit good solubility in numerous common solvents; they are moderately soluble in tetrahydrofuran and hot alcohols, highly soluble in toluene, and extremely soluble in dichloromethane and chloroform. Removal of the tert-butyl carbamate groups decreases the solubility of the materials considerably; however, the deprotected oligoanilines are sufficiently soluble in polar aprotic solvents such as N,N-dimethylformamide and N-methylpyrrolidinone to permit their characterization by UV-vis spectroscopy, and the casting of films or electrochemical studies. Deprotected oligoanilines as long as the decamer could be characterized by $^1$H NMR. To examine the solubilizing influence of alkyl groups at the termini of oligoanilines, we prepared the bis(tert-butyl)- and bis(n-dodecyl)-substituted octaanilines 27c and 27d, but these exhibited the same solubility as the other oligoanilines. In any case, the facile cleavage of the BOC groups allows them to function as removable solubilizing groups.

Oligomer Deprotection.

Thermolysis of the protected oligomers under an inert atmosphere results in clean and quantitative removal of the BOC group,[29] affording the oligoaniline in its lowest oxidation state as shown in Scheme 9. Infrared spectroscopy of a thin film of 18a on a NaCl plate, heated under argon at 185° C., showed that the complete disappearance of the carbonyl absorption required a reaction time of approximately 7 hours. Likewise, $^1$H NMR spectroscopy of 18a, heated at 185° C. in DMSO-d₆ solution, indicated a reaction time of nearly 7 hours for the complete loss of the tert-butyl resonance. The preparation of aoctaanilines 27a–e was accomplished by heating the powders in Schlenk tubes under argon for 9 hours.

Scheme 9

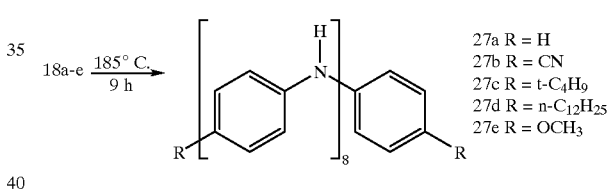

27a R = H
27b R = CN
27c R = t-C₄H₉
27d R = n-C₁₂H₂₅
27e R = OCH₃

Alternatively, the BOC group may be cleaved using iodotrimethylsilane. The protected oligomers react rapidly with iodotrimethylsilane to form the corresponding trimethylsilyl carbamates.[30] The trimethylsilyl carbamate group confers the same solubility as the tert-butyl carbamate, but is extremely labile in the presence of moisture or protic solvents. For preparative purposes, a solution of the trimethylsilyl carbamate is prepared in dichloromethane; subsequent addition of excess methanol causes the deprotected oligoaniline to precipitate immediately. Phenyl-capped heptaaniline (28), nonaaniline (29), decaaniline (30), 16-mer (31), and 24-mer (32) were prepared by this method, as shown in Scheme 10. Note that the acid generated upon reaction of the remaining iodotrimethylsilane with methanol effects the protodesilylation of arylsilanes 23–26 in the same operation. Octaanilines prepared by this method were analytically and spectroscopically identical to those prepared by thermolysis. Solutions of the trimethylsilyl carbamates in dichloromethane may be cast into films, which are converted to their redox-active, deprotected forms by immersion in alcohols or in aqueous solutions. All samples used in electrochemical studies were prepared in this manner.

Scheme 10[a]

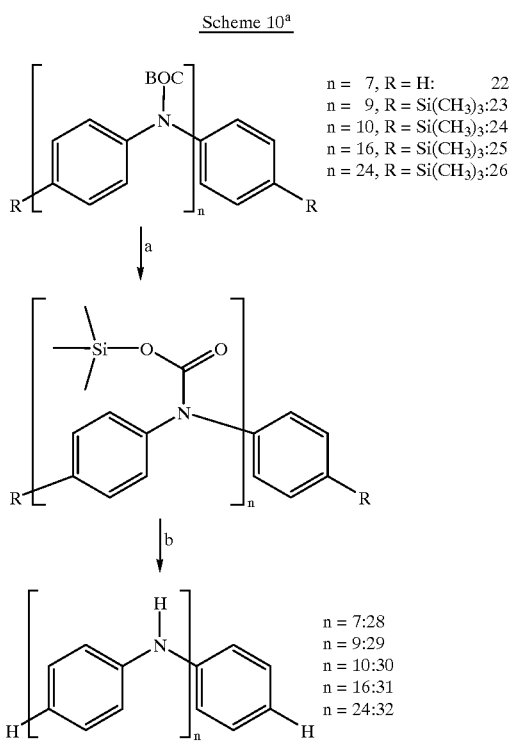

[a]Key: (a) (CH$_3$)$_3$SiI (1.2n eq), CH$_2$Cl$_2$, rt; (b) CH$_3$OH (excess), Et$_3$N, CH$_2$Cl$_2$, rt.

Oxidation States of Aniline Oligomers.

The lowest oxidation state of polyaniline is the insulating leucoemeraldine form, in which all nitrogen atoms are neutral and sp$^3$-hybridized, and all aromatic rings are in the benzenoid form. Oxidation of half of the phenylenediamine moieties to their quinoid forms results in the insulating emeraldine form, which becomes conductive when the imine nitrogen atoms are protonated. This form has been described as a repeating semiquinoid cation to explain its paramagnetism and electrical conductivity. Oxidation of all phenylenediamine moieties to their quinoid forms gives rise to the pernigraniline form, with significant (though not necessarily complete) deprotonation under most conditions. Even when generated by oxidation under extremely nonbasic conditions, and thus probably in its fully protonated form, pernigraniline is an insulator.[31] These oxidation states are illustrated in FIG. 3.

Figure 3:
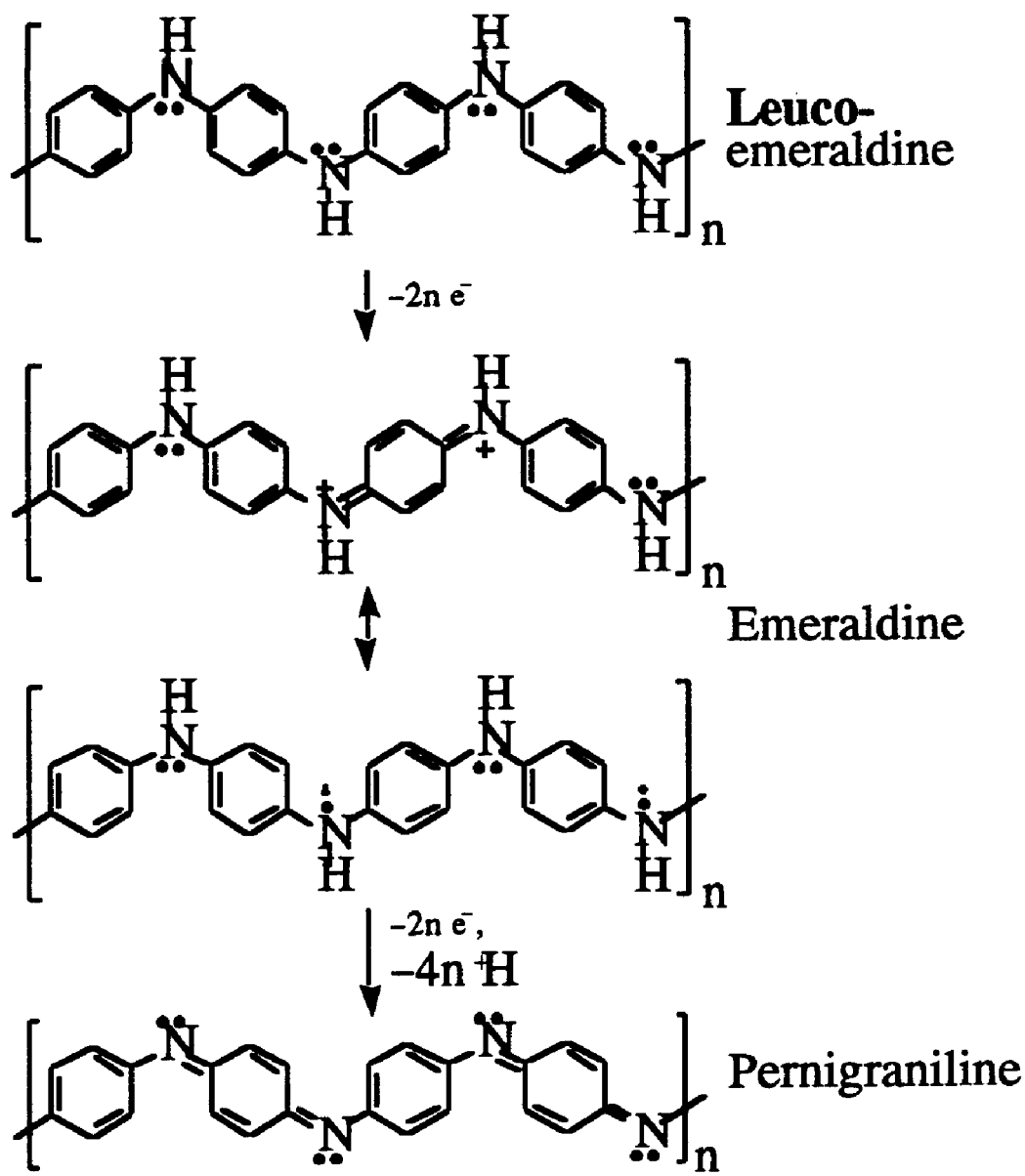
FIG. 3. Principal oxidation states of polyaniline.

Electrochemical studies of polyaniline show two oxidation waves of equal intensity, consistent with the transitions shown in FIG. 3. In contrast, the cyclic voltammogram of phenyl-capped octaaniline, published by Wudl,[32] displays a distinct split in the second oxidation wave, suggesting an intermediate "nigraniline" form[33] in the oxidation from the emeraldine to the pernigraniline form.

We wished to investigate effects of susbtitution in octaanilines, and the effects of chain length on oligoaniline redox behavior. We have examined the oligoanilines in varying degrees of oxidation and protonation by UV-vis spectroscopy, and have studied their electrochemical behavior by cyclic voltammetry.

Electronic Absorption Spectroscopy.

Under neutral conditions, the UV-vis spectra of the oligoanilines (27–32) in a given oxidation state are essentially identical; no significant changes result from substitution or from variations in chain length. The leucoemeraldine forms exhibit a single strong absorption at 334–338 nm; lower-energy transitions are observed for the partially and fully oxidized states. Oxidation of a colorless leucoemeraldine solution in dilute DMF by silver (I) oxide results in an intense blue-purple solution of the emeraldine base, with a sharp peak at 320 nm and a broad band at 620 nm. Silver (II) oxide in DMF converts the leucoemeraldine to a red-pink pernigraniline solution, with a sharp peak at 320 nm and a broad band at 520 nm. The strong blue shift of this band, compared to that of emeraldine, reflects the decreased charge-transfer absorption in the pernigraniline state.

Figure 4:
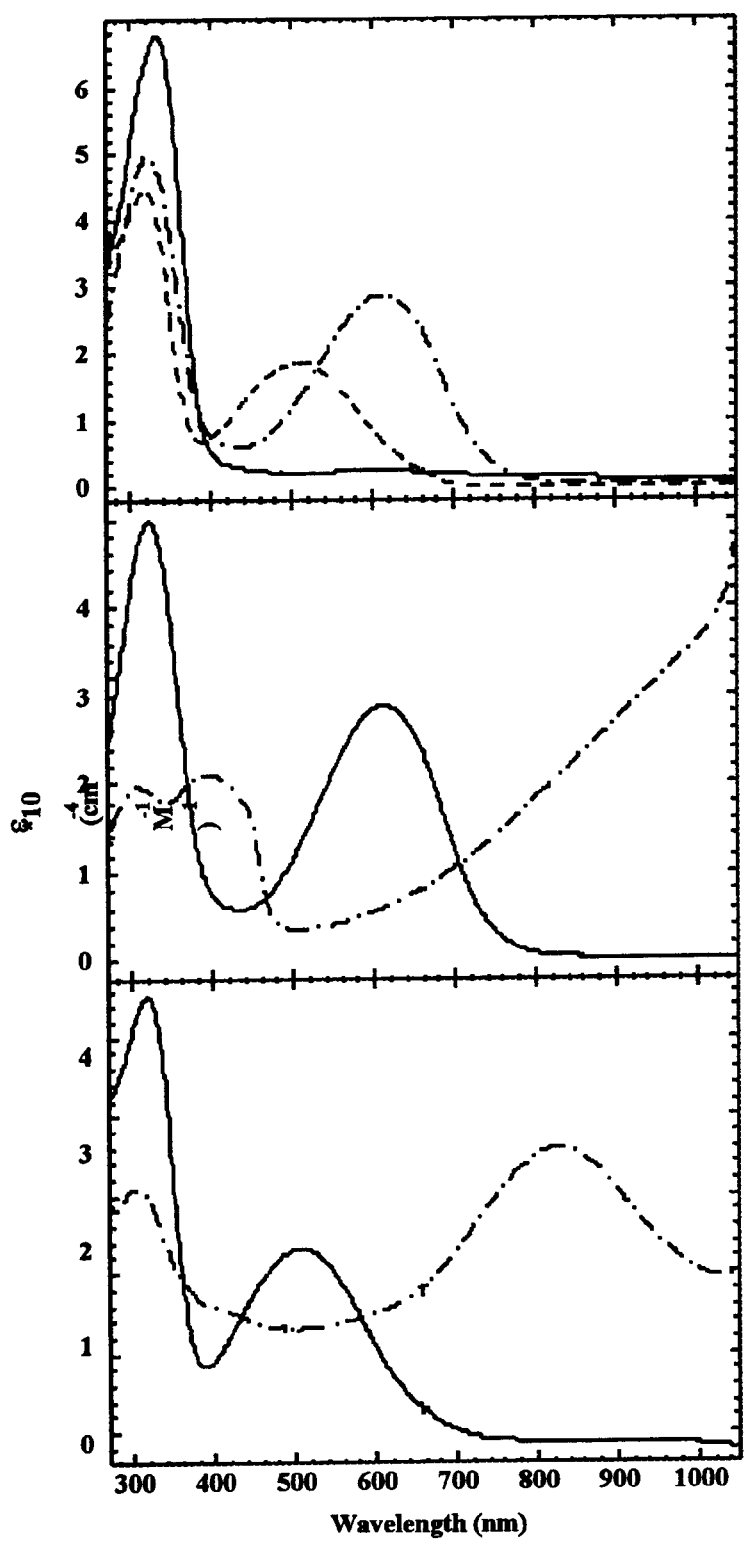
FIG. 4. UV-vis spectra of phenyl-capped octaaniline (27a) in DMF. (top) leucoemeraldine, ___; emeraldine, _·; pernigraniline, _ _ _. Emeraldine (middle) and pernigraniline (bottom): in neutral solution, ____; acidified, _·.

The addition of a drop of sulfuric acid (a large excess) to the UV-vis samples of the emeraldine and pernigraniline forms produces a green color. Protonation of the emeraldine causes the higher-energy absorption to broaden and split; the lower-energy absorption begins at ca. 540 nm and increases in intensity up to the spectrometer's limit at 1050 nm. In the case of the pernigraniline, the lower-energy absorption is broadened, and its maximum is red-shifted from 520 nm to 830 nm. The UV-vis spectra of phenyl-capped octaaniline (27a) are shown in FIG. 4.

Figure 5:
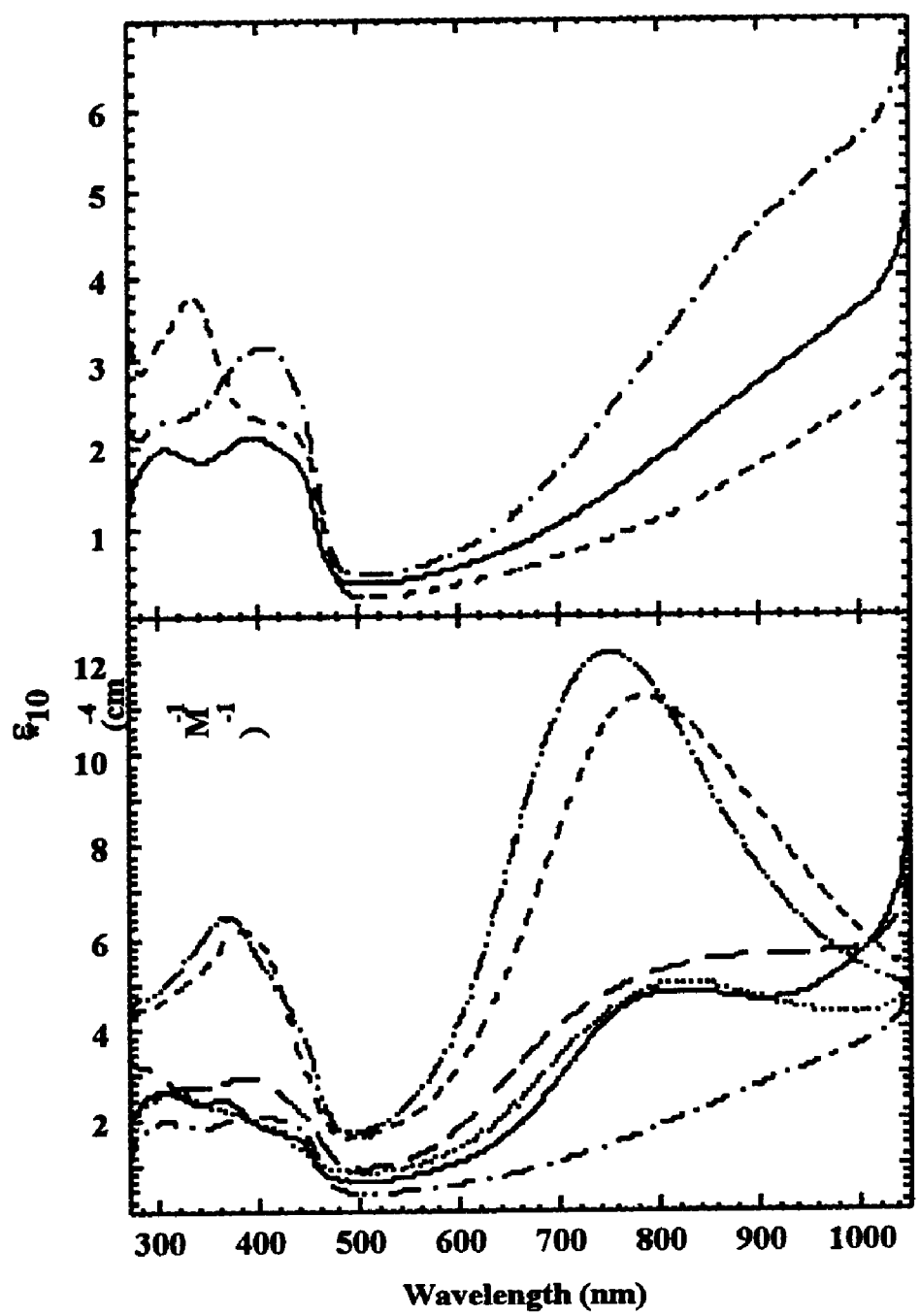
FIG. 5. (top) α,ω-Substituent effects upon the protonated emeraldine form of phenyl-capped octaanilines in DMF: H (27a), ———; CN (27b), - - -; OCH$_3$ (27e), — -. (bottom) Protonated emeraldines of phenyl-capped oligoanilines in DMF: 7-mer (28), ———; 8-mer (27a), — -; 9-mer (29), ·······; 10-mer (30), — — —; 16-mer (31), - - -; 24-mer (32), — - - -.

The spectra of the protonated emeraldine forms vary considerably with changes in electron density or in chain length, as shown in FIG. 5. The absorbance in the near-IR region of 27 becomes more intense with the increase in electron density from the cyano-substituted to the methoxy-substituted octamer. The twin peaks at higher energy, of nearly equal intensity for phenyl-capped octaaniline, show complementary patterns for the cyano- and methoxy-substituted analogues. A comparison of the spectra for different chain lengths shows subtle differences between heptamer, nonamer, and decamer; the distinct curvature in the shape of the near-IR absorption contrasts with the near-linear slope observed for the octamer. In the longer oligomers (16-mer and 24-mer), this absorption shows a much more definite maximum, occurring at somewhat shorter wavelengths.

Electrochemistry. Cyclic voltammetry of the oligoanilines affords valuable insight into the electronic structures of the oxidized forms. We wished to examine, for instance, whether the presence of electron-donating or electron-withdrawing groups at the chain ends would affect the redox behavior of phenyl-capped octaaniline, or whether the electronic effects would be insignificant for the chain as a whole. The salient question with regard to chain length is the behavior of those oligoanilines that do not correspond to the tetraaniline-based model depicted in FIG. 3. Phenyl-capped heptaaniline, nonaaniline, and decaaniline behave quite similarly to the octaaniline upon chemical oxidation, but the nature of the "emeraldine" and "pernigraniline" forms obtained for these chain lengths is not obvious a priori. If the oligoaniline framework were able to stabilize radical cations effectively, either by resonance or by π-stacking between chains,[34] several odd-electron states would be accessible for the heptamer and nonamer, and the decamer emeraldine might be the five-electron oxidation product, containing five equivalent semiquinoid moieties.

The electrochemical studies discussed below employed thin films of the oligoanilines on ITO (indium-tin oxide) coated glass electrodes. The films were prepared by evaporation of a dilute solution of the trimethylsilyl carbamate in dichloromethane, followed by immersion in the electrolyte, dilute aqueous sulfuric acid.[35] The first cycle of each film indicated significant loss of material (approximately 20–30%) during the reduction,[36] but the films exhibited good stability after this break-in scan.

In dilute hydrochloric acid, the major peaks diminish in intensity with each scan, while a broad peak grows in at ca.

0.55 V in the oxidation wave and 0.40 V in the reduction wave. This degradation had been observed previously for both phenyl-capped octaaniline and bulk polyaniline.[32] In dilute sulfuric acid, however, this degradation occurs more slowly.

Integration of the oxidation peaks of phenyl-capped octaaniline (5.0 nanomoles) in the first scan corresponded reproducibly, within two percent, to the removal of eight electrons per molecule, but the oxidations occurred at markedly higher potentials than in subsequent scans. The reduction peaks in the first scan represent a significantly smaller area than the oxidation peaks, but subsequent scans showed good reversibility. In the discussion of oxidation states below, the total number of electrons removed from each molecule is determined by integration of the oxidation peaks in the first scan; the oxidation states of each compound are determined by comparison of the relative peak areas in the second (i.e., first stable) scan.

Phenyl-capped octaaniline (27a) oxidizes from the leucoemeraldine to the emeraldine form in one four-electron step. In contrast, the oxidation from emeraldine to pernigraniline shows a split, with peaks at 0.79 V and at 0.90 V. This split is highly sensitive to changes in electron density at the chain termini. The methoxy groups of 27e cause a larger split in the emeraldine-pernigraniline oxidation wave, with peaks at 0.66 V and at 0.87 V, whereas the cyano groups of 27b cause the split to disappear entirely, with a smooth four-electron oxidation centered at 0.84 V. This disparity is consistent with formation of the nigraniline form, with three quinoid moieties, by a two-electron oxidation of emeraldine. The greater partial positive charge adjacent to the chain ends, compared to the emeraldine state, would be stabilized by resonance with the methoxy group, as shown in Scheme 11, and destabilized by conjugation with the cyano group.

ibly within three percent. Comparison of the areas of the two oxidation peaks showed the first to be approximately twice as large as the second,[37] suggesting that the heptaaniline undergoes a four-electron oxidation followed by a two-electron oxidation.

Similarly, oxidation of phenyl-capped nonaaniline within the same potential range results in the removal of only eight electrons per molecule. The cyclic voltammogram displays two oxidation waves, corresponding in area to two four-electron oxidations. The second of these displays a prominent shoulder at the left side. We believe that the extra nitrogen lone pair, relative to phenyl-capped octaaniline, allows oxidation to a mixture of several nonequivalent but energetically similar nigraniline-like states, beginning at relatively low potentials, en route to the formation of the eight-electron oxidation product.

Oxidation of phenyl-capped decaaniline from −0.3 V to 1.0 V results in the removal of ten electrons, consistent with the conversion of all five phenylenediamine moieties to their quinoid forms. The cyclic voltammogram displays two oxidation waves, the first of which encompasses approximately 50% more area than the second.[37] The oxidation of phenyl-capped decaaniline thus appears to proceed via a six-electron oxidation, followed by a four-electron oxidation.

Figure 7:
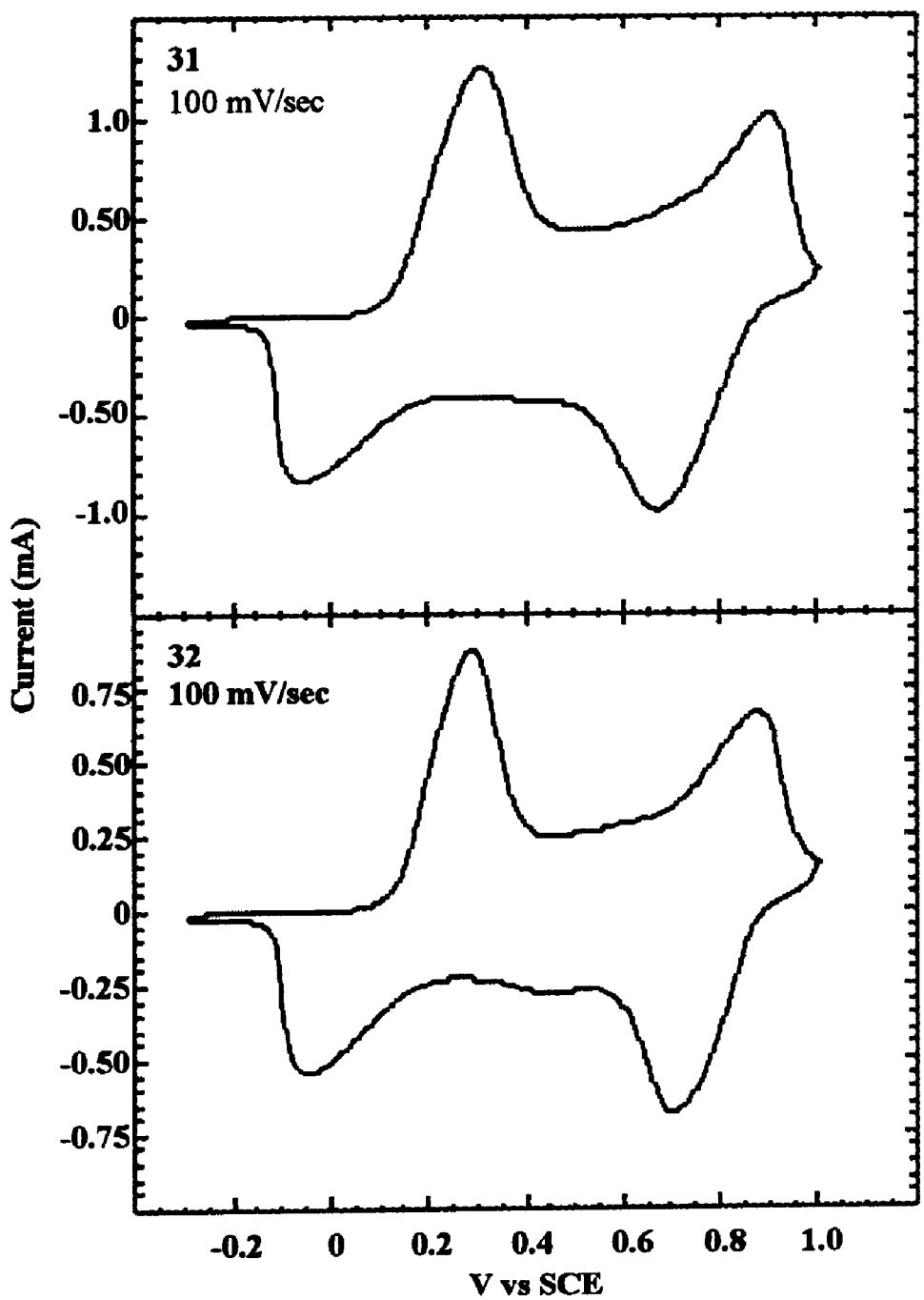
FIG. 7. Cyclic voltammetry of phenyl-capped 16-mer (31) and phenyl-capped 24-mer (32), same conditions as above.

The simplest electrochemical behavior is that of the 16-mer (31) and the 24-mer (32). Cyclic voltammograms of these oligomers are shown in FIG. 7; due to the high molecular weight of 32, a smaller molar quantity (2.5 nmol) was used to obtain a thin film. In contrast to phenyl-capped octaaniline, these longer tetraaniline multiples display no distinct intermediate in the oxidation of their emeraldine forms. The oxidation from the leucoemeraldine to the pernigraniline state, like that of the bulk polymer, results in two peaks of equal area.

Scheme 11
Stabilization of the nigraniline oxidation state by π-donating substituents.

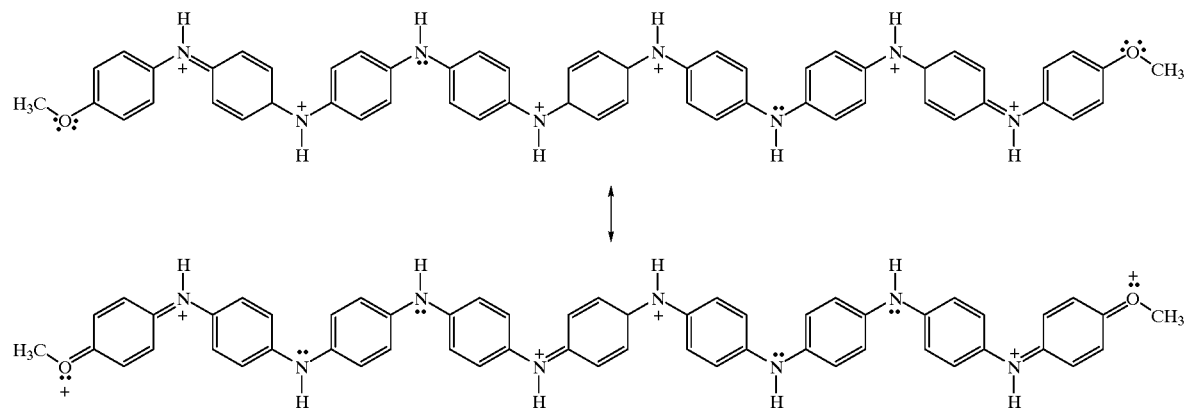

Figure 6:
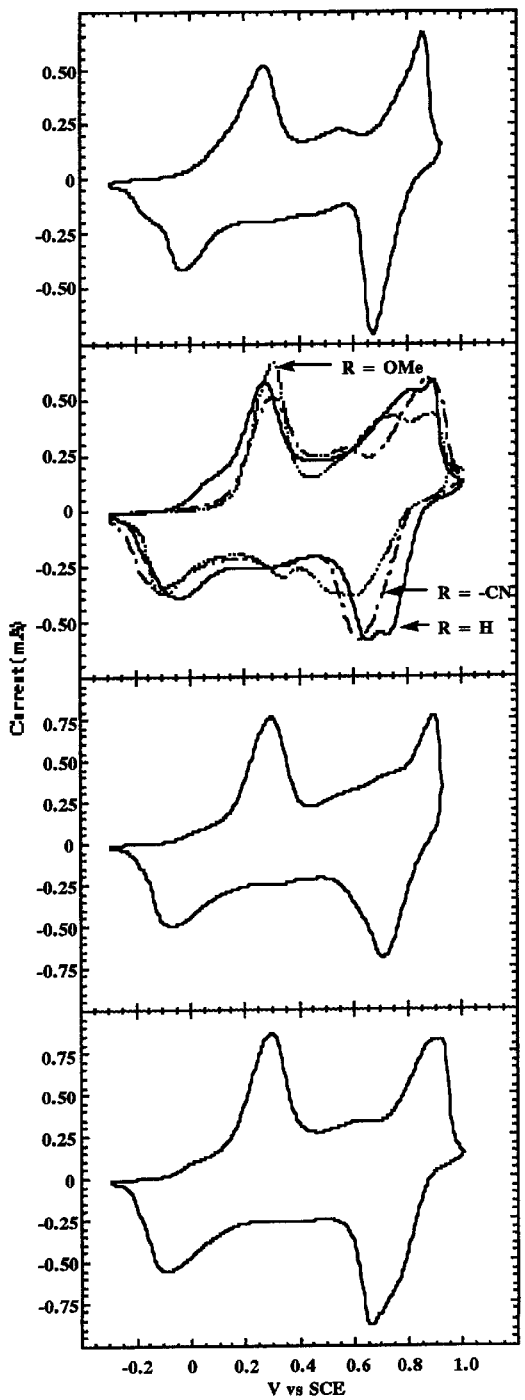
FIG. 6. Cyclic voltammetry of phenyl-capped heptaaniline (28), octaanilines 27 (H, 27a, ———; CN, 27b, — -; OCH$_3$, 27e, ·······), nonaaniline 29, and decaaniline 30 on ITO-coated electrodes in 1.0 M aq. H$_2$SO$_4$ (SCE reference) at a scan rate of 100 mV/sec.
Figure 6:
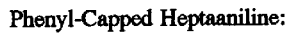
Figure 6:
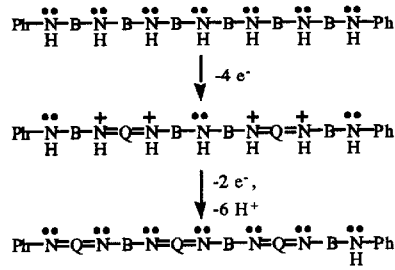
Figure 6:
Figure 6:
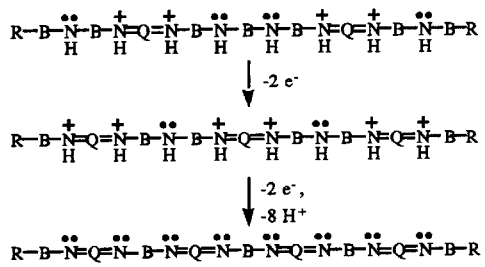
Figure 6:
Figure 6:
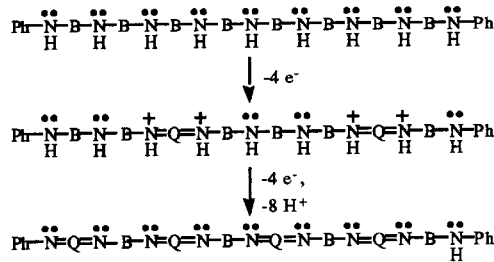
Figure 6:
Figure 6:
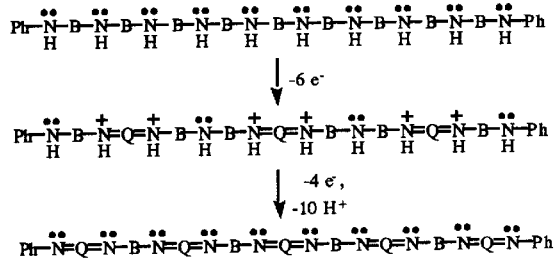
Figure 6:
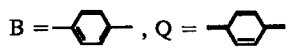

FIG. 6 shows the cyclic voltammograms obtained for 27–30, with proposed oxidation mechanisms for some of the oxidation steps. The intermediates are depicted in their expected major resonance forms. For many of the intermediates the degree of protonation may vary, and several tautomers may exist in addition to those shown.

Figure 8:
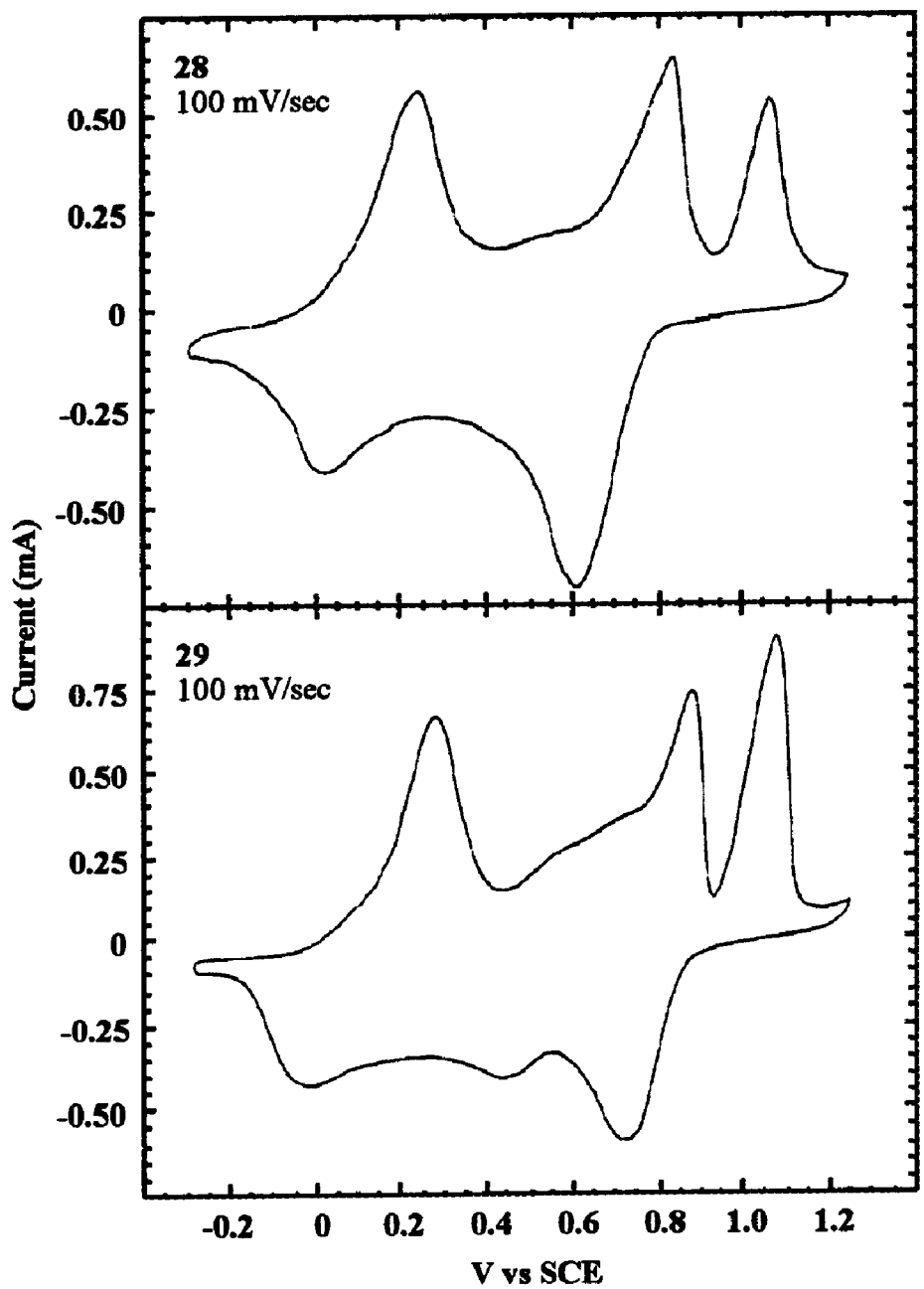
FIG. 8. Irreversible oxidation of phenyl-capped heptaaniline (28) and nonaaniline (29) at high potential, same conditions as above.

In the cyclic voltammogram of phenyl-capped heptaaniline, two reversible oxidations occur as the potential is increased from −0.3 V to 0.95 V. Integration of the first scan for a known film quantity showed that only six electrons were removed per molecule of heptaaniline, reproduc- The even-numbered oligomers investigated here are stable at potentials up to and beyond +1.0 V vs. SCE, and polyaniline in nonnucleophilic solvents has been found to be stable at very high potentials.[31] In marked contrast, the odd-numbered oligomers are unstable at potentials above 0.95 V (FIG. 8). At higher potentials a third oxidation peak is observed, at 1.07 V for the heptaaniline and 1.08 V for the nonaaniline, with no corresponding reduction peak. This two-electron oxidation occurs only once for each film: a second scan to 1.25 V fails to reproduce this peak, and the voltammogram resembles that of an even-numbered oligomer.

The irreversibility of the oxidation, and the fact that no corresponding peak is observed for even-numbered oligomers, is consistent with the formation of a highly unstable odd-electron species, followed by decomposition to a species which undergoes facile one-electron oxidation. The oxidation pattern does not rule out the tail-to-tail dimerization of the radical cation, followed by dehydrogenation, but the product of this reaction should be reduced easily to a benzidine derivative during the reduction wave. Intramolecular C—C bond formation by the odd-electron cation, followed by deprotonation and one-electron oxidation to the carbazole, represents one possible explanation for the observed behavior. Since the carbazole moiety is quite difficult to oxidize,[38] the product would contain an even number of oxidizable nitrogen atoms, and the formation of additional carbazole units during a subsequent scan would not be expected. Scheme 12 illustrates the proposed carbazole formation; for simplicity, only one product is shown, although the cyclization could also occur in the middle of the chain.

tron density results in more intense electronic absorption by the emeraldine in the low bandgap region, and stabilizes the electrochemically observed nigraniline state. The electrochemistry of the heptamer, nonamer, and decamer illustrates the importance of electron-pairing in the redox behavior of these compounds. Oxidation of oligoanilines occurs through even-electron transitions when possible; thus, the decamer oxidizes in unequal steps, and the odd-numbered oligomers generate radical cations only transiently and at high potential. Our observations suggest that the ability of polyaniline to stabilize an unpaired electron through resonance or π-stacking is limited.

Experimental Section

General Information. Proton and carbon nuclear magnetic resonance spectra ($^1$H NMR and $^{13}$C NMR) were recorded on Varian XL-300, UN-300 or XL-500 spectrometers and referenced with respect to residual solvent. The letter "a" before a multiplicity notation indicates an apparent multiplicity. Infrared spectroscopy was carried out on a Perkin-Elmer 1600 Series FT-IR spectrometer. UV-Vis spectra were obtained using a Hewlett-Packard 8451A or 8453A spectrophotometer. FAB mass spectra were recorded on a Finnigan MAT System 8200 using a 3-nitrobenzyl alcohol matrix.

Scheme 12
Proposed carbaole formation in odd-numbered oligoanilines at high potential.

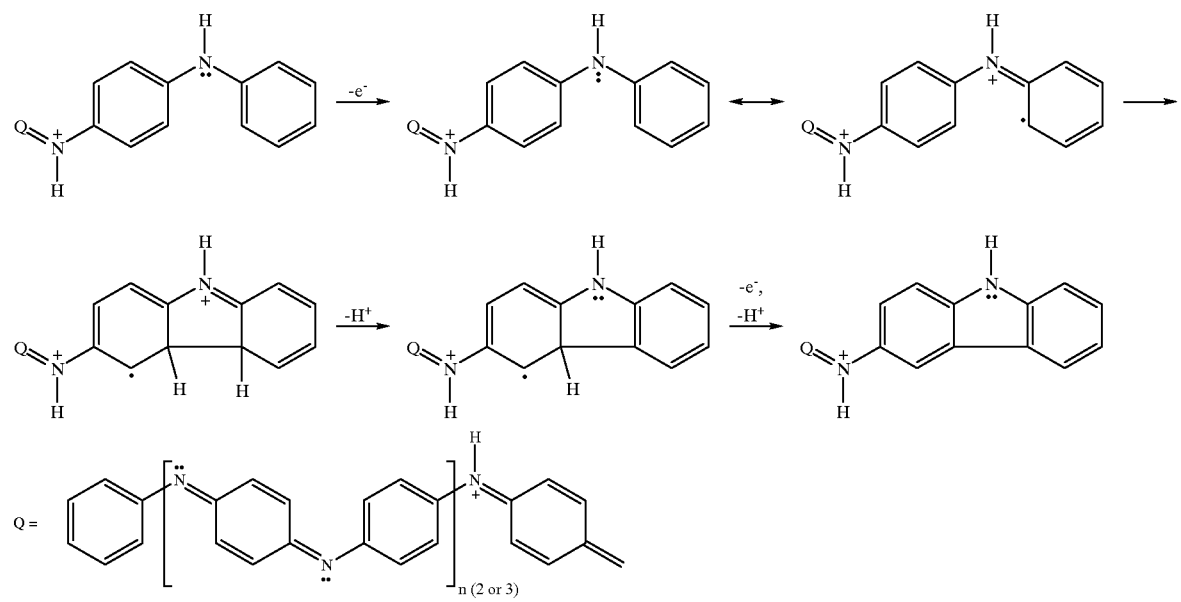

Concluding Remarks

Using palladium catalysis and an orthogonal protective group strategy, we have developed divergent-convergent and convergent methods in the synthesis of well-defined, air-stable oligoaniline precursors, soluble in a variety of common organic solvents. These precursors are easily deprotected to form the leucoemeraldine forms of the corresponding oligoanilines. The synthetic methods are highly versatile, allowing the synthesis of end-functionalized oligoanilines, and the preparation of even or odd chain lengths.

The presence of electron-donating or electron-withdrawing groups at the chain ends results in significant modifications of the UV-vis spectra and electrochemical behavior of phenyl-capped octaaniline. An increase in elec- Elemental analyses were carried out by E & R Microanalytical Laboratory Inc., Corona, N.Y. Gas chromatographic analyses were carried out on a Hewlett-Packard HP-5890 Series II gas chromatograph, fitted with an HP-1 capillary column (25 m, 0.20 mm, 0.11 μm). Thin layer chromatography was carried out on E. Merck SIlica Gel 60 F-254 TLC plates. Melting points were obtained using a Haake Buchler melting point apparatus and are uncorrected.

Reactions under an argon atmosphere were carried out in oven-dried glassware using standard Schienk techniques. Tetrahydrofuran was distilled under argon from sodium benzophenone ketyl. Toluene was distilled under nitrogen from molten sodium. Dichloromethane used in oligomer deprotections was purchased in anhydrous form from Aldrich Chemical Company and stored under nitrogen over activated 3 Å molecular sieves. Absolute ethanol was purchased from Pharmco and used as supplied. Diethyl ether, analytical reagent grade, was purchased from Mallinckrodt and used as supplied. N-Methylpyrrolidinone, anhydrous, and NN-dimethylformamide, reagent grade, were purchased from Aldrich Chemical Company and used as supplied. Deuterated solvents were purchased from Cambridge Isotope Laboratories and used as supplied. All other solvents were of liquid chromatography grade quality, purchased from EM Science and used as supplied.

Molecular sieves were purchased from Aldrich Chemical Company and activated at 180° C. and $10^{-3}$ mm Hg for 12 hours prior to use. Sodium tert-butoxide was purchased from Aldrich Chemical Company and stored in a Vacuum Atmospheres glovebox under nitrogen. Small amounts were removed from the glovebox as needed, stored in a dessicator for up to one week, and weighed in the air. 4-Bromoaniline, benzophenone, chlorotrimethylsilane, p-anisidine, di-tert-butyl dicarbonate solution (1.0 M in tetrahydrofuran), tetra-n-butylammonium tribromide, palladium hydroxide (moist, 20% on carbon), 1,4-phenylenediamine dihydrochloride, aniline, diphenylamine, 4-bromo-tert-butylbenzene, 4-bromobenzonitrile, ammonium formate, hydroxylamine hydrochloride, and hexamethyldisilane were purchased from Aldrich Chemical Company and used as supplied. Di-tert-butyl dicarbonate and 4-dimethylaminopyridine were purchased from Lancaster Synthesis Inc. and used as supplied. 4-Bromo-n-dodecylbenzene was purchased from TCI America and used as supplied. S-BINAP, a gift from Pfizer, was used as supplied. Tris(dibenzylideneacetone) dipalladium, palladium acetate, palladium on carbon, n-butyllithium (1.60 M in hexanes) and bromine were purchased from Strem Chemical Company and used without further purification. All other inorganic reagents were analytical reagent grades purchased from Mallinckrodt and used as supplied.

Synthesis. N-(Diphenylmethylene)-4-bromoaniline (1). The method of Taguchi and Westheimer[39] was modified as follows: Benzophenone (455 g, 2.50 moles) and 4-bromoaniline (473 g, 2.75 moles) were dissolved in toluene (1.2 L, distilled) under argon in a L flask, containing molecular sieves (5 Å, 1.25 kg), fitted with a reflux condenser, rubber septum, and pressure outlet. The mixture was heated to gentle reflux and shaken occasionally; an intense yellow color soon developed. Analysis by GC after 18 hours showed that product formation was nearly complete. The mixture was allowed to cool to room temperature, and the yellow solution was decanted from the molecular sieves, which were washed with diethyl ether until the filtrate was colorless. The organic solutions were combined and concentrated to give an orange oil, 900 mL. Methanol (ca. 80 mL) and a seed crystal of authentic product were added. The product was allowed to crystallize at 0° C. and collected by filtration. The mother liquor was further concentrated. A second crop of crystals formed and was isolated by filtration. Recrystallization of the combined product from methanol afforded the title compound as yellow crystals (760 g, 90%): mp 82–83° C.; $^1$H NMR (300 MHz, CDCl$_3$) δ 7.75 (dd, J=6.9, 1.6 Hz), 7.52–7.39 (m, 3H), 7.32–7.23 (m, 5H), 7.11 (dd, J=8.4, 1.9 Hz, 2H), 6.61 (dt, J=8.5, 2.0 Hz, 2H); $^{13}$C NMR (75 MHz, CDCl$_3$) δ 168.7, 150.4, 139.5, 136.1, 131.6, 131.0, 129.5, 128.8, 128.3, 128.2, 122.8, 116.3, 103.6; IR (neat, cm$^{-1}$)3058, 3024, 1615, 1478; Anal. Calc'd for C$_{19}$H$_{14}$BrN: C, 67.87; H, 4.20. Found: C, 68.08; H, 4.28.

4-(Trimethylsilyl)aniline (2).[25] Aryl bromide 1 (16.8 g, 50.0 mmol) was dissolved in tetrahydrofuran (250 mL) in a dry Schlenk flask under argon. The resulting solution was cooled with stirring to −78° C. A solution of n-butyllithium in hexanes (1.60 M, 31.5 mL, 50.4 mmol) was added dropwise via syringe, causing the yellow solution to turn a deep red color. The reaction mixture was stirred for 30 minutes at −78° C. Chlorotrimethylsilane (6.5 mL, 51 mmol) was added dropwise via syringe over 5 min, causing the red solution to turn a light orange color. The reaction mixture was warmed to room temperature and stirred for 45 min. Triethylamine (10 mL) and methanol (20 mL) were added, resulting in a cloudy, pale yellow suspension. The suspensions obtained from two reactions carried out in this manner were combined and concentrated; the solid residue was taken up in diethyl ether (250 mL) and washed with brine (100 mL). The aqueous phase was extracted with two 75-mL portions of diethyl ether. The organic solutions were combined, dried over potassium carbonate, filtered, and concentrated.

The yellow crystalline product was dissolved in methanol (200 mL). Sodium acetate (16.4 g, 200 mmol) and hydroxylamine hydrochloride (10.4 g, 150 mmol) were added with rapid stirring. After 5 min, solid potassium bicarbonate (15 g, 150 mmol) was added, and the mixture was stirred for 30 min. Diethyl ether (100 mL) was added, and the mixture was filtered to remove precipitated salts. The collected solid was dissolved in water (200 mL), and the resulting solution was extracted with two 50-mL portions of diethyl ether. The combined organic solutions were dried over potassium carbonate, filtered, and concentrated. The residue was taken up in dichloromethane (20 mL), cooled to −78° C., and filtered to remove the precipitated benzophenone oxime. The collected solid was suspended in dichloromethane to dissolve adsorbed 2, and the mixture was cooled to −78° C. and filtered. The filtrates were combined and concentrated, and the precipitation of benzophenone oxime was repeated as described above. The crude aniline was distilled from calcium hydride under high vacuum, affording the title compound as a colorless oil (14.1 g, 85%): bp 44° C./0.01 mm Hg (lit.[25] 102° C./6 mm Hg); $^1$H NMR (300 MHz, CDCl$_3$) δ 7.39 (d, J=8.1 Hz, 2H), 6.75 (d, J=8.1 Hz 2H), 3.75 (s, 2H), 0.29 (s, 9H).

Dimer 3. Aryl bromide 1 (25.15 g, 74.8 mmol), arylamine 2 (13.0 g, 78.6 mmol), sodium tert-butoxide (10.06 g, 105 mmol), Pd$_2$(dba)$_3$ (0.171 g, 0.187 mmol, 0.25 mol %), and S-BINAP (0.349 g, 0.560 mmol, 0.75 mol %) were dissolved in tetrahydrofaran (75 mL) in a Schlenk flask under argon. The reaction mixture was heated to a gentle reflux. Analysis by TLC after 17 h showed complete consumption of aryl bromide 1. The reaction mixture was cooled to room temperature and concentrated. The residue was taken up in dichloromethane (200 mL), washed with brine, dried over potassium carbonate, and concentrated. The crude product, 4-dimethylaminopyridine (1.635 g, 13.4 mmol, 20 mol %), and di-tert-butyl dicarbonate (21.90 g, 100 mmol) were dissolved in tetrahydrofuran (67 mL) in a Schlenk flask under argon. The resulting solution was heated to 60° C. with stirring. After 2 h the solution was cooled to room temperature and concentrated. Crystallization of the product from methanol afforded dimer 3 as pale yellow crystals (32.89 g, 84%): mp 123–124° C.: $^1$H NMR (300 MHz, CDCl$_3$) δ 7.75 (d, J=7.0 Hz, 2H), 7.49–7.40 (m, 5H), 7.28 (d, J=6.2 Hz, 3H), 7.19 (d, J=8.2 Hz, 4H), 6.98 (d, J=8.5 Hz, 2H), 6.69 (d, J=8.7 Hz, 2H), 1.41 (s, 9H), 0.24 (s, 9H); $^{13}$C NMR (75 MHz, CDCl$_3$) δ 168.8, 154.0, 149.5, 143.9, 139.8, 138.4, 137.0, 136.4, 133.8, 131.0, 129.7, 129.5, 128.8, 128.4, 128.1, 127.9, 125.3, 121.6, 81.1, 28.4, −0.9; IR (neat, cm$^{-1}$) 3059, 3022, 2954, 1711, 1500, 1327, 1162, 852; Anal. Calcd for C$_{33}$H$_{36}$N$_2$O$_2$Si: C, 76.11; H, 6.97. Found: C, 76.06;H, 7.18.

Dimer amine 4. A Schlenk flask was charged with dimer 3 (3.64g, 7.00 mmol), ammonium formate (5.297 g, 84.0 mmol), and palladium on carbon (10%, 0.740 g, 0.70 mmol Pd) and purged with argon. Methanol (100 mL) was added, and the resulting mixture was heated with stirring to 60° C. Analysis by TLC after 45 min showed complete consumption of imine 3. The reaction mixture was cooled to room temperature and concentrated. The residue was taken up in dichloromethane, and the resulting solution was filtered through Celite and concentrated. The white solid residue was triturated with hexanes (20 mL), cooled to 0° C., and filtered to afford arylamine 4 as a white solid (2.251 g, 90%): mp 108–109° C.; $^1$H NMR (300 MH, CDCl$_3$) δ 7.42 (d, J=8.5 Hz, 2H), 7.20 (d, J=8.5 Hz, 2H), 7.00 (d, J=8.5 Hz, 2H), 6.64 (d, J=8.5 Hz, 2H), 3.66 (s, 2H), 1.45 (s, 9H), 0.24 (s, 9H); $^{13}$C NMR (75 MHz, CDCl$_3$) δ 154.3, 144.7, 144.1, 136.7, 134.1, 133.7, 128.8, 125.2, 115.4, 80.9, 28.4, –0.9; IR (neat, cm$^{-1}$) 3465, 3367, 3227, 2955, 1696, 1515, 1162, 852; Anal. Calc'd for C$_{20}$H$_{28}$N$_2$O$_2$Si: C, 67.38; H, 7.92. Found: C, 67.54; H, 7.99.

Dimer bromide 5. Procedure A: A Schlenk flask was charged with dimer 3 (7.291 g, 14.0 mmol) and sodium acetate (1.148 g, 14.0 mmol) and purged with argon. Tetrahydrofuran (100 mL) was added, and the resulting mixture was cooled to –78° C. with stirring. Bromine (1.50 mL, 29.1 mmol) was added dropwise, causing the mixture to turn a deep green color. The mixture was stirred for 10 min at –78° C., then warmed to 0° C., causing the solution to turn a brown color. Analysis by TLC after 20 min indicated complete consumption of arylsilane 3. A solution of sodium bicarbonate (0.5 M) and sodium sulfite (0.5 M) in water was added to the reaction mixture with vigorous stirring, dispelling the brown color. The mixture was transferred to a separatory funnel containing diethyl ether (50 mL). The phases were separated, and the aqueous phase extracted with two 50-mL portions of diethyl ether. The ether portions were combined, dried over potassium carbonate, filtered, and concentrated, giving a yellow oil which crystallized on standing. Recrystallization of the product from a 4:1 mixture of hexanes and ethyl acetate afforded aryl bromide 5 as pale yellow crystals (6.545 g, 89%): mp 161–162° C.; $^1$H NMR (300 MHz, CDCl$_3$) δ 7.76 (d, J=8.7 Hz, 2H), 7.49–7.36 (m, 5H), 7.28 (d, J=8.8 Hz, 3H), 7.13 (dd, J=7.8, 2.0 Hz, 2H), 7.05 (d, J=8.7 Hz, 2H), 6.96 (d, J=8.6 Hz, 2H), 6.70 (d, J=8.6 Hz, 2H), 1.41 (s, 9H); $^{13}$C NMR (75 MHz, CDCl$_3$) δ 168.9, 153.6, 149.6, 142.4, 139.5, 137.8, 136.2, 131.6, 131.0, 129.6, 129.5, 128.8, 128.4, 128.0, 127.7, 127.5, 121.6, 118.3, 81.3, 28.3; IR (neat, cm$^{-1}$) 3058, 2977, 1711, 1489, 1325, 1161, 697; Anal. Calcd for C$_{30}$H$_{27}$BrN$_2$O$_2$: C, 68.31; H, 5.16. Found: C, 68.53; H, 5.35.

Procedure B: Aryl bromide 1 (14.1 g, 41.8 mmol), aniline (4.00 mL, 43.9 mmol), sodium tert-butoxide (5.63 g, 58.5 mmol), Pd$_2$(dba)$_3$ (95.7 mg, 0.105 mmol, 0.25 mol %), and S-BINAP (0.195 g, 0.314 mmol, 0.75 mol %) were dissolved in tetrahydrofuran (80 mL) in a Schienk flask under argon. The reaction mixture was heated to a gentle reflux. Analysis by TLC after 24 hours showed complete consumption of the starting bromide. The mixture was cooled to room temperature, taken up in ethyl acetate (80 mL), and washed with a 2.0 M aqueous sodium hydroxide solution (80 mL), followed by brine (80 mL). The organic phase was dried over sodium sulfate, filtered, and concentrated. The residue was taken up in dichloromethane (88 mL), and tetra-n-butylammonium tribromide (23.3 g, 48.3 mmol) was added in one portion with stirring. After 30 min, a saturated aqueous solution of sodium sulfite (80 mL) was added. The mixture was stirred for 10 min, then 2.0 M aqueous sodium hydroxide solution (40 mL) was added. The layers were separated and the organic phase was washed with brine (80 mL), dried over sodium sulfate, filtered, and concentrated. The residual solid, 4-dimethylaminopyridine (0.536 g, 4.39 mmol, 11 mol %) and di-tert-butyl dicarbonate (1.054 g, 4.82 mmol) were dissolved in tetrahydrofuran (50 mL). The resulting solution was heated to reflux. After 3 h at reflux the solution was cooled to room temperature and concentrated. Crystallization of the residue from methanol afforded aryl bromide 5 as pale yellow crystals (18.7 g, 81%). Spectroscopic data were identical to those reported above; mp 159–160° C. Anal. Calcd for C$_{30}$H$_{27}$BrN$_2$O$_2$: C, 68.31; H, 5.16. Found: C, 68.52; H, 5.33.

Tetramer 6. Dimer amine 4 (2.353 g, 6.60 mmol), dimer bromide 5 (3.165 g, 6.00 mmol), sodium tert-butoxide (0.807 g, 8.40 mmol), Pd$_2$(dba)$_3$ (54.9 mg, 0.060 mmol, 1 mol %), and S-BINAP (89.7 mg, 0.144 mmol, 2.4 mol %) were dissolved in toluene (24 mL) in a Schlenk flask under argon. The reaction mixture was heated with stirring to 80° C. Analysis by TLC after 19 h indicated complete consumption of the starting bromide. The mixture was cooled to room temperature and taken up in dichloromethane (100 mL), washed with water (50 mL), dried over potassium carbonate, filtered, and concentrated. The residual solid and 4-dimethylaminopyridine (0.1466 g, 1.20 mmol, 20 mol %) were dissolved in tetrahydrofuran (12 mL) in a Schienk tube under argon. A solution of di-tert-butyl dicarbonate in tetrahydrofuran (1.0 M, 8.0 mL, 8.0 mmol) was added, and the resulting solution was heated with stirring to 60° C. After 2 h the solution was cooled to room temperature and concentrated. Crystallization of the residual solid from methanol afforded tetramer 6 as pale yellow crystals (4.63 g, 85%): mp 131–133° C.; $^1$H NMR (300 MHz, CDCl$_3$) δ 7.76 (d, J=7.2 Hz, 2H), 7.50–7.42 (m, 5H), 7.28 (m, 3H), 7.19 (d, J=8.1 Hz, 2H), 7.13 (d, J=11.7 Hz, 10H), 6.98 (d, J=8.6 Hz, 2H), 6.69 (d, J=8.5 Hz, 2H), 1.469 (s, 9H), 1.453 (s, 9H), 1.408 (s, 9H), 0.26 (s, 9H); $^{13}$C NMR (75 MHz, CDCl$_3$) δ 169.0, 154.1, 154.0, 149.5, 143.5, 140.8, 140.6, 140.5, 139.8, 138.3, 137.8, 136.4, 134.0, 131.1, 129.8, 129.6, 129.0, 128.5, 128.2, 127.8, 127.5, 127.3, 127.2, 126.4, 126.2, 121.7, 81.6, 81.3, 28.4, –0.9; IR (neat, cm$^{-1}$) 3008, 2977, 1711, 1509, 1327, 1161, 851, 756; Anal. calcd for C$_{55}$H$_{62}$N$_4$O$_6$Si: C, 73.14; H, 6.92. Found: C, 72.79; H, 6.86.

Tetramer amine 7. A Schlenk flask was charged with tetramer 6 (4.155 g, 4.6 mmol), ammonium formate (4.061 g, 64.4 mmol), and palladium on carbon (5%, 0.979 g, 0.460 mmol Pd) and purged with argon. Methanol (25 mL) and tetrahydrofuran (15 mL) were added, and the resulting mixture was heated to 50° C. with stirring. Analysis by TLC after 11 h indicated complete consumption of the starting imine. The mixture was cooled to room temperature and concentrated. The residue was taken up in dichloromethane (75 mL), and the resulting mixture was filtered through Celite and concentrated. The white solid residue was triturated with hexanes (30 mL), cooled to 0° C., and collected by filtration to afford amine 7 as a white solid (3.243 g, 95%): mp 190–192° C.; $^1$H NMR (300 MHz, CDCl$_3$) δ 7.45 (d, J=5.0 Hz, 2H), 7.18–7.09 (m, 10H), 6.97 (d, J=5.0 Hz), 6.62 (d, J=5.0 Hz, 2H), 3.67 (s, 2H), 1.46 (s, 9H), 1.44 (s, 18H), 0.25 (s, 9H); $^{13}$C NMR (75 MHz, CDCl$_3$) δ 154.3, 153.91, 153.88, 144.8, 143.4, 141.2, 140.4, 140.4, 139.6, 137.7, 133.9, 133.9, 129.01, 128.6, 127.4, 127.2, 127.1, 126.4, 126.2, 126.0, 115.4, 81.4, 81.4, 81.0, 28.4, 28.4, 28.4, –0.9; IR (neat, cm$^{-1}$) 3472, 3366, 2978, 1708, 1508, 1331, 1161, 1055,844; Anal. Calcd for C$_{42}$H$_{54}$N$_4$O$_6$Si: C, 68.26; H, 7.36. Found: C, 68.38; H 7.52.

Tetramer bromide 8. A Schlenk flask was charged with tetramer 6 (2.50 g, 2.77 mmol) and sodium acetate (227 mg, 2.77 mmol) and purged with argon. Tetrahydrofuran (28 mL) was added, and the resulting mixture was cooled with stirring to 0° C. Bromine (299 μL, 5.81 mmol) was added dropwise. The mixture was stirred for 20 min at 0° C., then triethylamine (1.54 mL, 11.1 mmol) and a 1.0 M aqueous solution of sodium sulfite (20 mL) were added with vigorous stirring. The mixture was stirred for 5 minutes, then partitioned between ethyl acetate (60 mL) and a 2.0 M sodium hydroxide solution (50 mL). The organic layer was washed with saturated aqueous sodium chloride solution (50 mL, dried over anhydrous sodium sulfate, filtered, and concentrated. Crystallization of the solid residue from methanol afforded aryl bromide 8 as pale yellow crystals (2.13 g, 85%): mp 174–176° C.; $^1$H NMR (300 Mz, CDCl$_3$) δ 7.75 (dd, J=8.5, 1.6 Hz, 2H), 7.50–7.35 (m, 6H), 7.27 (d, J=8.5 Hz, 2H), 7.12 (dd, J=7.7, 1.5 Hz, 2H), 7.02 (dd, J=9.0, 2.1 Hz, 2H), 6.94 (d, J=8.5 Hz, 2H), 6.69 (d, J=8.5 Hz, 2H), 1.39 (s, 9H); $^{13}$C NMR (75 MHz, CDCl$_3$) δ 168.8, 153.5, 149.4, 142.3, 139.4, 137.8, 136.1, 131.5, 130.9, 129.5, 129.3, 128.7, 128.2, 127.9, 127.5, 127.4, 121.5, 118.1, 81.2, 28.2; IR (neat, cm$^{-1}$) 1710; Anal. Calcd for C$_{52}$H$_{53}$BrN$_4$O$_6$: C, 68.64; H, 5.87. Found: C, 68.38; H, 5.85.

Octamer 9. Arylamine 7 (1.55 g, 2.10 mmol), aryl bromide 8 (1.82 g, 2.00 mmol), sodium tert-butoxide (0.269 g, 2.80 mmol), Pd$_2$(dba)$_3$ (37 mg, 0.026 mmol, 2 mol %), and S-BINAP (60 mg, 0.096 mmol, 4.8 mol %) were dissolved in toluene (15 mL) in a Schlenk tube under argon. The reaction mixture was heated to 65° C. Analysis by TLC after 17 h indicated complete consumption of the starting bromide. The reaction mixture was cooled to room temperature and taken up in dichloromethane (75 mL). The resulting mixture was washed with brine (50 mL), dried over potassium carbonate, filtered, and concentrated. The residue, 4-dimethylaminopyridine (49 mg, 0.40 mmol, 20 mol %), and di-tert-butyl dicarbonate (0.576 g, 2.64 mmol) were dissolved in tetrahydrofuran (20 mL) in a Schlenk tube under argon. The resulting solution was heated to 65° C. After 3 h the solution was cooled to room temperature and concentrated. Crystallization of the residual solid from methanol afforded octamer 9 as pale yellow crystals (2.48 g, 74%): mp 169–171° C.; $^1$H NMR (300 MHz, CDCl$_3$) δ 7.76 (d, J=8.4 Hz, 2H), 7.50–7.39 (m, 8H), 7.28–7.26 (m, 2H), 7.17 (d, J=8.4 Hz, 2H), 7.16–7.13 (m, 24H), 6.97 (d, J=8.4 Hz, 2H), 6.71 (d, J=8.4 Hz, 2H), 1.45 (s, 9H), 1.43 (s, 45H), 1.39 (s, 9H), 0.25 (s, 9H); $^{13}$C NMR (75 MHz, CDCl$_3$) δ 168.6, 153.7, 153.7, 153.6, 149.2, 143.2, 140.5, 140.2, 140.1, 139.5, 138.0, 137.5, 136.1, 133.7, 130.8, 129.5, 129.3, 128.6, 128.2, 127.9, 127.4, 127.2, 127.0, 126.8, 126.1, 125.8, 121.3, 81.3, 81.2, 80.9, 28.2, -1.1; IR (neat, cm$^{-1}$) 1712; Anal. Calcd for C$_{99}$H$_{114}$N$_8$O$_{14}$Si: C, 71.28; H, 6.88. Found: C, 71.07; H, 7.00.

Octamer amine 10. A Schlenk tube was charged with imine 9 (500 mg, 0.300 mmol), ammonium formate (568 mg, 9.00 mmol), and palladium hydroxide on carbon (20%, 0.105 g, 0.150 mmol Pd) and purged with argon. Isopropanol (30 mL) was added, and the resulting mixture was heated to 80° C. with stirring, causing a visible effervescence. After ca. 15 min the effervescence slowed, and an additional portion of ammonium formate (568 mg, 9.00 mmol) was added. Small portions of ammonium formate were added at 15 min intervals until conversion to amine 10 was complete as judged by thin layer chromatography (ca. 1 h). The reaction mixture was cooled to room temperature, taken up in dichloromethane (20 mL) and filtered through Celite. The filtrate was diluted with dichloromethane (60 mL), washed with a 2.0 M aqueous sodium hydroxide solution (50 mL), dried over anhydrous sodium sulfate, filtered, and concentrated. The white solid residue was recrystallized from a 5:1 mixture of isopropanol and water to afford arylamine 10 as white needles (425 mg, 94%): mp 168–170° C.; $^1$H NMR (300 MHz, CDCl$_3$) δ 7.43 (d, J=8.4 Hz, 2H), 7.16 (d, J=8.4 Hz, 2H), 7.14–7.12 (m, 24H), 7.02 (d, J=8.4 Hz, 2H), 6.77 (d, J=8.4 Hz, 2H), 3.65 (bs, 2H), 1.44 (s, 9H), 1.43 (s, 54 H), 0.24 (s, 9H); $^{13}$C NMR (75 MHz, CDCl$_3$) δ 154.1, 153.6, 153.6, 144.6, 143.2, 141.0, 140.3, 140.3, 140.1, 140.1, 140.0, 139.3, 137.5, 133.7, 128.8, 128.4, 127.2, 127.0, 126.8, 126.2, 125.8, 115.1, 81.3, 81.2, 80.8, 28.1, -1.2; IR (neat, cm$^{-1}$) 3468, 3368, 1710; Anal. Calcd for C$_{86}$N$_{106}$N$_8$O$_{14}$: C, 68.68; H, 7.10. Found: C, 68.43; H, 6.86.

N-(Diphenylmethylene)-N',N"-bis(tert-butoxycarbonyl)-teraniline (11). Dimer bromide 5 (3.06 g, 5.80 mmol), aniline (0.56 mL, 6.1 mmol), sodium tert-butoxide (0.8072 g, 8.40 mmol), Pd$_2$(dba)$_3$ (54.9 mg, 0.060 mmol, 1.0 mol %), and S-BINAP (89.7 mg, 2.5 mol %) were dissolved in toluene (20 mL) in a Schlenk flask under argon. The reaction mixture was heated to 80° C. with stirring. Analysis by TLC after 14 h indicated complete consumption of the starting bromide. The mixture was cooled to room temperature and taken up in diethyl ether (75 mL). The resulting mixture was washed with brine (50 mL), dried over potassium carbonate, filtered, and concentrated. The residue, di-tert-butyl dicarbonate (1.53 g, 7.0 mmol), and 4-dimethylaminopyridine (0.131 g, 1.16 mmol, 20 mol %) were dissolved in tetrahydrofuran (15 mL) in a Schlenk flask under argon. The reaction mixture was heated with stirring to 60° C. After 3 h the solution was cooled to room temperature and concentrated. The solid residue was crystallized from ethanol. Recrystallization of the product from ethanol afforded the title compound as pale yellow crystals (3.00 g, 81%): mp 149–151° C.; $^1$H NMR (300 MHz, CDCl$_3$) δ 7.75 (d, J=8.5 Hz, 2H), 7.48–7.38 (m, 3H), 7.33–7.24 (m, 5H), 7.21–7.16 (m, 3H), 7.14–7.07 (m, 6H), 6.97 (d, J=8.8 Hz, 2H), 6.77 (d, J=8.8 Hz, 2H), 1.45 (s, 9H), 1.40 (s, 9H); $^{13}$C NMR (75 MHz, CDCl$_3$) δ 168.9, 154.0, 149.4, 143.0, 140.6, 140.0, 139.7, 138.2, 136.3, 131.0, 129.7, 129.5, 128.9, 128.4, 128.1, 127.7, 127.2, 127.0, 126.3, 125.9, 121.6, 81.4, 81.2, 28.4, 28.4; IR (neat, cm$^{-1}$) 2977, 2930, 1710, 1509, 1324, 1161, 758, 696; Anal. Calcd for C$_{41}$H$_{41}$N$_3$O$_4$: C, 76.97; H, 6.46. Found: C, 77.16; H, 6.70.

N-Phenyl-N'-(4-aminophenyl)-N,N'-bis(tert-butoxyarbonyl)-1,4-phenylenediamine (12). A Schlenk flask was charged with imine 11 (1.245 g, 1.95 mmol), ammonium formate (1.840 g, 29.2 mmol), and palladium on carbon (5%, 0.414 g, 1.95 mmol Pd). Methanol (8 mL) and tetrahydrofuran (4 mL) were added via syringe. The resulting mixture was heated to 60° C. with stirring. Analysis by TLC after 90 min showed incomplete consumption of the starting imine. An additional portion of palladium on carbon (5%, 0.414 g, 1.95 mmol Pd) was added, and the solid ammonium formate which collected above the mixture was periodically redissolved. Analysis by TLC after 2 h showed complete consumption of the starting inline. The mixture was cooled to room temperature and concentrated. The residue was taken up in dichloromethane, and the resulting mixture was filtered through Celite and concentrated. The residual white solid was triturated in hexanes (30 mL), cooled to 0° C., and collected by filtration, affording the title compound as a white solid (0.884 g, 96%): mp 180–182° C. with slow decomposition; $^1$H NMR (300 MHz, CDCl$_3$) δ 7.31 (dd, J=8.2, 3.9 Hz, 2H), 7.21–7.10 (m, 7H), 6.98 (dd, J=5.3, 1.2 Hz, 2H), 6.62 (dd, J=5.3, 1.2 Hz, 2H); $^{13}$C NMR (75 MHz, CDCl$_3$) δ 154.3, 154.0, 144.8, 143.0, 141.0, 139.8, 134.0, 129.1, 128.8, 128.7, 128.6, 127.2, 127.0, 126.4, 126.2, 125.8, 115.4, 81.3, 81.0, 28.4, 28.4; IR(neat, cm$^{-1}$) 3460, 3366, 3037, 2978, 2919, 1702, 1508, 1337, 1161, 1055; Anal. Calcd for $C_{28}H_{33}N_3O_4$: C, 70.71; H, 6.99. Found: C, 70.84; H, 6.78.

N-(Diphenylmethylene)-4-[4-methoxy-N-(tert-butoycarbonyl)anilino]aniline (13). Aryl bromide 1 (2.60 g, 7.74 mmol), p-anisidine (1.00 g, 8.13 mmol), sodium tert-butoxide (1.04 g, 10.8 mmol), $Pd_2(dba)_3$ (35.0 mg, 0.0387 mmol, 1.0 mol %), and S-BINAP (72.0 mg, 0.116 mmol, 1.5 mol %) were dissolved in tetrahydrofuran (25 mL) in a Schlenk flask under argon. The reaction mixture was heated to reflux. After 18 h, the mixture was cooled to room temperature. 4-Dimethylaminopyridine (47.0 mg, 0.774 mmol, 10 mol %) and a solution of di-tert-butyl dicarbonate in tetrahydrofuran (1.0 M, 11.6 mL, 11.6 mmol) were added, and the resulting mixture was heated to reflux. After 3 h the reaction mixture was cooled to room temperature, taken up in a 2:1 mixture of hexanes and ethyl acetate (25 mL), filtered through Celite, and concentrated. Crystallization of the residual solid from methanol afforded the title compound as yellow crystals (3.11 g, 84%): mp 148–149° C.; $^1$H NMR (300 MHz, $CDCl_3$) δ 7.73 (d, J=7.1 Hz, 2H), 7.50–7.36 (m, 4H), 7.25 (d, J=6.0 Hz, 2H), 7.11 (d, J=7.1 Hz, 2H), 7.07 (d, J=9.1 Hz, 2H), 6.97 (d, J=8.8 Hz, 2H), 6.80 (d, J=9.1 Hz, 2H), 6.65 (d, J=8.8 Hz, 2H), 3.77 (s, 3H), 1.39 (s, 9H); $^{13}$C NMR (75 MHz, $CDCl_3$) δ 168.3, 157.0, 153.9, 148.4, 139.4, 138.5, 130.7, 129.4, 129.2, 128.5, 128.1, 127.8, 127.6, 126.8, 121.2, 113.7, 80.6, 55.4, 28.3; IR (neat, cm$^{-1}$) 1705, 1612; Anal. Calcd for $C_{31}H_{30}N_2O_3$: C, 77.80; H, 6.32. Found: C, 77.77; H, 6.38.

N-(4-Methoxyphenyl)-N'-(4-bromophenyl)-N,N'-bis(tert-butoxycarbonyl)-1,4-phenylenediamine (14). A Schlenk flask was charged with imine 13 (1.00 g, 2.09 mmol), mmonium formate (2.64 g, 41.8 mmol), and palladium hydroxide on carbon (20%, 0.291 g, 0.209 mmol Pd). Ethanol (20 mL) was added, and the resulting mixture was heated to 60° C. After 30 min the reaction mixture was cooled to room temperature, taken up in ethyl acetate (40 mL), and filtered through Celite. The filtrate was diluted with ethyl acetate (60 mL), washed with a 2.0 M aqueous solution of sodium hydroxide (100 mL) and with brine (50 mL), dried over anhydrous sodium sulfate, filtered, and concentrated. The residual white solid, 1,4-dibromobenzene (470 mg, 1.99 mmol), sodium tert-butoxide (268 mg, 2.79 mmol), $Pd_2(dba)_3$ (18.2 mg, 0.0199 mmol, 1.0 mol %), and S-BINAP (37.2 mg, 0.0598 mmol, 3.0 mol %) were dissolved in tetrahydrofuiran (10 mL) in a Schlenk tube under argon. The reaction mixture was heated to reflux, After 24 h, the mixture was cooled to room temperature. 4-Dimethylaminopyridine (24.0 mg, 0.199 mmol, 10 mol %) and a solution of di-tert-butyl dicarbonate in tetrahydrofuran (1.0 M, 3.0 mL, 3.0 mmol) were added, and the resulting mixture was heated to reflux. After 3 h, the reaction mixture was cooled to room temperature, taken up in a 2:1 mixture of hexanes and ethyl acetate (10 mL), filtered through Celite, and concentrated. Crystallization of the residual solid from methanol containing a small proportion of dichloromethane afforded the title compound as white crystals (0.847 g, 75%): mp 169–170° C.; $^1$H NMR (300 MHz, $CDCl_3$) δ 7.40 (d, J=8.7 Hz, 2H), 7.17–7.06 (m, 8H), 6.84 (d, J=9.0 Hz, 2H), 3.80 (s, 3H), 1.44 (s, 18H); $^{13}$C NMR (75 MHz, $CDCl_3$) δ 157.7, 153.9, 153.4, 142.0, 141.0, 139.3, 135.6, 131.7, 128.5, 128.3, 127.0, 126.4, 118.9, 114.1, 81.6, 81.1, 55.4, 28.2, 28.2; IR (neat, cm$^{-1}$) 1709; Anal. Calcd for $C_{29}H_{33}BrN_2O_5$: C, 61.16; H,5.84. Found: C, 61.15; H, 5.81.

Tetramer diamine 15. 1,4-Phenylenediamine dihydrochloride (4.53 g, 25.0 mmol), aryl bromide 1 (17.0 g, 50.5 mmol), sodium tert-butoxide (10.8 g, 113 mmol), $Pd(OAc)_2$ (56.1 mg, 0.250 mmol, 1.0 mol %), and S-BINAP (234 mg, 0.375 mmol, 1.5 mol %) were dissolved in toluene (200 mL) in a Schlenk flask under argon. The reaction mixture was heated to 80° C. with stirring. After 24 h, the mixture was cooled to room temperature. 4-Dimethylaminopyridine (305 mg, 2.50 mmol, 10 mol %), a solution of di-tert-butyl dicarbonate in tetrahydrofuran (1.0 M, 87.5 mL, 87.5 mmol), and tetrahydrofuran (50 mL) were added. The resulting mixture was heated to 80° C. with stirring. After 24 h the hot reaction mixture was poured into hot ethanol (400 mL). Heating was discontinued and the mixture was allowed to stand for 6 h. The yellow powder which formed was collected by filtration. The crude product and hydroxylamine hydrochloride (4.34 g, 62.5 mmol) were suspended in pyridine (8.1 mL, 100 mmol), chloroform (400 mL), tetrahydrofuran (100 mL), and ethanol (50 mL). The suspension was stirred for 3 h, then treated with triethylamine (34.8 mL, 250 mmol). After an additional 3 h the reaction mixture was concentrated. The residual solid was heated in isopropanol (600 mL), chloroform (120 mL) and water (60 mL) for 10 min, then allowed to cool to room temperature and to stand for 12 h. The precipitated product was collected by filtration, washed with water followed by isopropanol, and dried in vacuo to afford diamine 15 as a white powder (11.1 g, 91%): mp 208–211° C.; $^1$H NMR (300 MHz, DMSO-$d_6$) δ 7.06 (s, 4H), 6.81 (d, J=8.4 Hz, 4H), 6.49 (d, J=8.4 Hz, 4H), 5.11 (s, 4H), 1.33 (s, 18 H); $^{13}$C NMR (75 MHz, DMSO-$d_6$) δ 153.4, 146.9, 140.2, 131.1, 128.0, 125.9, 113.8, 79.6, 27.8; IR (neat, cm$^{-1}$) 3460, 3364, 1707; Anal. Calcd for $C_{28}H_{34}N_4O_4$: C, 68.55; H, 6.99. Found: C, 68.57; H, 7.05.

Octamer bis-imine 16. Diamine 15 (4.23 g, 8.63 mmol), dimer bromide 5 (9.56 g, 18.1 nmmol), sodium tert-butoxide (2.32 g, 24.2 mmol), $Pd(OAc)_2$ (116 mg, 0.518 mmol, 6.0 mol %), and S-BINAP (376 mg, 0.604 mmol, 7.0 mol %) were dissolved in tetrahydrofuran (43 mL) and triethylamine (11 mL) in a Schlenk flask under argon. The reaction mixture was heated to 90° C. After 48 h, the mixture was cooled to room temperature. 4-Dimethylaminopyridine (105 mg, 0.863 mmol, 10 mol %), tetrahydrofuran (20 mL), and a solution of di-tert-butyl dicarbonate in tetrahydrofuran (1.0 M, 34.5 mL, 34.5 mmol) were added. The resulting mixture was heated to 67° C. After 24 h the mixture was cooled to room temperature. Ethyl acetate (100 mL) and a 2.0 M aqueous solution of sodium hydroxide (60 mL) were added. The mixture was stirred for 15 minutes, then partitioned between ethyl acetate (100 mL) and water (250 mL). The organic layer was washed with brine (200 mL), dried over anhydrous sodium sulfate, filtered, and concentrated. The residual solid was crystallized from a mixture of chloroform and isopropanol. The mother liquor was concentrated, and the residue was taken up in isopropanol. A second crop of crystals formed and was collected by filtration. The crops were combined and dried under vacuum to afford bis-imine 16 as yellow crystals (10.1 g, 74%): mp 154–158° C.; $^1$H NMR (300 MHz, $CDCl_3$) δ 7.74 (d, J=7.0 Hz, 4H), 7.48–7.381 (m, 8H), 7.27–7.23 (m, 8H), 7.11 (s, 16H), 7.08 (s, 4H), 6.95 (d, J=8.4 Hz, 4H), 6.67 (d, J=8.4 Hz, 4H), 1.42 (s, 36 H), 1.38 (s, 18H); $^{13}$C NMR (75 MHz, $CDCl_3$) δ 168.5, 153.6, 153.5, 149.0, 140.5, 140.1, 140.0, 140.0, 139.4, 139.4, 137.9, 136.0, 130.7, 130.7, 129.4, 129.2, 128.6, 128.1, 127.8, 127.4, 126.9, 126.8, 126.0, 121.3, 81.3, 81.3, 81.0, 28.3; IR(neat, cm$^{-1}$) 1711; Anal. Calcd for $C_{98}H_{102}N_8O_{12}$: C, 74.31; H, 6.49. Found: C, 74.36; H, 6.54.

Octamer diamine 17. A Schlenk flask was charged with bis-imine 16 (3.00 g, 1.89 mmol), ammonium formate (2.39 g, 37.9 mmol), and 20% palladium hydroxide on carbon (0.758 mmol). Tetrahydrofuran (50 mL) and ethanol (25 mL) were added, and the resulting mixture was heated to 70° C., causing an effervescence which slowed after ca. 30 min. An additional portion of ammonium formate (2.39 g, 37.9 mmol) was added. Ammonium formate was added in portions every 60 min until conversion to the diamine was complete as judged by TLC analysis. The mixture was cooled to room temperature, taken up in ethyl acetate (40 mL), and filtered through Celite. The filtrate was diluted with a 2:1 mixture of hexanes and ethyl acetate (40 mL). The resulting solution was washed with a 2.0 M aqueous solution of sodium hydroxide (40 mL) and with brine (40 mL), dried over anhydrous sodium sulfate, filtered, and concentrated. Crystallization of the residual solid from a mixture of hexanes and isopropanol afforded diamine 17 as white crystals (2.03 g, 86%): mp 169–172° C.; $^1$H NMR (300 MHz, CDCl$_3$) δ 7.16–7.07 (m, 20H), 6.96 (d, J=8.4 Hz, 4H), 6.60 (d, J=8.4 Hz, 4H), 3.65 (bs, 4H), 1.43 (s, 54 H); $^{13}$C NMR (75 MHz, CDCl$_3$) δ 154.1, 153.6, 153.6, 144.6, 141.0, 140.3, 140.1, 140.0, 139.4, 137.8, 133.7, 128.4, 126.9, 126.9, 126.8, 126.2, 115.1, 81.2, 81.2, 80.7, 28.2, 28.1; IR (neat, cm$^{-1}$) 3460, 3369, 1702; Anal. Calcd for C$_{72}$H$_{86}$N$_8$O$_{12}$: C, 68.88; H, 6.90. Found: C, 68.68; H, 6.84.

General Procedure for the Conversion of Octamer Diamine 17 to Octamers 18a–d. Diamine 17 (1.26 g, 1.00 mmol), aryl bromide (2.30 mmol), sodium tert-butoxide (240 mg, 2.50 mmol), Pd$_2$(dba)$_3$ (18.7 mg, 0.0204 mmol, 2.0 mol %), and S-BINAP (38.1 mg, 0.0613 mmol, 6 mol %) were dissolved in tetrahydrofuran (10 mL) in a Schlenk tube under argon. The reaction mixture was heated to reflux. After 48 h, the mixture was cooled to room temperature. 4-Dimethylaminopyridine (12.0 mg, 0.100 mmol, 10 mol %) and a solution of di-tert-butyl dicarbonate in tetrahydrofuran (1.0 M 3.5 mL, 3.5 mmol) were added, and the resulting mixture was heated to reflux. After 3 h, the mixture was cooled to room temperature, taken up in a 2:1 mixture of hexanes and ethyl acetate (10 mL), and filtered through Celite. The filtrate was concentrated and the residue was crystallized.

Phenyl-capped octamer 18a. Obtained as pale yellow crystals from a 6:1 mixture of methanol and chloroform in 77% yield: mp 171–173° C.; $^1$H NMR (300 MHz, CDCl$_3$) δ 7.30 (t, J=8.7Hz, 2H), 7.20–7.15 (m, 4H), 7.13 (s, 32H), 1.44 (s, 18H), 1.43 (s, 54H); $^{13}$C NMR (75 MHz, CDCl$_3$) δ 153.7, 153.6, 153.6, 142.8, 140.5, 140.2, 140.0, 128.7, 127.0, 125.7, 81.3, 81.3, 81.2, 28.2; IR (neat, cm$^{-1}$) 1711; HRMS (FAB) m/z 1606.8043 (1606.8037 calcd for C$_{94}$H$_{110}$N$_8$O$_{16}$, M$^+$); Anal. Calcd for C$_{94}$H$_{110}$N$_8$O$_{16}$: C, 70.22; H, 6.90. Found: C, 70.25; H, 6.91.

α,ω-Bis(cyano)-phenyl-capped octamer 18b. Obtained as pale yellow crystals from methanol in 79% yield: mp 163–166° C.; $^1$H NMR (300 MHz, CDCl$_3$) δ 7.55 (d, J=9.0 Hz, 4H), 7.31 (d, J=9.0 Hz, 4H), 7.21 (d, J=8.7 Hz, 2H), 7.16–7.13 (m, 24H), 7.08(d, J=8.7 Hz, 2H), 1.44 (s, 36H), 1.43 (s, 36H); $^{13}$C NMR (75 MHz, CDCl$_3$) δ 153.6, 153.5, 151.6, 147.0, 140.2, 140.1, 140.1, 140.1, 136.9, 132.5, 128.2, 128.0, 127.3, 127.0, 126.7, 125.6, 82.6, 82.2, 81.3, 28.2, 27.9; IR (neat, cm$^{-1}$) 1713; HRMS (FAB) m/z 1656.7952 (1656.7945 calcd for C$_{96}$H$_{114}$N$_8$O$_{16}$, M$^+$); Anal. Calcd for C$_{96}$H$_{114}$N$_8$O$_{16}$: C, 69.55; H, 6.57. Found: C, 69.24; H, 6.68.

α,ω-Bis(tert-butyl)-phenyl-capped octamer 18c. Obtained as pale yellow crystals from a 10:1 mixture of ethanol and chloroform in 82% yield: mp 172–176° C.; $^1$H NMR (300 MHz, CDCl$_3$) δ 7.30 (d, J=9.0 Hz, 4H), 7.12 (s, 28H), 7.10 (d, J=9.0 Hz, 4H), 1.44 (s, 18H), 1.43 (s, 54H), 1.29 (s, 18H); $^{13}$C NMR (75 MHz, CDCl$_3$) δ 153.8, 153.6, 153.6, 148.6, 140.6, 140.2, 140.1, 139.9, 127.0, 126.3, 125.6, 81.3, 81.3, 81.0, 24.4, 31.3, 28.2; IR(neat, cm$^{-1}$) 1713; HRMS (FAB) m/z 1718.9275 (1718.9292 calcd for C$_{102}$H$_{126}$N$_8$O$_{16}$, M$^+$); Anal. Calcd for C$_{102}$H$_{126}$N$_8$O$_{16}$: C, 71.22; H, 7.38. Found: C, 71.02; H, 7.27.

α,ω-Bis(n-dodecyl)-phenyl-capped octamer 18d. Obtained as pale yellow crystals from a 10:1 mixture of ethanol and chloroform in 82% yield: mp 172–175° C.; $^1$H NMR (300 MHz, CDCl$_3$) δ 7.16–7.08 (m, 36H), 2.57 (t, J=8.0 Hz, 4H), 1.65–1.53 (m, 4H), 1.43 (s, 2H), 1.32–1.20 (m, 36H), 0.88 (t, J=7.3 Hz, 6H); $^{13}$C NMR (75 MHz, CDCl$_3$) δ 153.7, 153.6, 140.6, 140.3, 140.2, 139.8, 128.7, 127.0, 126.9, 126.8, 81.3, 81.3, 81.0, 35.4, 1.9, 31.3, 29.6, 29.6, 29.6, 29.5, 29.3, 29.3, 28.2, 27.9, 22.6, 14.1; IR (neat, cm$^{-1}$) 1712; Anal. Calcd for C$_{118}$H$_{158}$N$_8$O$_{16}$: C, 72.88; H, 8.19. Found: C, 72.71; H, 8.24.

α,ω-Bis(methoxy)-phenyl-capped octamer 18e. Aryl bromide 14 (300 mg, 0.527 mmol), diamine 15 (123 mg, 0.251 mmol), sodium tert-butoxide (60 mg, 0.627 mmol), Pd$_2$(dba)$_3$ (4.6 mg, 0.00502 mmol), and S-BINAP (9.4 mg, 0.0151 mmol) were dissolved in toluene (3 mL) in a Schlenk tube under argon. The reaction mixture was heated to 80° C. After 48 h, the mixture was cooled to room temperature. 4-Dimethylaminopyridine (3.1 mg, 0.0251 mmol, 10 mol %) and a solution of di-tert-butyl dicarbonate in tetrahydrofuran (1.0 M, 0.88 mL, 0.88 mmol) were added, and the resulting mixture was heated to reflux. After 3 h the reaction mixture was cooled to room temperature, taken up in a 2:1 mixture of hexanes and ethyl acetate (6 mL), filtered through Celite, and concentrated. Crystallization of the residual solid from a mixture of isopropanol and water afforded 18e as white crystals (0.301 g, 72%): mp 173–176° C.; $^1$H NMR (300 MHz, CDCl$_3$) δ 7.12 (s, 28H), 7.11 (d, J=9.0 Hz, 4H), 6.84 (d, J=9.0 Hz, 4H), 3.79 (s, 6H), 1.43 (s, 72H); $^{13}$C NMR (75 MHz, CDCl$_3$) δ 157.6, 153.9, 153.6, 140.8, 140.2, 139.7, 135.8, 128.4, 127.0, 126.9, 114.1, 81.3, 81.2, 81.0, 55.4, 28.2; IR (neat, cm$^{-1}$) 1711; HRMS (FAB) m/z 1666.8244 (1666.8251 calcd for C$_{96}$H$_{114}$N$_8$O$_{18}$, M$^+$); Anal. Calcd for C$_{96}$H$_{114}$N$_8$O$_{18}$: C, 69.13; H, 6.89. Found: C, 69.28; H, 7.11.

N-(tert-Butoxycarbonyl)-4,4'-dibromodiphenylamine (19). Diphenylamine (4.231 g, 25.0 mmol) was converted to 4,4'-dibromodiphenylamine by the method of Berthelot et al.[28] The crude product and 4-dimethylaminopyridine (0.611 g, 5.00 mmol, 20 mol %) were dissolved in tetrahydrofuran (20 mL) in a Schlenk flask under argon. Di-tert-butyl dicarbonate (neat, 6.30 mL, 27.5 mmol) was added via syringe, and the resulting solution was heated to reflux. After 1 h the mixture was cooled to room temperature and concentrated. Crystallization of the residual solid from methanol afforded the title compound as white crystals with a faint pink cast (8.65 g, 81% based on diphenylamine): mp 113–115° C.; $^1$H NMR: (300 MHz, CDCl$_3$) δ 7.44 (d, J=8.7 Hz, 4H), 7.08 (d, J=8.7 Hz, 4H), 1.46 (s, 9H); $^{13}$C NMR (75 MHz, CDCl$_3$) δ 153.3, 141.9, 132.1, 128.7, 119.5, 82.2, 28.4; IR (neat, cm$^{-1}$) 2977, 1712, 1488, 1322, 1160, 1072, 1011, 824; Anal. Calcd for C$_{17}$H$_{17}$Br$_2$NO$_2$: C, 47.80; H, 4.01. Found: C, 48.02; H, 3.87.

N,N'-Bis(4-bromophenyl)-N,N'-bis(tert-butoycarbonyl)-1,4-phenylenediamine (20). 1,4-Phenylenediamine (1.00 g, 9.25 mmol) 1,4-dibromobenzene (4.58 g, 19.4 mmol), sodium tert-butoxide (2.31 g, 24.0 mmol), Pd$_2$(dba)$_3$ (0.085 g, 0.093 mmol, 1.0 mol %), and S-BINAP (0.173 g, 0.278 mmol, 3.0 mol %) were dissolved in tetrahydrofuran (20 mL) in a Schlenk flask under argon. The reaction mixture was heated to a gentle reflux. Analysis by TLC after 15 h indicated an incomplete reaction. Additional portions of Pd$_2$(dba)$_3$ (0.020 g, 0.022 mmol, 0.24 mol %) and S-BINAP (0.040 g, 0.064 mmol, 0.69 mol %) were added. Analysis by TLC after a further 15 h at reflux indicated a complete reaction. The mixture was cooled to room temperature. Di-tert-butyl dicarbonate (7.07 g, 32.4 mmol) and 4-dimethylaminopyridine (0.226 g, 1.85 mmol, 20 mol %) were added. The resulting solution was heated to a gentle reflux. After 3h the reaction mixture was cooled to room temperature and filtered through a plug of silica gel and Celite, which was then washed with a 1:1 mixture of hexanes and ethyl acetate. The filtrate was concentrated. Crystallization of the residual solid from methanol containing a small proportion of chloroform afforded the title compound as white crystals (3.98 g, 70%): mp 174–176° C.; $^1$H NMR (300 MHz, CDCl$_3$) δ 7.41 (d, J=8.6 Hz, 4H), 7.12 (s, 4H), 7.07 (d, J=8.6 Hz, 4H), 1.43 (s, 18H); $^{13}$C NMR (75 MHz, CDCl$_3$) δ 153.3, 141.9, 140.1, 131.8, 128.4, 127.1, 119.1, 81.7, 28.2; IR (neat, cm$^{-1}$) 2976, 1711, 1510, 1488, 1322, 1159; Anal. Calcd for C$_{28}$H$_{30}$Br$_2$N$_2$O$_4$: C, 54.39; H, 4.89. Found: C, 54.15; H, 4.79.

Octamer dibromide 21. Diamine 17 (2.03 g, 1.62 mmol), 1,4-dibromobenzene (955 mg, 4.05 mmol), sodium tert-butoxide (404 mg, 4.20 mmol), Pd(OAc)$_2$ (14.5 mg, 0.0648 mmol, 4.0 mol %), and BINAP (48.4 mg, 0.0778 mmol, 5 mol %) were dissolved in toluene (15 mL) and triethylamine (3 mL) in a Schlenk flask under argon. The reaction mixture was heated to 90° C. After 48 h, the mixture was cooled to room temperature. 4-Dimethylaminopyridine (20.0 mg, 0.162 mmol, 10 mol %) and a solution of di-tert-butyl dicarbonate in tetrahydrofuran (1.0 M, 5.7 mL, 5.7 mmol) were added. The resulting mixture was heated to 67° C. After 3 h, the mixture was cooled to room temperature, and partitioned between ethyl acetate (50 mL) and a 2.0 M aqueous solution of sodium hydroxide (25 mL). The organic layer was washed with brine (30 mL), dried over sodium sulfate, filtered, and concentrated. Crystallization of the residual solid from isopropanol afforded dibromide 21 as white crystals (2.15 g, 75%): mp 145–147° C.; $^1$H NMR (300 MHz, CDCl$_3$) δ 7.41 (d, J=7.8 Hz, 4H), 7.12 (s, 28H), 7.07 (d, J=7.8 Hz, 4H), 1.43 (s, 72 H); $^{13}$C NMR (75 MHz, CDCl$_3$) δ 153.9, 153.8, 153.6, 153.4, 145.1, 142.0, 140.6, 140.4, 140.2, 139.9, 139.7, 137.6, 133.1, 131.8, 128.4, 128.3, 127.9, 127.0, 124.1, 119.0, 81.6, 81.4, 81.2, 81.1, 28.2; IR (neat, cm$^{-1}$) 1712; Anal. Calcd for C$_{94}$H$_{108}$Br$_2$N$_8$O$_{16}$: C, 63.94; H, 6.16. Found: C, 63.76; H, 5.93.

Phenyl-capped heptamer 22. Arylamine 12 (0.799 g, 1.68 mmol), dibromide 19 (0.326 g, 0.764 mmol), sodium tert-butoxide (0.2153 g, 2.24 mmol), Pd$_2$(dba)$_3$ (14.0 mg, 0.0153 mmol, 2 mol %), and S-BINAP (22.8 mg, 0.0366 mmol, 4.8 mol %) were dissolved in toluene (6 mL) in a Schlenk tube under argon. The reaction mixture was heated to 80° C. with stirring. After 27 h the mixture was cooled to room temperature and taken up in dichloromethane (75 mL). The resulting mixture was washed with brine (50 mL), dried over potassium carbonate, filtered, and concentrated. The residue and 4-dimethylaminopyridine (46.4 mg, 0.38 mmol, 25 mol %) were dissolved in tetrahydrofuran (10 mL) in a Schlenk tube under argon. A solution of di-tert-butyl dicarbonate in tetrahydrofuran (1.0 M, 2.0 mL, 2.0 mmol) was added, and the resulting solution was heated to 60° C. with stirring. After 6 h the solution was cooled to room temperature and concentrated. The residual solid was crystallized from ethanol containing a small proportion of chloroform, and recrystallized from a mixture of ethanol and toluene, to afford heptamer 22 as white crystals (0.647 g, 60%): mp 168–170° C. with slow decomposition; $^1$H NMR (500 MHz, CDCl$_3$) δ 7.31 (at, 4H), 7.21–7.16 (m, 4H), 7.14 (ad, 26H), 1.45 (s, 27H), 1.44 (s, 36H); $^{13}$C NMR (125 MHz, CDCl$_3$) δ 153.9, 153.9, 153.9, 143.0, 140.6, 140.4, 140.2, 128.9, 127.2, 127.2, 125.9, 81.6, 81.5, 81.4, 28.4; IR (neat, cm$^{-1}$) 2977, 2931, 1711, 1509, 1327, 1161, 1057, 757; Anal. Calcd for C$_{83}$H$_{97}$N$_7$O$_{14}$: C, 70.37; H, 6.90. Found: C, 70.15; H, 6.98.

α,ω-Bis(trimethylsilyl)-phenyl-capped nonamer 23. Arylamine 7 (1.301 g, 1.76 mmol), dibromide 19 (0.3417 g, 0.800 mmol), sodium tert-butoxide (0.2153 g, 2.24 mmol), Pd$_2$(dba)$_3$ (14.7 mg, 0.016 mmol, 2 mol %), and S-BINAP (23.9 mg, 0.0384 mol, 4.8 mol %) were dissolved in toluene (7 mL) in a Schlenk tube under argon. The reaction mixture was heated to 80° C. with stirring. After 27 h the mixture was cooled to room temperature and taken up in dichloromethane (75 mL). The resulting mixture was washed with brine (50 mL), dried over potassium carbonate, filtered, and concentrated. The residue and 4-dimethylaminopyridine (48.9 mg, 0.40 mmol, 25 mol %) were dissolved in tetrahydrofuran (10 mL) in a Schlenk tube under argon. A solution of di-tert-butyl dicarbonate in tetrahydrofuran (1.0 M, 2.0 mL, 2.0 mmol) was added. The resulting solution was heated to 60° C. with stirring. After 6 h the solution was cooled to room temperature and concentrated. The residual solid was crystallized from ethanol containing a small proportion of chloroform, and recrystallized from a mixture of ethanol and toluene, to afford nonamer 23 as white crystals (0.970 g, 62%): mp 183–185° C. with slow decomposition; $^1$H NMR (500 MHz, CDCl$_3$) δ 7.45 (d, J=8.3 Hz, 4H), 7.18 (d, J=8.3 Hz, 4H), 7.14 (s, 32H), 1.46 (s, 18H), 1.44 (s, 63H), 0.25 (s, 18H); $^{13}$C NMR (125 MHz, CDCl$_3$) δ 153.9, 153.9, 143.4, 140.5, 140.3, 140.3, 137.7, 133.9, 127.5, 127.2, 126.1, 81.6, 81.5, 81.5, 81.4, 28.4, 28.4, −0.9; IR(neat, cm$^{-1}$) 2976, 2932, 1713, 1509, 1327, 1161, 1057, 851, 756; Anal. Calcd for C$_{111}$H$_{139}$N$_9$O$_{18}$Si$_2$: C, 68.60; H, 7.21. Found: C, 68.57; H, 7.13.

α,ω-Bis(trimethylsilyl)-phenyl-capped decamer 24. Arylamine 7 (1.301 g, 1.76 mmol), dibromide 20 (0.495 g, 0.800 mmol), sodium tert-butoxide (0.2153 g, 2.24 mmol), Pd$_2$(dba)$_3$ (14.7 mg, 0.016 mmol, 2 mol %), and S-BINAP (23.9 mg, 0.0384 mol, 4.8 mol %) were dissolved in toluene (8 mL) in a Schlenk tube under argon. The reaction mixture was heated to 80° C. with stirring. After 27 h the mixture was cooled to room temperature and taken up in dichloromethane (75 mL). The resulting mixture was washed with brine (50 mL), dried over potassium carbonate, filtered, and concentrated. The residue and 4-dimethylaminopyridine (48.9 mg, 0.40 mmol, 25 mol %) were dissolved in tetrahydrofuran (10 mL) in a Schlenk tube under argon. A solution of di-tert-butyl dicarbonate in tetrahydrofuran (1.0 M 2.0 mL, 2.0 mmol) was added. The resulting solution was heated to 60° C. with stirring. After 6 h the solution was cooled to room temperature and concentrated. The residual solid was crystallized from ethanol containing a small proportion of chloroform, and recrystallized from a mixture of ethanol and toluene, to afford decamer 24 as white crystals (1.128 g, 66%): mp 188–189° C. with slow decomposition; $^1$H NMR (500 MHz, CDCl$_3$) δ 7.45 (d, J=7.3 Hz, 4H), 7.19–7.14 (m, 40H), 1.46 (s, 36H), 1.44 (s, 54H), 0.25 (s, 18H); IR (neat, cm$^{-1}$) 2977, 2931, 1713, 1509, 1328, 1161, 1057, 851, 756; Anal. Calcd for C$_{122}$H$_{152}$N$_{10}$O$_{20}$Si$_2$: C, 68.64; H, 7.18. Found: C, 68.84; H, 7.31.

α,ω-Bis(trimethylsilyl)-phenyl-capped 16-mer 25. Dibromide 21 (750 mg, 0.425 mmol), arylamine 7 (659 mg, 0.892 mmol), sodium tert-butoxide (114 mg, 1.19 mmol), Pd(OAc)$_2$ (3.8 mg, 0.0170 mmol, 4.0 mol %), and BINAP (12.7 mg, 0.0204 mmol, 4.8 mol %) were dissolved in toluene (3 mL) and triethylamine (1 mL) in a Schlenk tube under argon. The reaction mixture was heated to 90° C. with stirring. After 18 h, the solution was cooled to room temperature. 4-Dimethylaminopyridine (5.00 mg, 0.0425 mmol, 10 mol %) and a solution of di-tert-butyl dicarbonate in tetrahydrofuran (1.0 M, 1.49 mL, 1.49 mmol) were added, and the resulting mixture was heated to 67° C. After 3 h the solution was cooled to room temperature and partitioned between ethyl acetate (30 mL) and a 2.0 M aqueous solution of sodium hydroxide (20 mL). The organic layer was washed with brine (20 mL), dried over sodium sulfate, filtered, and concentrated. Crystallization of the residual solid from a 10:1 mixture of methanol and chloroform afforded 16-mer 25 as white crystals (1.01 g, 73%): mp 182–185° C.; $^1$H NMR (300 MHz, CDCl$_3$) δ 7.43 (d, J=8.4 Hz, 4H), 7.16 (d, J=8.4, 4H), 7.13 (s, 60H), 1.43 (s, 144H), 0.24 (s, 18H); $^{13}$C NMR (75 MHz, CDCl$_3$) δ 153.6, 143.2, 140.4, 140.2, 137.5, 128.2, 127.0, 126.6, 125.9, 81.3, 28.2, −1.1; IR (neat, cm$^{-1}$) 1713; Anal. Calcd for C$_{188}$H$_{233}$N$_{16}$O$_{32}$Si: C, 68.80; H, 7.06. Found: C, 68.53; H, 6.85.

α,ω-Bis(trimethylsifyI)-phenyl-capped 24-mer (26). Dibromide 21 (177 mg, 0.100 mmol), arylamine 10 (316 mg, 0.210 mmol), sodium tert-butoxide (28.8 mg, 0.300 mmol), Pd(OAc)$_2$ (1.3 mg, 6.0 lmol, 6.0 mol %), and BINAP (4.5 mg, 7.2 lmol, 7.2 mol %) were dissolved in toluene (2 mL) and triethylamine (0.5 mL) in a Schienk tube under argon. The reaction mixture was heated to 90° C. After 18 h the solution was cooled to room temperature. 4-Dimethylaminopyridine (2.40 mg, 0.0200 mmol, 20 mol %) and a solution of di-tert-butyl dicarbonate in tetrahydrofuran (1.0 M, 0.40 mL, 0.40 mmol) were added, and the resulting mixture was heated to 67° C. After 4 h the solution was cooled to room temperature and partitioned between ethyl acetate (30 mL) and a 2.0 M aqueous solution of sodium hydroxide (20 mL). The organic layer was washed with brine (20 mL), dried over sodium sulfate, filtered, and concentrated. Crystallization of the residual solid from isopropanol afforded 24-mer 26 as white crystals (362 mg, 75%): mp 185–188° C.; $^1$H NMR (300 MHz, CDCl$_3$) δ 7.43 (d, J=8.4 Hz, 4H), 7.16 (d, J=8.4, 4H), 7.13 (s, 92H), 1.44 (s, 18H), 1.43 (s, 198H), 0.24 (s, 18H); $^{13}$C NMR (75 MHz, CDCl$_3$) δ 153.5, 143.0, 140.2, 140.0, 137.3, 133.6, 128.0, 127.2, 126.9, 125.8, 81.3, 28.3, −1.1; IR (neat, cm$^{-1}$) 1714; Anal. Calcd for C$_{272}$H$_{334}$N$_{24}$O$_{48}$Si$_2$: C, 68.89; H. 7.00. Found: C, 69.06; H, 6.93.

Chain-Length Confirmation for 16-mer and 24-mer by $^1$H NMR. The oligomer and hexamnethylbenzene were weighed into a vial, dissolved in CD$_2$Cl$_2$ (0.75 mL), and transferred to an NMR tube. Three samples were prepared for each oligomer. Each spectrum was recorded with 16 scans and a relaxation delay of 20 seconds. Relative integration of the resonances for the internal standard, the BOC groups and the trimethylsilyl endgroups yielded the ratios of repeat units to end groups; for each oligomer, the average ratio of the three runs was taken. The spectra are available as Supporting Information.

BOC/TMS ratio calcd for 16-mer 25: 8/1. Found: (8.6±0.3)/1.

BOC/TMS ratio calcd for 24-mer 26: 12/1. Found: (12.5±0.1)/1.

Iodotrimethylsilane. Iodotrimethylsilane was prepared from iodine and hexamethyldisilane according to the procedure of Seitz and Ferreira,[41] except for the use of 1.05 equiv hexamethyldisilane to ensure complete consumption of iodine. The product was vacuum-transferred from a trace of zinc dust and stored in a resealable Schlenk tube under argon, over copper wire. The colorless liquid was approximately 95% pure as judged by $^1$H NMR, the remainder consisting principally of hexamethyldisilane.

General Procedure for Deprotection of Oligomers by Thermolysis. The protected oligomer was heated in a Schlenk tube under argon, for 9 h at 185° C., then cooled to room temperature. The deprotected oligomers were obtained as powders in quantitative yield.

Phenyl-capped octaaniline (27a): No melting observed below 360° C. $^1$H NMR (300 MHz, DMF-d$_7$) δ 7.76 (s, 2H), 7.59 (s, 2H), 7.51 (s, 2H), 7.49 (s, 2H), 7.18 (t, J=7.4 Hz, 4H), 7.10–6.96 (m, 32H), 6.71 (t, J=7.4 Hz, 2H); IR (neat, cm$^{-1}$) 3388, 1598, 1514, 1495, 1292, 1214,814,744, 697.509; UV-vis (NMP) λ$_{max}$ 337 nm (ε=6.6×10$^4$); Anal. Calcd for C$_{54}$H$_{46}$N$_8$: C, 80.37; H. 5.75. Found: C, 80.24; H, 5.62.

α,ω-Bis(cyano)-phenyl-capped octaaniline (27b): No melting observed below 360° C. $^1$H NMR (300 MHz, DMF-d$_7$) δ 8.60 (s, 2H), 7.79 (s, 2H), 7.58 (d, J=8.4 Hz, 4H), 7.53 (s, 2H), 7.52 (s, 2H), 7.14–6.98 (m, 28H); IR (neat, cm$^{-1}$) 3385, 2213, 1602, 1498, 1293, 1237, 1172, 815, 515; UV-vis (NMP) λ$_{max}$ 336 nm (ε=7.3×10$^4$); Anal. Calcd for C$_{56}$H$_{44}$N$_{10}$: C, 78.48; H, 5.17. Found: C, 78.53; H, 4.95.

α,ω-Bis(tert-butyl)phenyl-capped octaaniline (27c): No melting observed below 360° C. $^1$H NMR (300 MHz, DMF-d$_7$) δ 7.60 (s, 2H), 7.48 (s, 2H), 7.43 (s, 2H), 7.41 (s, 2H), 7.16 (d, J=8.7 Hz, 4H), 6.93 (d, J=8.7 Hz, 4H), 6.88–6.82 (m, 28H), 1.22 (s, 18H); IR (neat, cm$^{-1}$) 3389, 2957, 1610, 1499, 1291, 815; UV-vis (NMP) λ$_{max}$ 336 nm (ε=7.8×10$^4$); HRMS (FAB) m/z 918.5090 (918.5097 calcd for C$_{62}$H$_{62}$N$_8$, M$^+$).

α,ω-Bis(n-dodecyl)-phenyl-capped octaaniline (27d): No melting observed below 360° C. $^1$H NMR (300 MHz, DMF-d$_7$) δ 7.64 (s, 2H), 7.54 (s, 2E), 7.49 (s, 2H), 7.48 (s, 2H), 7.06–6.94 (m, 36H), 2.51 (t, J=7.5 Hz, 4H), 1.61–1.50 (m, 4H), 1.36–1.24 (m, 36H), 0.88 (t, J=6.2, 6H); IR (neat, cm$^{-1}$) 3390, 2922, 2852, 1610, 1515, 1498,1293, 1215, 815; UV-vis (NMP) λ$_{max}$ 336 nm (ε=7.3×10$^4$); Anal. Calcd for C$_{78}$H$_{94}$N$_8$: C, 81.92; H, 8.28. Found: C, 81.74; H, 8.09.

α,ω-Bis(methoxy)-phenyl-capped octaaniline (27e): No melting observed below 360° C. $^1$H NMR (300 MHz, DMF-d$_7$) δ 7.48 (s, 4H), 7.47 (s, 4H), 7.01 (d, J=8.7 Hz, 4H), 6.99 (s, 28H), 6.84 (d, J=8.7 Hz, 4H), 3.74 (s, 6H); IR (neat, cm$^{-1}$) 3389, 1514, 1498, 1292, 1237, 815, 515; UV-vis (NMP) λ$_{max}$ 335 nm (ε=5.38×10$^4$); Anal. Calcd for C$_{56}$H$_{50}$N$_8$O$_2$: C, 77.57; H, 5.81. Found: C, 77.37; H, 5.75.

General Procedure for Preparative Deprotection of Oligomers by Iodotrimethylsilane. The protected oligomer (0.020 mmol) was dissolved in anhydrous dichloromethane (5.0 mL) in a Schlenk tube under argon. Iodotrimethylsilane (20% excess) was added dropwise, with stirring, causing the solution to turn a pale yellow color. The solution was stirred for 15–30 min, then degassed methanol (200 μL) was added dropwise. Within seconds, the clear solution became cloudy and deposited a pale yellow precipitate. Degassed triethylamine (200 μL) was added, and the suspension was vacuum-filtered rapidly under air. The collected product was washed with degassed methanol (5 mL) and dried in vacuo, affording a white powder.

Phenyl-capped heptaaniline (28). No melting observed below 360° C. $^1$H NMR (500 MHz, DMF-d$_7$) δ 7.79 (s, 2H), 7.62 (s, 2H), 7.54 (s, 2H), 7.52 (s, 1H), 7.18 (t, J=7.8 Hz, 4H), 7.09–6.99 (m, 28H), 6.71 (t, J=7.1 Hz, 2H); $^{13}$C (125 MHz, DMF-d$_7$) δ 147.3, 141.0, 139.7, 139.2, 138.8, 138.1, 136.2, 131.5, 130.1, 122.2, 120.3, 119.6, 119.3, 119.0, 119.0, 118.2, 115.8; IR (neat, cm$^{-1}$) 3387, 3025, 1598, 1512, 1302, 814; UV-vis (DMF) λ$_{max}$ 334 nm (ε=7.9×10$^4$); Anal. Calcd for C$_{48}$H$_{41}$N$_7$: C, 80.53; H. 5.77. Found: C, 80.52; H, 5.54.

Phenyl-capped nonaaniline (29). No melting observed below 360° C. $^1$H NMR (500 MHz, DMF-d$_7$) δ 7.77 (s, 2H), 7.60 (s, 2H), 7.52 (s, 2H), 7.49 (s, 311), 7.18 (t, J=12.0 Hz, 4H), 7.09–7.00 (m, 36H), 6.70 (t, J=12.5 Hz, 2H); $^{13}$C NMR (125 MHz, DMF-d$_7$) δ 146.5, 140.3, 139.0, 138.6, 138.3, 138.2, 137.9, 137.3, 135.5, 129.4, 121.4, 119.5, 118.9, 118.7, 118.6, 118.4, 118.2, 118.2, 117.4, 115.0; IR (KBr, cm$^{-1}$) 3386, 3021, 1598, 1496, 1290, 814; UV-vis (DMF) $\lambda_{max}$ 336 nm (ε=8.4×10$^4$); Anal. Calcd for C$_{60}$H$_{51}$N$_8$: C, 80.24; H, 5.72. Found: C, 79.99; H, 5.61.

Phenyl-capped decaaniline (30). No melting observed below 360° C. $^1$H NMR (500 MHz, DMF-d$_7$) δ 7.77 (s, 2H), 7.60 (s, 2H), 7.52 (s, 2H), 7.49 (s, 2H), 7.48 (s, 2H), 7.18 (t, J=13.0 Hz, 4H), 7.09–6.98 (m, 40H), 6.71 (t, J=12.0 Hz, 2H); $^{13}$C NMR (125 MHz, DMF-d$_7$) δ 147.3, 141.1, 139.8, 139.3, 139.2, 139.1, 138.9, 138.7, 138.1, 136.2, 134.9, 130.1, 122.2, 120.3, 119.7, 119.5, 119.4, 119.3, 119.2, 119.0, 118.9, 118.2, 115.7; IR (KBr, cm$^{-1}$) 3386, 3021, 1598, 1496, 1289, 815; UV-vis (DMF) $\lambda_{max}$ 336 nm (ε=1.1×105); Anal. Calcd for C$_{66}$H$_{56}$N$_{10}$: C, 80.13; H, 5.71. Found: C, 79.93; H, 5.64.

Phenyl-capped 16-mer (31). No melting observed below 360° C. IR (KBr, cm$^{-1}$) 3378, 3021, 1596, 1496, 1284, 814; UV-vis (DMF) $\lambda_{max}$ 338 nm (ε=1.8×105); Anal. Calcd for C$_{102}$H$_{86}$N$_{16}$: C, 79.77; H, 5.64; N, 14.59. Found: C, 79.59; H, 5.46; N, 14.38.

Phenyl-capped 24-mer (32). No melting observed below 360° C. IR (KBr, cm$^{-1}$) 3378, 3025, 1596, 1496, 1284, 814; UV-vis (DMF) $\lambda_{max}$ 338 nm (ε=2.2×105); Anal. Calcd for C$_{150}$H$_{126}$N$_{24}$: C, 79.55; H, 5.61; N, 14.84. Found: C, 79.52; H, 5.54; N, 14.66.

Preparation of films for electrochemistry. The protected oligomer (10.0 μmol, except 5.00 μmol in the case of 32) was dissolved in anhydrous dichloromethane (5.0 mL) in a Schlenk tube under argon. Iodotrimethylsilane (20% excess) was added dropwise, with stirring, causing the solution to turn a pale yellow color. The solution was stirred for 15 min, then concentrated and dried in vacuo to remove excess iodotrimethylsilane. The residual solid was dissolved in anhydrous dichloromethane (20.0 mL) to form a clear solution. An aliquot of 10.0 μL was withdrawn via syringe and allowed to evaporate on an ITO-coated glass slide.

Electrochemistry. Electrochemical studies were carried out using an EcoChemie Autolab potentiostat. Cyclic voltammograms were recorded at a scan rate of 100 mV/s in a three-electrode cell with a platinum foil counter electrode and a SCE reference electrode. Working electrodes were prepared by evaporation of an oligomer trimethylsilylcarbamate solution, prepared as described above, onto ITO-coated spectroelectrochemistry slides (40½, coated both sides) purchased from Delta Technologies, Limited. Experiments were run under noncontrolled atmosphere using 1.0 M aqueous sulfric acid as the electrolyte.

References and Notes for Example 3

(1) Fritsche, J. *J. Prakt. Chem.* 1840, 20, 453–459.
(2) (a) Parini, V. P.; Kazakova, Z. S.; Berlin, A. A. *Vysokomolekul Soedin.* 1961, 3, 1870–1873. (b) Pohl, H. A.; Engelhardt, E. H. *J. Phys. Chem.* 1962, 66, 2085–2095.
(3) (a) Huang, W.-S.; Humphrey, B. D.; MacDiarmid, A. G. *J. Chem. Soc., Faraday Trans.* 1 1986, 82, 2385–2400. (b) Chen, S.-A.; Fang, W.-G. *Macromolecules* 1991, 24, 1242–1248.
(4) Paul, E. W.; Ricco, A. J.; Wrighton, M. S. *J. Phys. Chem.* 1985, 89, 1441–1447.
(5) Chiang, J.-C.; MacDiarmid, A. G. *Synth. Met.* 1986, 13, 193–205.
(6) Diaz, A. F.; Logan, J. A. *J. Electroanal. Chem. Interfacial Electrochem.* 1980, 111, 111–114.
(7) (a) Cao, Y.; Smith, P.; Heeger, A. J. *Synth. Met.* 1992, 48, 91–97. (b) Cao, Y.; Smith, P.; Heeger, A. J. *Synth. Met.* 1993, 57, 3514–3519. (c) Pron, A.; Osterholm, J. E.; Smith, P.; Heeger, A. J.; Laska, J.; Zagorska, M. *Synth. Met* 1993, 57, 3520–3525.
(8) MacDiarmid, A. G.; Mu, S.-L.; Somasiri, N. L. D.; Wu, G. *Mol. Cryst. Liq. Cryst.* 1985, 121, 187–190.
(9) Kobayashi, T.; Yoneyama, H.; Tamura, H. *J. Electroanal. Chem. Interfacial Electrochem.* 1984, 161, 419–423.
(10) (a) Kaneto, K.; Kaneko, M.; Min, Y.; MacDiarmid, A. G. *Synth. Met.* 1995, 71, 2211–2213. (b) Takashima, W.; Kaneko, M.; Kaneto, K.; MacDiarmid, A. G. *Synth. Met.* 1995, 71, 2265–2266.
(11) (a) DeBerry, D. W. *J. Electrochem. Soc.* 1985, 132, 1022–1026. (b) Ahmad, N.; MacDiarmid, A. G. *Synth. Met.* 1996, 78, 103–110. (c) Lu, W.-K.; Elsenbaumer, R. L.; Wessling, B. *Synth. Met.* 1995, 71, 2163–2166.
(12) (a) Taka, T. *Synth. Met.* 1991, 41, 1177–1180. (b) Colaneri, N. F.; Shacklette, L. W. *IEEE Trans. Instrum. Meas.* 1992, 41, 291. (c) Joo, J.; Epstein, A. J.*Appl. Phys. Lett.* 1994, 65, 2278–2280.
(13) Honzl, J.; Tlustáková, M. *J. Polym. Sci.* 1968, C21, 451–462.
(14) Willstätter, R.; Moore, C. W. *Chem. Ber.* 1907, 40, 2665–2689.
(15) Lu, F.-L.; Wudl, F.; Nowak, M.; Heeger, A. J. *J. Am. Chem. Soc.* 1986, 108, 8311–8313.
(16) Ochi, M.; Furusho, H.; Tanaka, J. *Bull. Chem. Soc. Jpn.* 1994, 67, 1749–1752.
(17) Rebourt, E.; Joule, J. A.; Monkman, A. P. *Synth. Met.* 1997, 84, 65–66.
(18) Zhang, W. J.; Feng, J.; MacDiarmid, A. G.; Epstein, A. J. *Synth. Met.* 1997, 84, 119–120.
(19) (a) Kosugi, M.; Kameyama, M.; Migita, T. *Chem. Lett.* 1983, 927–928. (b) Guram, A. S.; Rennels, R. A.; Buchwald, S. L. *Angew. Chem. Int. Ed. Engl.* 1995, 34, 1348–1350. (c) Wolfe, J. P.; Rennels, R. A.; Buchwald, S. L. *Tetrahedron* 1996, 52, 7525–7546. (d) Wolfe, J. P.; Wagaw, S.; Buchwald, S. L. *J. Am. Chem. Soc.* 1996, 118, 7215–7216. (e) Wagaw, S.; Buchwald, S. L. *J. Org. Chem.* 1996, 61, 7240–7241. (f) Louie, J.; Hartwig, J. F. *Tetrahedron Lett.* 1995, 36, 3609–3612. (g) Driver, M. S.; Hartwig, J. F. *J. Am. Chem. Soc.* 1996, 118, 7217–7218. (h) Wolfe, J. P.; Buchwald, S. L. *J. Org. Chem.* 1997, 62, 1264–1267. (j) Louie, J.; Driver, M. S.; Hamann, B. C.; Hartwig, J. F. *J. Org. Chem.* 1997, 62, 1268–1273. (k) Wolfe, J. P.; Buchwald, S. L. *Tetrahedron Lett.* 1997, 38, 6359–6362. (l) Åhman, J.; Buchwald, S. L. *Tetrahedron Lett.* 1997, 38, 6363–6366. (m) Wolfe, J. P.; Åhman, J.; Sadighi, J. P.; Singer, R. A.; Buchwald, S. L. *Tetrahedron Lett.* 1997, 38, 6367–6370.
(20) For a review of synthetic approaches to conjugated macromolecules with precise length, see: Tour, J.M. *Chem. Rev.* 1996, 96, 537–553.
(21) For the first example of a divergent-convergent synthesis, used to prepare monodisperse polyethylenes, see: Igner, E.; Paynter, O. I.; Simmonds, D. J.; Whiting, M. C. *J. Chem. Soc. Perkin Trans.* 1 1987, 2447–2454.
(22) For a review of electrophilic substitutions of arylsilanes, see: Bennetau, B.; Dunogues, J. *Synlett* 1993, 171–176.
(23) Wessjohann, L.; McGaffin, G.; de Meijere, A. *Synthesis* 1989, 359–363.
(24) Fasth, K.-J.; Antoni, G.; Langström, B. *J. Chem. Soc. Perkin Trans.* 1 1988, 3081–3084.
(25) This compound had been obtained previously by an analogous sequence using 4-bromo-N,N-bis (trimethylsilyl)aniline: Walton, D. R. M. *J. Chem. Soc. C* 1966, 1706–1707. We found it more convenient to use the crystalline and moisture-stable N-(diphenylmethylene)-4-bromoaniline.

(26) For reasons of availability at the time that this work was carried out, we employed S-BINAP. The significantly less expensive racemic form, now available commercially from Strem Chemical Company, is an equally effective ligand in these coupling reactions, with no observable differences in yields.

(27) The corresponding $N_3$-diamine, a core piece for odd-numbered oligomers, has been prepared; see ref. 19m.

(28) Berthelot, J.; Guette, C.; Essayegh, M.; Desbene, P. L.; Basselier, J. J. *Synth. Commun.* 1986, 16, 1641–1645.

(29) Thermal deprotection of BOC-protected pyrroles and indoles has been reported to proceed more rapidly: Rawal, V. H.; Jones, R. J.; Cava, M. P. *J. Org. Chem.* 1987, 52, 19–28.

(30) Removal of benzyl and tert-butyl carbamate groups from peptides using TMSI is well known: Lott, R. S.; Chauhan, V. S.; Stammer, C. H. *J. Chem. Soc. Chem. Commun.* 1979, 495–496.

(31) Ofer, D.; Crooks, R. M.; Wrighton, M. S. *J. Am. Chem. Soc.* 1990, 112, 7869–7879. For other discussions of polyaniline oxidation states, see Refs. 3–5.

(32) Wudl, F.; Angus, R. O.; Lu, F. L.; Allemand, P. M.; Vachon, D. J.; Nowak, M.; Liu, Z. X.; Heeger, A. J. *J. Am. Chem. Soc.* 1987, 109, 3677–3684.

(33) Early studies described a "nigraniline" oxidation state in polyaniline. Described as an intermediate between emeraldine and pernigraniline, it may well have been a mixture of the two. This possibility was not discussed, and the evidence was inconclusive: (a) Willstätter, R.; Dorogi, S. *Chem. Ber.* 1909, 42, 2147–2168. (b) Willstätter, R.; Dorogi, S. *Chem. Ber.* 1909, 42, 4118–4135. (c) Green, A. G.; Woodhead, A. E. *J. Chem. Soc.* 1910, 97, 2388–2403. (d) Green, A. G.; Woodhead, A. E. *J. Chem. Soc.* 1912, 101, 1117–1123.

(34) For a review of π-dimers and π-stacks in conducting polymers, see: Miller, L. L.; Mann, K. R. *Acc. Chem. Res.* 1996, 29, 417–423.

(35) The indium-tin oxide coating is known to be unstable to strong acids; however, immersion of the slides in 1.0 M sulfuric acid, for the short time periods involved in these CV studies, caused no discernible degradation.

(36) The cause of this material loss is unclear. It is possible that the evolution of carbon dioxide during hydrolysis causes blistering of the films, with some initial physical instability.

(37) Some ambiguity is involved in assigning the peak areas, but the first peak is clearly larger, in the CVs of both the heptaaniline and the decaaniline, for any reasonable choice of demarcation. The narrow peak at high potential is smaller than it appears.

(38) Carbazole itself undergoes anodic oxidation at +1.16 V relative to SCE: Ambrose, J. F.; Nelson, R. F. *J. Electrochem. Soc.* 1968, 115, 1159. Conjugation of the carbazole moiety with a protonated iminoquinone might well raise the oxidation potential beyond the range investigated here.

(39) Taguchi, K.; Westheimer, F. H. *J. Org. Chem.* 1971, 36, 1570–1572.

(40) This reaction is carried out under argon; we note that, under air, palladium on carbon may ignite upon contact with methanol. Once started, the imine hydrogenolysis reaction does not require rigorously air-free conditions.

(41) Seitz, D. E.; Ferreira, L. *Synth. Commun.* 1979, 931–939.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for the synthesis of compounds comprising alternating protected heteroatom and aryl moieties, comprising the reaction of an activated compound, comprising alternating heteroatom and aryl moieties and one activated carbon bearing an activated group, with an amino-substituted compound, comprising alternating heteroatom and aryl moieties and an amine, in the presence of a transition metal catalyst under conditions suitable for the transition metal catalyst to effect the formation of a new carbon-nitrogen bond between the activated carbon of said activated compound and the amine of said amino-substituted compound.

2. The method of claim 1, characterized by the general reaction scheme:

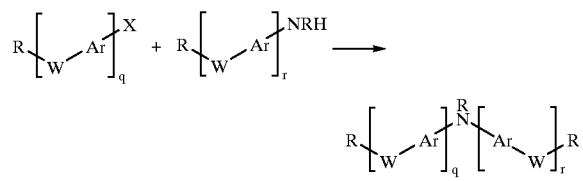

wherein

X represents an activated group which can be replaced by a nucleophilic nitrogen in a transition metal-catalyzed arylation reaction;

W represents, independently for each occurrence, as valence and stability permit, NV, O, S, PR, or Se;

Ar represents, independently for each occurrence, as valence and stability permit, a substituted or unsubstituted aryl group;

V represents, independently for each occurrence, a nitrogen-protecting group;

R represents, independently for each occurrence, as valence and stability permit, H, a substituted or unsubstituted alkyl, aryl, or alkenyl moiety, a formyl, acyl, or sulfonyl moiety, or —$(CH_2)_m$—$R_8$;

$R_8$ represents, independently for each occurrence, a substituted or unsubstituted aryl, cycloalkyl, cycloalkenyl, heterocycle, or polycycle;

m is an integer in the range 0–8 inclusive; and q and r are integers greater than or equal to 1.

3. A method for the synthesis of compounds comprising alternating heteroatom and aryl moieties, comprising the reaction of a bis-activated compound, comprising alternating heteroatom and aryl moieties and two activated carbons bearing activated groups, with two or more equivalents of an amino-substituted compound, comprising alternating heteroatom and aryl moieties and an amine, in the presence of a transition metal catalyst under conditions suitable for the transition metal catalyst to effect the formation of new carbon-nitrogen bonds between the activated carbons of said activated compound and the nitrogens of said amino-substituted compounds.

4. The method of claim 3, characterized by the general reaction scheme:

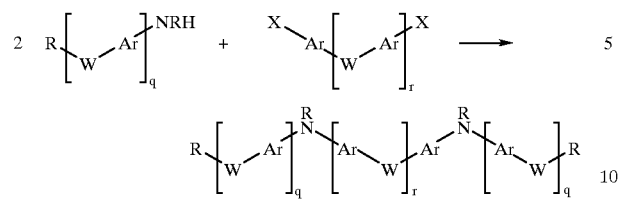

wherein

X represents an activated group which can be replaced by a nucleophilic nitrogen in a transition metal-catalyzed arylation reaction;

W represents, independently for each occurrence, as valence and stability permit, NV, O, S, PR, or Se;

Ar represents, independently for each occurrence, as valence and stability permit, a substituted or unsubstituted aryl group;

V represents, independently for each occurrence, a nitrogen-protecting group;

R represents, independently for each occurrence, as valence and stability permit, H, a substituted or unsubstituted alkyl, aryl, or alkenyl moiety, a formyl, acyl, or sulfonyl moiety, or —$(CH_2)_m$—$R_8$;

$R_8$ represents, independently for each occurrence, a substituted or unsubstituted aryl, cycloalkyl, cycloalkenyl, heterocycle, or polycycle;

m and n are integers in the range 0–8 inclusive; and q and r are integers greater than or equal to 1.

5. A method for the synthesis of compounds comprising alternating heteroatom and aryl moieties, comprising the reaction of two or more equivalents of an activated compound, comprising alternating heteroatom and aryl moieties and one activated carbon bearing an activated group, with a bis-amino-substituted compound, comprising alternating heteroatom and aryl moieties and two amines, in the presence of a transition metal catalyst under conditions suitable for the transition metal catalyst to effect the formation of new carbon-nitrogen bonds between the activated carbons of said activated compounds and the amines of said amino-substituted compounds.

6. The method of claim 5, characterized by the general reaction scheme:

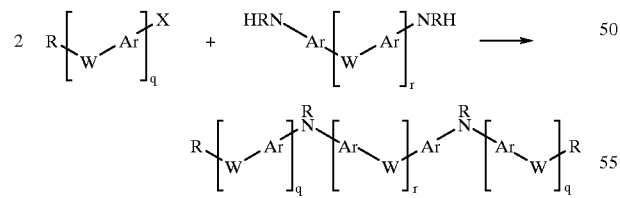

wherein

X represents an activated group which can be replaced by a nucleophilic nitrogen in a transition metal-catalyzed arylation reaction;

W represents, independently for each occurrence, as valence and stability permit, NV, O, S, PR, or Se;

Ar represents, independently for each occurrence, as valence and stability permit, a substituted or unsubstituted aryl group;

V represents, independently for each occurrence, a nitrogen-protecting group;

R represents, independently for each occurrence, as valence and stability permit, H, a substituted or unsubstituted alkyl, aryl, or alkenyl moiety, a formyl, acyl, or sulfonyl moiety, or —$(CH_2)_m$—$R_8$;

$R_8$ represents, independently for each occurrence, a substituted or unsubstituted aryl, cycloalkyl, cycloalkenyl, heterocycle, or polycycle;

m and n are integers in the range 0–8 inclusive; and q and r are integers greater than or equal to 1.

7. The method of claim 1, 3 or 5, wherein all heteroatom moieties are nitrogens bearing nitrogen-protecting groups and all aryl moieties are substituted or unsubstituted phenyl moieties.

8. The method of claim 7, characterized by the general reaction scheme:

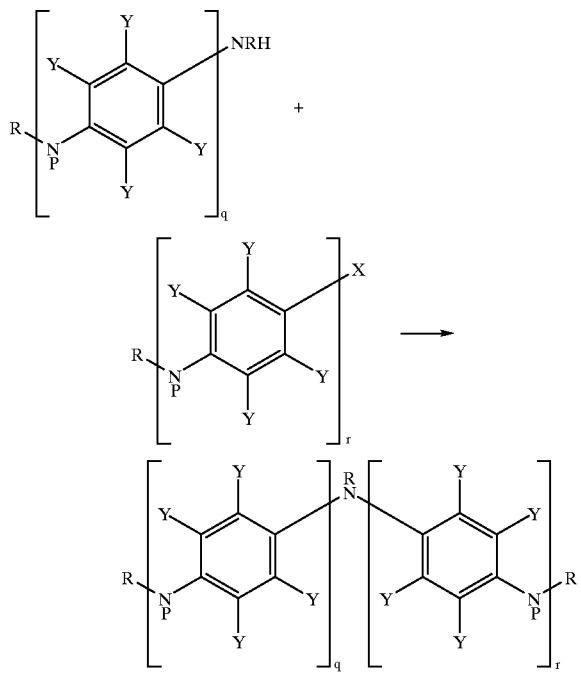

wherein

X represents an activated group which can be replaced by a nucleophilic nitrogen in a transition metal-catalyzed arylation reaction;

P represents, independently for each occurrence, a nitrogen-protecting group;

Y represents, independently for each occurrence, as valence and stability permit, H, halogen, lower alky, lower alkenyl, carbonyl group (e.g. ester, carboxyl, or formyl), thiocarbonyl (e.g. thiolester, thiolcarboxylate, or thiolformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, —$(CH_2)_m$—$R_8$, —$(CH_2)_m$—OH, —$(CH_2)_m$—O-lower alkyl, —$(CH_2)_m$—O-lower alkenyl, —O—$(CH_2)_n$—$R_8$, —$(CH_2)_m$—SH, —$(CH_2)_m$—S-lower alkyl, —$(CH_2)_m$—S-lower alkenyl, —S—$(CH_2)_n$—$R_8$, —$(CH_2)_m$—$NH_2$, —$(CH_2)_m$—NH-lower alkyl, —$(CH_2)_m$—NH-lower alkenyl, —NH—$(CH_2)_n$—$R_8$, or protected forms of the above, or a solid or polymeric support;

R represents, independently for each occurrence, as valence and stability permit, H, a substituted or unsubstituted alkyl, aryl, or alkenyl moiety, a formyl, acyl, or sulfonyl moiety, or —(CH$_2$)$_m$—R$_8$;

R$_8$ represents, independently for each occurrence, a substituted or unsubstituted aryl, cycloalkyl, cycloalkenyl, heterocycle, or polycycle;

m and n are integers in the range 0–8 inclusive; and q and r are integers greater than or equal to 1.

9. The method of claim 7, characterized by the general reaction scheme:

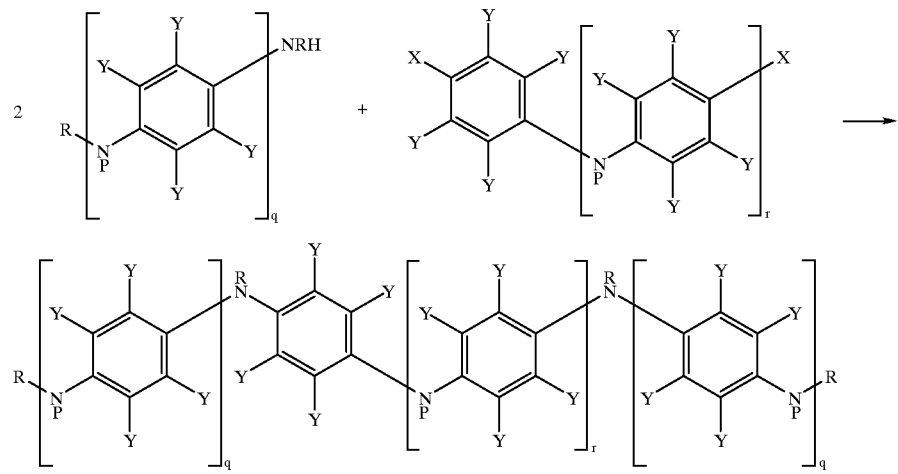

wherein

X represents an activated group which can be replaced by a nucleophilic nitrogen in a transition metal-catalyzed arylation reaction;

P represents, independently for each occurrence, a nitrogen-protecting group;

Y represents, independently for each occurrence, as valence and stability permit, H, halogen, lower alkyl, lower alkenyl, carbonyl group (e.g. ester, carboxyl, or formyl), thiocarbonyl (e.g. thiolester, thiolcarboxylate, or thiolformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, —(CH$_2$)$_m$—R$_8$, —(CH$_2$)$_m$—OH, —(CH$_2$)$_m$—O-lower alkyl, —(CH$_2$)$_m$—O-lower alkenyl, —O—(CH$_2$)$_n$—R$_8$, —(CH$_2$)$_m$—SH, —(CH$_2$)$_m$—S-lower alkyl, —(CH$_2$)$_m$—S-lower alkenyl, —S—(CH$_2$)$_n$—R$_8$, —(CH$_2$)$_m$—NH$_2$, —(CH$_2$)$_m$—NH-lower alkyl, —(CH$_2$)$_m$—NH-lower alkenyl, —NH—(CH$_2$)$_n$—R$_8$, or protected forms of the above, or a solid or polymeric support;

R represents, independently for each occurrence, as valence and stability permit, H, a substituted or unsubstituted alkyl, aryl, or alkenyl moiety, a formyl, acyl, or sulfonyl moiety, or —(CH$_2$)$_m$—R$_8$;

R$_8$ represents, independently for each occurrence, a substituted or unsubstituted aryl, cycloalkyl, cycloalkenyl, heterocycle, or polycycle;

m and n are integers in the range 0–8 inclusive; and q and r are integers greater than or equal to 1.

10. The method of claim 7, characterized by the general reaction scheme:

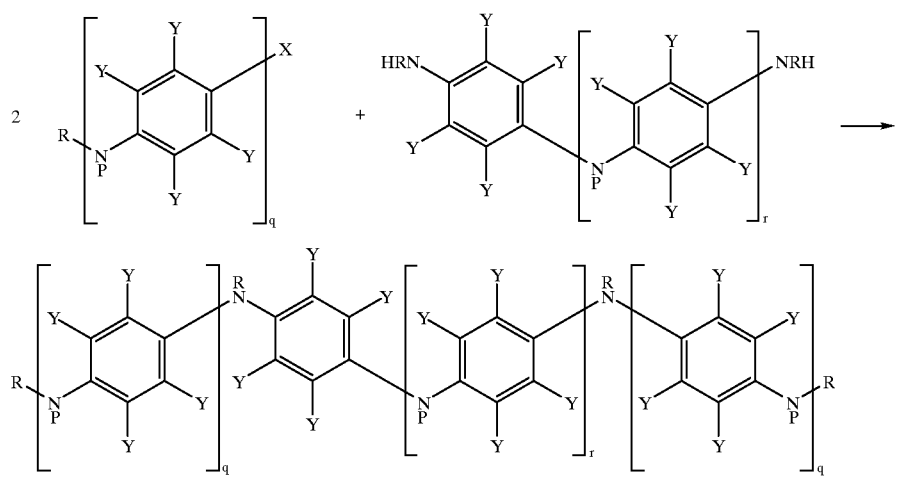

wherein
X represents an activated group which can be replaced by a nucleophilic nitrogen in a transition metal-catalyzed arylation reaction;

Ar represents, independently for each occurrence, as valence and stability permit, an aryl group;

P represents, independently for each occurrence, a nitrogen-protecting group;

Y represents, independently for each occurrence, as valence and stability permit, H, halogen, lower alkyl, lower alkenyl, carbonyl group (e.g. ester, carboxyl, or formyl), thiocarbonyl (e.g. thiolester, thiolcarboxylate, or thiolformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, —$(CH_2)_m$—$R_8$, —$(CH_2)_m$—OH, —$(CH_2)_m$—O-lower alkyl, —$(CH_2)_m$—O-lower alkenyl, —O—$(CH_2)_n$—$R_8$, —$(CH_2)_m$—SH, —$(CH_2)_m$—S-lower alkyl, —$(CH_2)_m$—S-lower alkenyl, —S—$(CH_2)_n$—$R_8$, —$(CH_2)_m$—$NH_2$, —$(CH_2)_m$—NH-lower alkyl, —$(CH_2)_m$—NH-lower alkenyl, —NH—$(CH_2)_n$—$R_8$, or protected forms of the above, or a solid or polymeric support;

R represents, independently for each occurrence, as valence and stability permit, H, a substituted or unsubstituted alkyl, aryl, or alkenyl moiety, a formyl, acyl, or sulfonyl moiety, or —$(CH_2)_m$—$R_8$;

$R_8$ represents, independently for each occurrence, a substituted or unsubstituted aryl, cycloalkyl, cycloalkenyl, heterocycle, or polycycle;

m and n are integers in the range 0–8 inclusive; and q and r are integers greater than or equal to 1.

11. A method for the synthesis of polymers comprising alternating heteroatom and aryl moieties, comprising the polymerization of one or more different activated and amino-substituted compounds, comprising alternating heteroatom and aryl moieties, at least one amine, and at least one activated carbon bearing an activated group, in the presence of a transition metal catalyst under conditions suitable for the transition metal catalyst to effect the formation of a new carbon-nitrogen bond between amines and activated carbons of said activated and amino-substituted compounds.

12. The method of claim 11, characterized by the general reaction scheme:

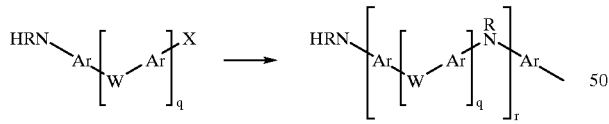

wherein
X represents an activated group which can be replaced by a nucleophilic nitrogen in a transition metal-catalyzed arylation reaction;

W represents, independently for each occurrence, as valence and stability permit, NP, O, S, PR, or Se;

Ar represents, independently for each occurrence, as valence and stability permit, a substituted or unsubstituted aryl group;

P represents, independently for each occurrence, a nitrogen-protecting group;

Y represents, independently for each occurrence, as valence and stability permit, H, halogen, lower alkyl, lower alkenyl, carbonyl group (e.g. ester, carboxyl, or formyl), thiocarbonyl (e.g. thiolester, thiolcarboxylate, or thiolformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, —$(CH_2)_m$—$R_8$, —$(CH_2)_m$—OH, —$(CH_2)_m$—O-lower alkyl, —$(CH_2)_m$—O-lower alkenyl, —O—$(CH_2)_n$—$R_8$, —$(CH_2)_m$—SH, —$(CH_2)_m$—S-lower alkyl, —$(CH_2)_m$—S-lower alkenyl, —S—$(CH_2)_n$—$R_8$, —$(CH_2)_m$—$NH_2$, —$(CH_2)_m$—NH-lower alkyl, —$(CH_2)_m$—NH-lower alkenyl, —NH—$(CH_2)_n$—$R_8$, or protected forms of the above, or a solid or polymeric support;

R represents, independently for each occurrence, as valence and stability permit, H, a substituted or unsubstituted alkyl, aryl, or alkenyl moiety, a formyl, acyl, or sulfonyl moiety, or —$(CH_2)_m$—$R_8$;

$R_8$ represents, independently for each occurrence, a substituted or unsubstituted aryl, cycloalkyl, cycloalkenyl, heterocycle, or polycycle;

m and n are integers in the range 0–8 inclusive;

q is an integer greater than or equal to 1; and r is an integer greater than 1.

13. A method for the synthesis of polymers comprising alternating heteroatom and aryl moieties, comprising the polymerization of one or more different bis-activated compounds, each comprising alternating heteroatom and aryl moieties and two activated carbons bearing activated groups, with one or more different bis-amino-substituted compounds, each comprising alternating heteroatom and aryl moieties and two amines, in the presence of a transition metal catalyst under conditions suitable for the transition metal catalyst to effect the formation of new carbon-nitrogen bonds between amines of said bis-amino-substituted compounds and activated carbons of said bis-activated compounds.

14. The method of claim 13, characterized by the general reaction scheme:

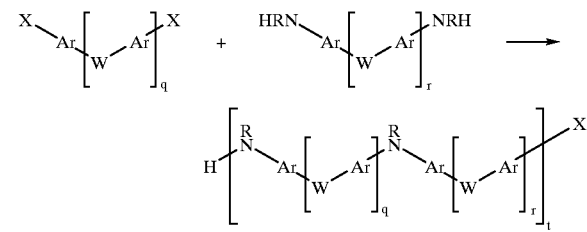

wherein
X represents an activated group which can be replaced by a nucleophilic nitrogen in a transition metal-catalyzed arylation reaction;

W represents, independently for each occurrence, as valence and stability permit, NP, O, S, PR, or Se;

Ar represents, independently for each occurrence, as valence and stability permit, a substituted or unsubstituted aryl group;

P represents, independently for each occurrence, a nitrogen-protecting group;

Y represents, independently for each occurrence, as valence and stability permit, H, halogen, lower alkyl, lower alkenyl, carbonyl group (e.g. ester, carboxyl, or formyl), thiocarbonyl (e.g. thiolester, thiolcarboxylate, or thiolformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, —$(CH_2)_m$—

$R_8$, —$(CH_2)_m$—OH, —$(CH_2)_m$—O-lower alkyl, —$(CH_2)_m$—O-lower alkenyl, —O—$(CH_2)_n$—$R_8$, —$(CH_2)_m$—SH, —$(CH_2)_m$—S-lower alkyl, —$(CH_2)_m$—S-lower alkenyl, —S—$(CH_2)_n$—$R_8$, —$(CH_2)_m$—$NH_2$, —$(CH_2)_m$—NH-lower alkyl, —$(CH_2)_m$—NH-lower alkenyl, —NH—$(CH_2)_n$—$R_8$, or protected forms of the above, or a solid or polymeric support;

R represents, independently for each occurrence, as valence and stability permit, H, a substituted or unsubstituted alkyl, aryl, or alkenyl moiety, a formyl, acyl, or sulfonyl moiety, or —$(CH_2)_m$—$R_8$;

$R_8$ represents, independently for each occurrence, a substituted or unsubstituted aryl, cycloalkyl, cycloalkenyl, heterocycle, or polycycle;

m and n are integers in the range 0–8 inclusive;

q and r are integers greater than or equal to 1; and t is an integer greater than 1.

15. The method of claim 11 or 13, wherein all heteroatom moieties are nitrogens bearing nitrogen-protecting groups and all aryl moieties are substituted or unsubstituted phenyl moieties.

16. The method of claim 15, characterized by the general reaction scheme:

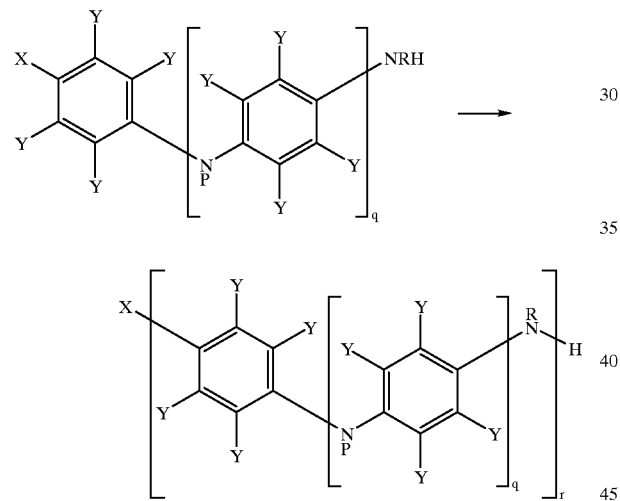

wherein

X represents an activated group which can be replaced by a nucleophilic nitrogen in a transition metal-catalyzed arylation reaction;

P represents, independently for each occurrence, a nitrogen-protecting group;

Y represents, independently for each occurrence, as valence and stability permit, H, halogen, lower alkyl, lower alkenyl, carbonyl group (e.g. ester, carboxyl, or formyl), thiocarbonyl (e.g. thiolester, thiolcarboxylate, or thiolformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, —$(CH_2)_m$—$R_8$, —$(CH_2)_m$—OH, —$(CH_2)_m$—O-lower alkyl, —$(CH_2)_m$—O-lower alkenyl, —O—$(CH_2)_n$—$R_8$, —$(CH_2)_m$—SH, —$(CH_2)_m$—S-lower alkyl, —$(CH_2)_m$—S-lower alkenyl, —S—$(CH_2)_n$—$R_8$, —$(CH_2)_m$—$NH_2$, —$(CH_2)_m$—NH-lower alkyl, —$(CH_2)_m$—NH-lower alkenyl, —NH—$(CH_2)_n$—$R_8$, or protected forms of the above, or a solid or polymeric support;

R represents, independently for each occurrence, as valence and stability permit, H, a substituted or unsubstituted alkyl, aryl, or alkenyl moiety, a formyl, acyl, or sulfonyl moiety, or —$(CH_2)_m$—$R_8$;

$R_8$ represents, independently for each occurrence, a substituted or unsubstituted aryl, cycloalkyl, cycloalkenyl, heterocycle, or polycycle;

m and n are integers in the range 0–8 inclusive;

q is an integer greater than or equal to 1; and r is an integer greater than 1.

17. The method of claim 15, characterized by the general reaction scheme:

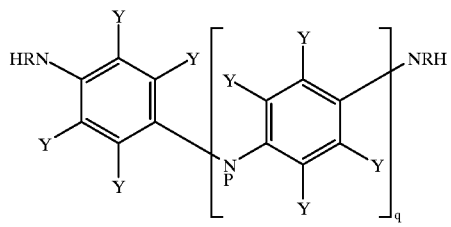

-continued

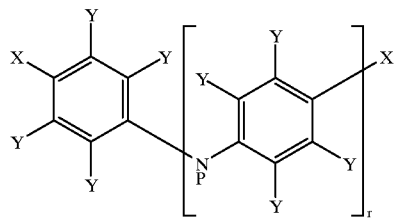

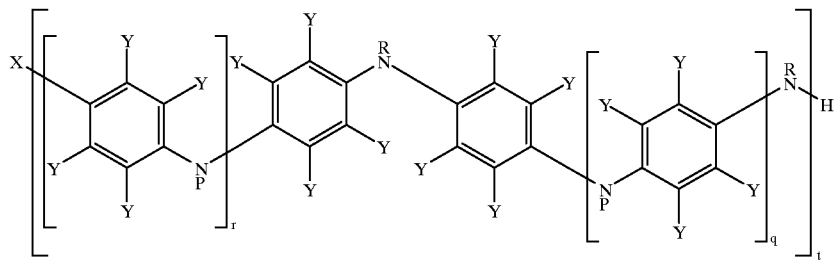

wherein
- X represents an activated group which can be replaced by a nucleophilic nitrogen in a transition metal-catalyzed arylation reaction;
- P represents, independently for each occurrence, a nitrogen-protecting group;
- Y represents, independently for each occurrence, as valence and stability permit, H, halogen, lower alkyl, lower alkenyl, carbonyl group (e.g. ester, carboxyl, or formyl), thiocarbonyl (e.g. thiolester, thiolcarboxylate, or thiolformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, —$(CH_2)_m$—$R_8$, —$(CH_2)_m$—OH, —$(CH_2)_m$—O-lower alkyl, —$(CH_2)_m$—O-lower alkenyl, —O—$(CH_2)_n$—$R_8$, —$(CH_2)_m$—SH, —$(CH_2)_m$—S-lower alkyl, —$(CH_2)_m$—S-lower alkenyl, —S—$(CH_2)_n$—$R_8$, —$(CH_2)_m$—$NH_2$, —$(CH_2)_m$—NH-lower alkyl, —$(CH_2)_m$—NH-lower alkenyl, —NH—$(CH_2)_n$—$R_8$, or protected forms of the above, or a solid or polymeric support;
- R represents, independently for each occurrence, as valence and stability permit, H, a substituted or unsubstituted alkyl, aryl, or alkenyl moiety, a formyl, acyl, or sulfonyl moiety, or —$(CH_2)_m$—$R_8$;
- $R_8$ represents, independently for each occurrence, a substituted or unsubstituted aryl, cycloalkyl, cycloalkenyl, heterocycle, or polycycle;
- m and n are integers in the range 0–8 inclusive;
- q and r are integers greater than or equal to 1; and
- t is an integer greater than 1.

18. The method of claim 15, wherein the polymer synthesized exhibits a polydispersity less than 5.

19. The method of claim 7 or 15, wherein the nitrogen-protecting groups are acyl groups.

20. The method of claim 7 or 15, wherein the nitrogen-protecting groups are carbamates.

21. The method of claim 7 or 15, wherein the carbamates are t-butyl carbamates.

22. The method of claim 1, 3, 5, 7, 11, 13, or 15, wherein the transition metal catalyst is selected from metals in Groups 5–12, inclusive.

23. The method of claim 22, wherein the transition metal catalyst is selected from the group consisting of Fe, Ru, Co, Rh, Ir, Ni, Pd, Pt, and Cu.

24. The method of claim 1, 3, 5, 7, 11, 13, or 15, wherein the transition metal catalyst is present in substoichiometric quantities relative to the limiting reagent among said activated compound, said amino-substituted compound, said activated amino-substituted compound, said bis-activated compound, or said bis-amino-substituted compound.

25. The method of claim 1, 3, 5, 7, 11, 13, or 15, wherein the transition metal catalyst is present in less than or equal to 50 mol % relative to the limiting reagent among said activated compound, said amino-substituted compound, said activated amino-substituted compound, said bis-activated compound, or said bis-amino-substituted compound.

26. The method of claim 1, 3, 5, 7, 11, 13, or 15, wherein the transition metal catalyst is present in less than or equal to 10 mol % relative to the limiting reagent among said activated compound, said amino-substituted compound, said activated amino-substituted compound, said bis-activated compound, or said bis-amino-substituted compound.

27. The method of claim 1, 3, 5, 7, 11, 13, or 15, wherein the transition metal catalyst is present in less than or equal to 5 mol % relative to the limiting reagent among said activated compound, said amino-substituted compound, said activated amino-substituted compound, said bis-activated compound, or said bis-amino-substituted compound.

28. The method of claim 1, 3, 5, 7, 11, 13, or 15, wherein the transition metal catalyst is present in less than or equal to 2.5 mol % relative to the limiting reagent among said activated compound, said amino-substituted compound, said activated amino-substituted compound, said bis-activated compound, or said bis-amino-substituted compound.

29. The method of claim 1, 3, 5, 7, 11, 13, or 15, wherein the activated group is selected from the group comprising halides and sulfonates.

30. The method of claim 29, wherein the activated group is selected from the group comprising chloride, bromide, iodide, tosylate, mesylate, triflate, and nonaflate.

31. The method of claim 1, 3, 5, 7, 11, 13, or 15, wherein the conditions comprise a supporting ligand.

32. The method of claim 31, wherein the ligand is selected from the set comprising phosphine and phosphite ligands.

33. The method of claim 31, wherein the ligand is selected from the set comprising achiral and chiral chelating ligands.

34. The method of claim 31, wherein the ligand is racemic or non-racemic BINAP.

35. The method of claim 1, 3, 5, 7, 11, 13, or 15, wherein a varied library of oligomers is produced via parallel, combinatorial synthetic methods.

36. The method of claim 34, wherein members of the library are attached to solid support.

37. The method of claim 2, 4, 6, 8, 9, 10, 12, 14, 16, or 17, wherein Y or R comprises functionality suitable for use in a sensor.

* * * * *